United States Patent
Becker et al.

(10) Patent No.: US 12,109,269 B2
(45) Date of Patent: *Oct. 8, 2024

(54) CARBORANE HYDROXAMIC ACID MATRIX METALLOPROTEINASE INHIBITORS AND AGENTS FOR BORON NEUTRON CAPTURE THERAPY

(71) Applicant: LOYOLA UNIVERSITY OF CHICAGO, Chicago, IL (US)

(72) Inventors: Daniel Paul Becker, Glenview, IL (US); Marlon Ray Lutz, Jr., Grayslake, IL (US)

(73) Assignee: LOYOLA UNIVERSITY OF CHICAGO, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/175,956

(22) Filed: Feb. 28, 2023

(65) Prior Publication Data

US 2024/0050571 A1    Feb. 15, 2024

Related U.S. Application Data

(63) Continuation of application No. 17/256,403, filed as application No. PCT/US2019/039771 on Jun. 28, 2019, now Pat. No. 11,590,226.

(60) Provisional application No. 62/691,784, filed on Jun. 29, 2018.

(51) Int. Cl.
*A61K 41/00* (2020.01)
*A61K 47/54* (2017.01)
*C07F 7/08* (2006.01)

(52) U.S. Cl.
CPC ........ *A61K 41/0095* (2013.01); *A61K 47/545* (2017.08); *C07F 7/0814* (2013.01)

(58) Field of Classification Search
CPC .................................................. A61K 41/0095
See application file for complete search history.

(56) References Cited

U.S. PATENT DOCUMENTS

| | | |
|---|---|---|
| 6,750,228 B1 | 6/2004 | Barta et al. |
| 11,590,226 B2 | 2/2023 | Becker et al. |
| 2001/0049449 A1 | 12/2001 | Becker et al. |
| 2003/0073718 A1 | 4/2003 | Barta et al. |
| 2004/0097487 A1 | 5/2004 | Li et al. |
| 2006/0084688 A1 | 4/2006 | Barta et al. |
| 2006/0211730 A1 | 9/2006 | Levin et al. |
| 2015/0322093 A1 | 11/2015 | Lee, Jr. et al. |

FOREIGN PATENT DOCUMENTS

| WO | WO-98/39315 A1 | 9/1998 |
|---|---|---|
| WO | WO-99/25687 A1 | 5/1999 |
| WO | WO-00/46221 A1 | 8/2000 |
| WO | WO-00/50396 A1 | 8/2000 |
| WO | WO-00/69821 A1 | 11/2000 |
| WO | WO-2004/091549 A2 | 10/2004 |
| WO | WO-2005/117882 A2 | 12/2005 |

OTHER PUBLICATIONS

Ahrens et al., Incorporation of ortho-carbaboranyl-Ne-modified L-lysine into neuropeptide Y receptor Y1- and Y2-selective analogues, J. Med. Chem., 54(7):2368-77 (2011).
Barth et al., Current status of boron neutron capture therapy of high grade gliomas and recurrent head and neck cancer, Radiat. Oncol., 7:146 (2012).
Becker et al., Orally active MMP-1 sparing a-tetrahydropyranyl and a-piperidinyl sulfone matrix metalloproteinase (MMP) inhibitors with efficacy in cancer, arthritis, and cardiovascular disease, J. Med. Chem., 53(18):6653-80 (2010).
Becker et al., Synthesis and structure-activity relationships of beta- and alpha-piperidine sulfone hydroxamic acid matrix metalloproteinase inhibitors with oral antitumor efficacy, J. Med. Chem., 48(21):6713-30 (2005).
Birkedal-Hansen et al., Matrix metalloproteinases: a review, Crit. Rev. Oral Biol. Med., 4(2):197-250 (1993).
Choi et al., Unexpected Direct Synthesis of N-Vinyl Amides through Vinyl Azide-Enolate [3+2] Cycloaddition, Angew. Chem. Int. Ed. Engl., 56(26):7420-4 (2017).
Dash et al., "Click" Chemistry-Mediated Phenylene-Cored Carborane Dendrimers, Organometallics, 31(7):2931-5 (2012).
Fingleton, MMPs as therapeutic targets—still a viable option?, Semin. Cell Dev. Biol., 19(1):61-8 (2008).
Fisher et al., Recent advances in MMP inhibitor design, Cancer Metastasis Rev., 25(1):115-36 (2006).
Freskos et al., Design and synthesis of MMP inhibitors with appended fluorescent tags for imaging and visualization of matrix metalloproteinase enzymes, Bioorg. Med. Chem. Lett., 23(20):5566-70 (2013).
Gao et al., Nanomaterials for boron and gadolinium neutron capture therapy for cancer treatment, Pure Appl. Chem., 87(2):123-34 (2015).

(Continued)

*Primary Examiner* — David K O'Dell
(74) *Attorney, Agent, or Firm* — MARSHALL, GERSTEIN & BORUN LLP

(57) ABSTRACT

Disclosed herein are novel carborane hydroxamic acid matrix metalloproteinase ("MMP") inhibitors and agents bearing borane-containing moieties and methods for their use in treating or preventing a disease, such as cancer and rheumatoid arthritis. In particular, disclosed herein are compounds of Formula (I) and pharmaceutically acceptable salt thereof: Formula (I) wherein the substituents are as described.

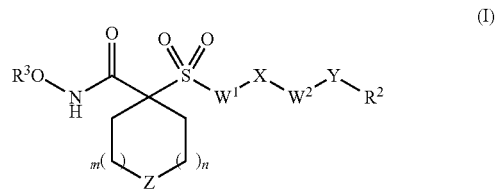

(I)

18 Claims, No Drawings

(56) References Cited

OTHER PUBLICATIONS

Giovenzana et al., Synthesis of carboranyl derivatives of alkynyl glycosides as potential BNCT agents, Tetrahedron, 55(49):14123-36 (1999).
Grimes, Boron clusters come of age, J. Chem. Educ., 81(5):657 (2004).
International Application No. PCT/US2019/039771, International Search Report and Written Opinion, mailed Oct. 3, 2019.
Kliegel et al., Boron chelates of N-substituted hydroxamic acids, Eur. J. Inorg. Chem., 116(7):2616-29 (1983).
Klomp et al., Optimization of localized 19F magnetic resonance spectroscopy for the detection of fluorinated drugs in the human liver, Magn. Reson. Med., 50(2):303-8 (2003).
Leukart et al., L-o-Carboranylalanine, a Boron Analogue of Phenylalanine, Helvetica Chimica Acta, 59(6):2184-7 (1976).
Lutz et al., An Efficient Oxidation of Sulfides to Sulfones with Urea-Hydrogen Peroxide in the Presence of Phthalic Anhydride in Ethyl Acetate, Synthesis, 50(11):2231-4 (2018).
Martel-Pelletier et al., Metalloproteases and inhibitors in arthritic diseases, Best Pract. Res. Clin. Rheumatol., 15(5):805-29 (2001).
Matuszewski et al., Nucleoside bearing boron clusters and their phosphoramidites—building blocks for modified oligonucleotide synthesis, New J. Chem., 39:1202-21 (2015).
Pardridge, The blood-brain barrier: bottleneck in brain drug development, NeuroRx, 2:3-14 (2005).
Ramachandran, Focusing on boron in medicinal chemistry, Future Med. Chem., 5(6):611-12 (2013).
Rostovtsev et al., A stepwise huisgen cycloaddition process: copper(I)-catalyzed regioselective "ligation" of azides and terminal alkynes, Angew Chem Int Ed Engl., 41(14):2596-9 (2002).
Toppino et al., High yielding preparation of dicarba-closo-dodecaboranes using a silver(I) mediated dehydrogenative alkyne-insertion reaction, Inorg. Chem., 52(15):8743-9 (2013).
Valliant et al., The medicinal chemistry of carboranes, Coord. Chem. Rev., 232(1-2):173-230 (2002).
Yinghuai et al, Applications and perspectives of boron-enriched nanocomposites in cancer therapy, Future Med. Chem., 5(6):705-14 (2013).

CARBORANE HYDROXAMIC ACID MATRIX METALLOPROTEINASE INHIBITORS AND AGENTS FOR BORON NEUTRON CAPTURE THERAPY

CROSS REFERENCE TO RELATED APPLICATIONS

The present application claims the priority benefit of U.S. Provisional Patent Application No. 62/691,784, filed Jun. 29, 2018, which is incorporated herein by reference in its entirety.

FIELD

The present disclosure relates to novel carborane hydroxamate matrix metalloproteinase ("MMP") inhibitors and agents bearing boron-containing moieties that are useful for the treatment of diseases, such as cancer and rheumatoid arthritis.

BACKGROUND

Matrix metalloproteinases ("MMPs") are a family of zinc-dependent endopeptidases that are involved in the remodeling and degradation of all components of the extracellular matrix ("ECM"). Birkedal-Hansen et. al., *Critical Reviews in Oral Biology and Medicine* 4(2):197-250 (1993). MMP enzymes play a key role in normal development, morphogenesis, bone remodeling, wound healing, and angiogenesis. However, inappropriately high MMP activity has been implicated in a number of disease states, such as tumor growth and metastasis, and in the degradation of articular cartilage in arthritis. Martel-Pelletier et. al *Best Practice & Research Clinical Rheumatology* 15(5):805-829 (2001). In particular, MMPs are known to be overexpressed in tumors and articular cartilage in patients suffering from rheumatoid and osteoarthritis enzymes.

MMP inhibitors have been extensively explored to halt disease progression resulting from exaggerated matrix remodeling mediated by MMPs. Fisher et al., *Cancer and Metastasis Reviews*, 25(1):115 (2006); Becker et al., *Journal of Medicinal Chemistry* 53:6653-6680 (2010); Becker et al., *J. Med. Chem.* 48:6713-6730 (2005). These inhibitors also have been used for the imaging of cancer cells because they can bind tightly to MMP receptors. Freskos et al., *Bioorg Med Chem Lett* 23:5566-5570 (2013). However, known MMP inhibitors only halt angiogenesis, growth, and metastasis, and must be dosed longer term for inhibitory efficacy. Furthermore, MMP inhibitors still do not directly kill cancer cells, and can lead to the Muscular Skeletal Syndrome (MSS) with longer-term dosing. Fingletonn, *Semin Cell Dev Biol.* 19(1):61-68 (2008).

Carboranes are boron cage molecules that have found use in the treatment of diseases, including various cancers and rheumatoid arthritis most notably through boron neutron capture therapy ("BCNT") and boron neutron capture synovectomy ("BNCS"), respectively. See Valliant et. al., *Coord. Chem. Rev* 232:173-230 (2002). BNCT is a useful binary cancer treatment, in which a drug containing $^{10}B$ atoms is selectively transported into tumor cells and then irradiated with thermal neutrons. A $^{10}B$ nucleus adsorbs a neutron to form an excited $^{11}B$ nucleus, which undergoes decay via fission to emit an α-particle ($^{4}He^{2+}$) as well as a $^{7}Li^{3+}$ ion, both with high kinetic energy. These highly charged particles can damage the surrounding tissue. Because these particles have a range of only about one cell diameter (5-9 μm), the radiation damage is limited to the cell in which they arise, thus avoiding damage to the surrounding tissue. Gao et al., *Pure Appl. Chem.* 87:123-134 (2015). Therefore, BNCT is a potentially promising and precise treatment for cancers.

Current clinically used BNCT drugs (e.g., boronophenylalanine, sodium borocaptate and sodium decahydrodecaborate), however, are deficient in that they are neither tumor-specific nor accumulate homogeneously in tumor cells. Ramachandran *Future Med. Chem.* 5(6):705-714 (2013). Additional BNCT drugs under development are summarized in Barth et al., *Radiation Oncology* 7:146 (2012). These compounds, like the BNCT drugs in clinical investigations, suffer from a low density of boron atoms (i.e., low neutron-capture cross section), an inability to localize at a tumor site, a lack of bioavailability, poor metabolic stability, and/or an inability to measure drug concentration in a tumor.

Accordingly, there is a need for new therapeutics having superior specificity and selectivity to treat cancer and chronic inflammation, such as cancer and rheumatoid arthritis caused by abnormally high MMP activity.

SUMMARY

In one aspect, the disclosure provides a compound having a structure of Formula (I), or a pharmaceutically acceptable salt thereof:

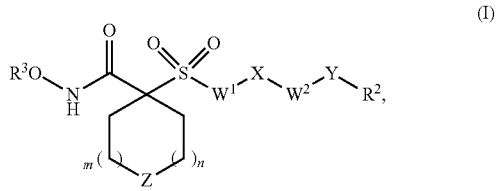

wherein each of m and n is 0 or 1, and m+n is 1 or 2; $W^1$ and $W^2$ are each absent, or one of $W^1$ and $W^2$ is piperdinyl, piperazinyl, or pyrrolidinyl, and the other of $W^1$ and $W^2$ is absent; X is aryl or $C_{3-8}$heteroaryl; Y is $CH_2$, $C_{0-2}$alkylene-O, $C_{0-2}$alkylene-S, $C_{0-2}$alkylene-$NR^3$, C=O, OC=O, OC(=O)$NR^3$, $NR^3$C=O, or absent; Z is $NR^1$, $NSO_2R^1$, O, S, C=O, SO, or $SO_2$; $R^1$ is either (a) $C_{1-6}$alkylene-CB; CH(CB)$_2$, $C_{0-4}$alkylene-CH($C_{1-6}$alkylene-CB)$_2$, $C_{0-4}$alkylene-C($C_{1-6}$alkylene-CB)$_3$, $C_{1-6}$alkylene-$C_{3-8}$heteroaryl-$C_{1-6}$ alkylene-CB, $C_{0-4}$alkylene-CH($C_{1-3}$alkylene-$C_{3-8}$heteroaryl-$C_{0-6}$alkylene-CB)$_2$, or $C_{0-4}$alkylene-C($C_{1-3}$alkylene-$C_{3-8}$heteroaryl-$C_{0-6}$alkylene-CB)$_3$, or (b) H, $C_{1-10}$alkyl, $C_{1-6}$alkynyl, $C_{1-6}$alkylene-O$C_{1-6}$alkyl, $C_{1-6}$alkylene-S$C_{1-6}$alkyl, $C_{1-6}$alkylene-Oaryl, $C_{1-6}$alkylene-Saryl, $C_{0-6}$alkylene-cycloalkyl, $C_{0-6}$alkylene-$C_{3-8}$heterocycloalkyl, $C_{0-6}$alkylene-aryl, or $C_{0-6}$alkylene-$C_{3-8}$heteroaryl; $R^2$ is either (a) $C_{0-6}$alkylene-CB, $C_{1-6}$alkylene-aryl-$C_{0-3}$alkylene-CB, or $C_{1-6}$alkylene-$C_{3-8}$heteroaryl-$C_{1-6}$alkylene-CB, or (b) $C_{0-2}$alkylene-aryl-$R^4$, $C_{0-2}$alkylene-$C_{3-8}$heteroaryl-$R^4$, $C_{0-2}$alkylene-cycloalkyl-$R^4$, or $C_{0-2}$alkylene-$C_{3-8}$heterocycloalkyl-$R^4$, with the proviso that (i) when $R^1$ is absent or (b), then $R^2$ is (a), and (ii) when $R^2$ is (b), then Z is $NR^1$ or $NSO_2R1$, and $R^1$ is (a); $R^3$ is H or $C_{1-3}$alkyl; $R^4$ is H, halo, $C_{1-10}$alkyl, $C_{1-10}$alkenyl, $C_{0-6}$alkylene-cycloalkyl, $C_{0-6}$alkylene-aryl, $C_{0-6}$alkylene-$C_{3-8}$heteroaryl, $C_{0-6}$alkylene-O$C_{1-6}$alkyl, $C_{0-6}$alkylene-S$C_{1-6}$alkyl, $C_{0-6}$alkylene-Oaryl, or $C_{0-6}$alkylene-Saryl; and CB is carborane, wherein each of $C_{3-8}$heteroaryl and $C_{3-8}$heterocycloalkyl include 1, 2, or 3 heteroatoms selected from the group consisting of N, O, and S.

In some embodiments, one of m or n is 0, and the other is 1. In various embodiments, each of m and n is 1.

In some cases, each of $W^1$ and $W^2$ is absent. In various cases, $W^1$ is piperdinyl, piperazinyl, or pyrrolidinyl, and $W^2$ is absent. In some embodiments, $W^2$ is piperdinyl, piperazinyl, or pyrrolidinyl, and $W^1$ is absent. In various embodiments, X is aryl. In some cases, X is phenyleneyl. In various cases, X is heteroaryl. In some embodiments, X is pyridyl. In various embodiments, Y is $CH_2$. In some cases, Y is $C_{0-2}$alkylene-O or $C_{0-2}$alkylene-S. In various cases, Y is O, $CH_2O$, $CH_2CH_2O$, S, $CH_2S$, or $CH_2CH_2S$. In some embodiments, Y is $C_{0-2}$alkylene-$NR^3$. In various embodiments, Y is NH, $CH_2NH$, or $CH_2CH_2NH$. In some cases, Y is C=O, OC=O, OC(=O)$NR^3$, or $NR^3$C=O. In various cases, Y is OC(=O)NH or NHC=O. In some embodiments, Y is absent.

In various embodiments, $R^3$ is H. In some cases, $R^3$ is $C_{1-3}$alkyl. In various cases, $R^3$ is methyl.

In some embodiments, Z is O, S, C=O, SO, or $SO_2$. In various embodiments, Z is O. In some cases, Z is $NR^1$ or $NSO_2R^1$.

In various cases, $R^1$ is $C_{1-6}$alkylene-CB; $CH(CB)_2$, $C_{0-4}$alkylene-CH($C_{1-6}$alkylene-CB)$_2$, $C_{0-4}$alkylene-C($C_{1-6}$alkylene-CB)$_3$, $C_{1-6}$alkylene-heteroaryl-$C_{0-6}$alkylene-CB, $C_{0-4}$alkylene-CH($C_{1-3}$alkylene-heteroaryl-$C_{0-6}$alkylene-CB)$_2$H, or $C_{0-4}$alkylene-C($C_{1-3}$alkylene-heteroaryl-$C_{0-6}$alkylene-CB)$_3$. In some embodiments, $R^1$ is $C_{1-6}$alkylene-CB. In various embodiments, $R^1$ is $CH_2$—CB. In some cases, $R^1$ is $C_{0-4}$alkylene-CH($C_{1-6}$alkylene-CB)$_2$ or $C_{0-4}$alkylene-C($C_{1-6}$alkylene-CB)$_3$. In various cases, $R^1$ is $CH(CB)_2$ $CH(CH_2$—CB)$_2$, $CH(CH_2CH_2$—CB)$_2$, $C(CH_2$—CB)$_3$, $C(CH_2CH_2$—CB)$_3$, or $C(CH_2CH_2CH_2$—CB)$_3$. In some embodiments, $R^1$ is $C_{1-6}$alkylene-heteroaryl-$C_{0-6}$alkylene-CB. In various embodiments, $R^1$ $CH_2$-heteroaryl-$CH_2CH_2$—CB or $CH_2$-heteroaryl-$CH_2CH_2CH_2$—CB. In some cases, $R^1$ is $C_{0-4}$alkylene-CH($C_{1-3}$ alkylene-heteroaryl-$C_{0-6}$alkylene-CB)$_2$H, or $C_{0-4}$alkylene-C($C_{1-3}$alkylene-heteroaryl-$C_{0-6}$alkylene-CB)$_3$. In various cases, $R^1$ is $CH(CH_2$-heteroaryl-CB)$_2$ or $C(CH_2$-heteroaryl-CB)$_3$. In some embodiments, heteroaryl is triazolenyl. In various embodiments, $R^2$ is $C_{0-2}$alkylene-aryl-$R^4$, $C_{0-2}$alkylene-heteroaryl-$R^4$, $C_{0-2}$alkylene-cycloalkyl-$R^4$, or $C_{0-2}$alkylene-heterocycloalkyl-$R^4$. In some embodiments, $R^2$ is $C_{0-2}$alkylene-aryl-$R^4$. In various embodiments, aryl is phenyleneyl. In some cases, $R^2$ is $C_{0-2}$alkylene-heteroaryl-$R^4$. In various cases, heteroaryl is pyrrazolyl or pyridylenyl. In some embodiments, $R^2$ is $C_{0-2}$alkylene-cycloalkyl-$R^4$ or $C_{0-2}$alkylene-heterocycloalkyl-$R^4$. In various embodiments, cycloalkyl is cyclopentyl, cyclohexyl, or tetrahydropyranyl. In some cases, heterocycloalkyl is pyrrolidinylenyl or piperdinylenyl. In various cases, $R^4$ is H. In some embodiments, $R^4$ is halo. In various embodiments, $R^4$ is Br, Cl, or F. In some cases, $R^4$ is $C_{1-10}$alkyl, or $C_{1-10}$alkenyl. In various cases, $R^4$ is selected from the group consisting of Me, Et, Pr, $^iPr$, $CF_3$ and $CF_2CF_3$. In some embodiments, $R^4$ is $CF_3$. In various embodiments, $R^4$ is $C_{0-6}$alkylene-cycloalkyl. In some cases, the cycloalkyl group is cyclopropyl. In various cases, $R^4$ is $C_{0-6}$alkylene-aryl or $C_{0-6}$alkylene-heteroaryl. In some embodiments, the aryl group is phenyl. In various embodiments, $R^4$ is Ph. In some cases, the heteroaryl group is pyridinyl. In various cases, $R^4$ is $C_{0-6}$alkylene-O$C_{1-6}$alkyl, $C_{0-6}$alkylene-S$C_{1-6}$alkyl, $C_{0-6}$alkylene-Oaryl, or $C_{0-6}$alkylene-Saryl. In some embodiments, $R^4$ is selected from the group consisting of $OCH_3$ $OCF_3$, $OCF_2CF_3$, and $SCF_3$. In various embodiments, $R^4$ is $OCF_3$.

In some cases, $R^1$ is H, $C_{1-10}$alkyl, $C_{1-6}$alkynyl, $C_{1-6}$alkylene-O$C_{1-6}$alkyl, $C_{1-6}$alkylene-S$C_{1-6}$alkyl, $C_{1-6}$alkylene-Oaryl, $C_{1-6}$alkylene-Saryl, $C_{0-6}$alkylene-cycloalkyl, $C_{0-6}$alkylene-heterocycloalkyl, $C_{0-6}$alkylene-aryl, or $C_{0-6}$alkylene-heteroaryl. In various cases, $R^1$ is H. In some embodiments, $R^1$ is $C_{1-10}$alkyl or $C_{1-6}$alkynyl. In various embodiments, $R^1$ is Me or $CH_2CCH$. In some cases, $C_{1-6}$alkylene-O$C_{1-6}$alkyl or $C_{1-6}$alkylene-S$C_{1-6}$alkyl. In various cases, $R^1$ is $CH_2CH_2OCH_3$. In some embodiments, $R^1$ is $C_{1-6}$alkylene-Oaryl, $C_{1-6}$alkylene-Saryl, $C_{0-6}$alkylene-aryl, or $C_{0-6}$alkylene-heteroaryl. In various embodiments, aryl is phenyl. In some cases, $R^1$ is $C_{0-6}$alkylene-cycloalkyl or $C_{0-6}$alkylene-heterocycloalkyl. In various cases, cycloalkyl is cyclopropyl, cyclopentyl, or cyclohexyl, and heterocycloalkyl is piperidinyl or pyrrolidinyl. In some embodiments, $R^1$ is cyclopropyl. In various embodiments, $R^2$ is $C_{0-6}$alkylene-CB, $C_{1-6}$alkylene-aryl-$C_{0-3}$alkylene-CB, or $C_{1-6}$alkylene-heteroaryl-$C_{1-6}$alkylene-CB. In some cases, $R^2$ is $C_{0-6}$alkylene-CB. In various cases, $R^2$ is $CH_2$—CB. In some embodiments, $R^2$ is $C_{1-6}$alkylene-heteroaryl-$C_{1-6}$alkylene-CB. In various embodiments, heteroaryl is triazolenyl. In some cases, $R^2$ is $CH_2$-triazolenyl-$CH_2CH_2CH_2$—CB.

In some embodiments, CB is substituted with a fluoroalkyl group. In various embodiments, the fluoroalkyl group is $CF_3$.

In some cases, provided herein is a compound is selected from the group consisting of:

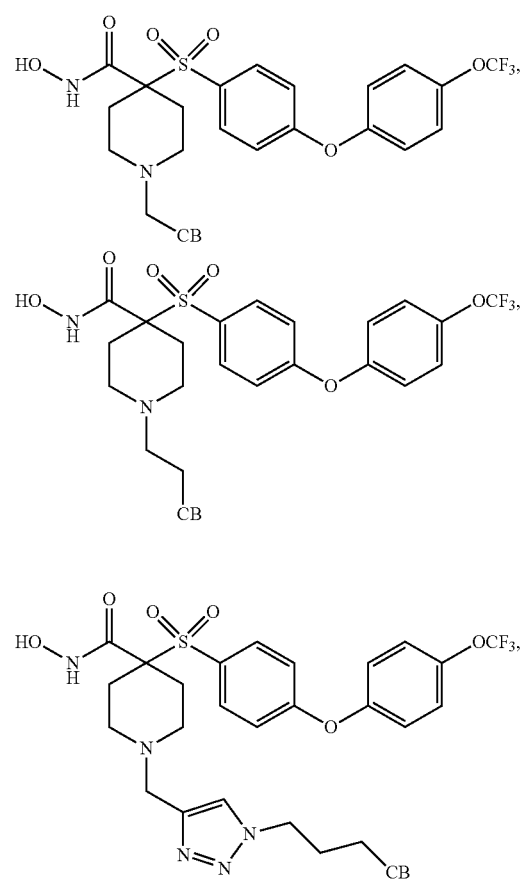

-continued
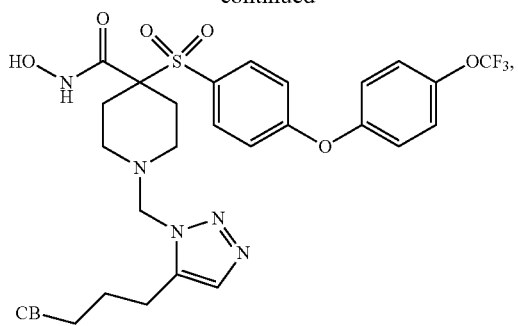
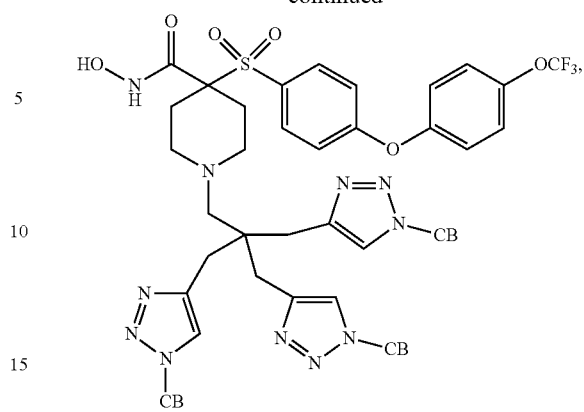
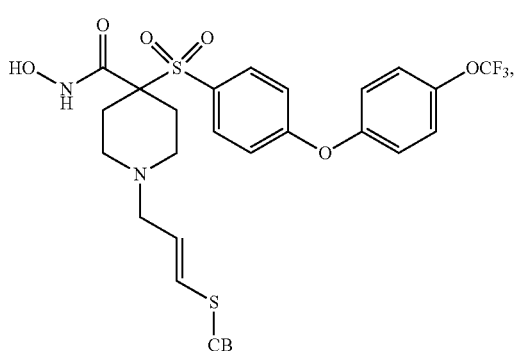
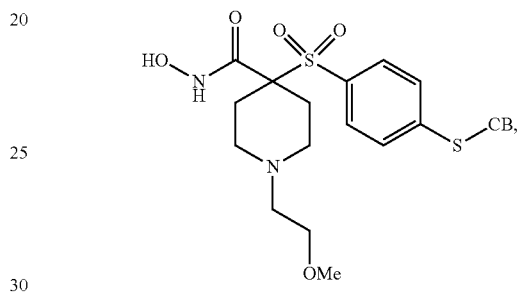
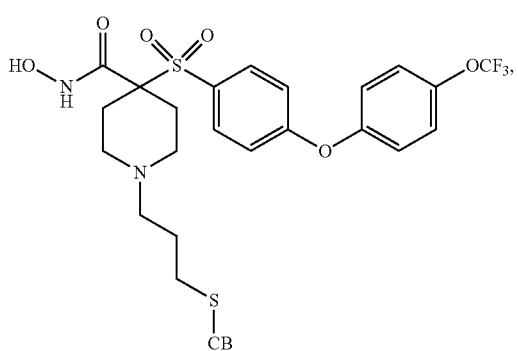
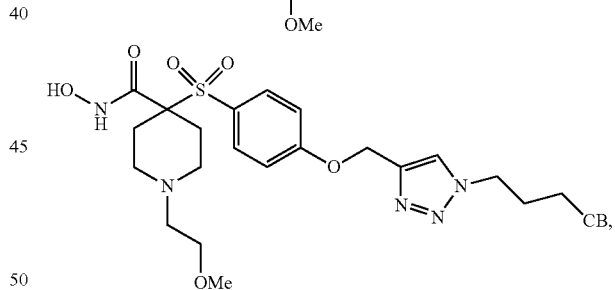
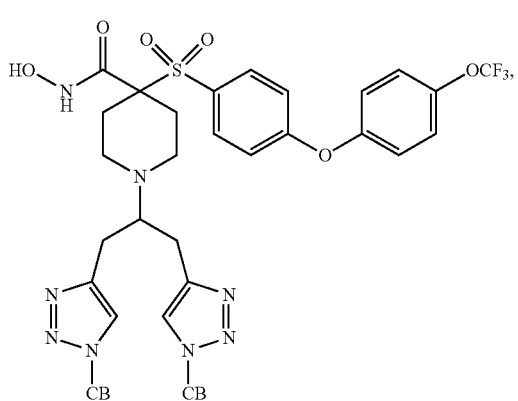
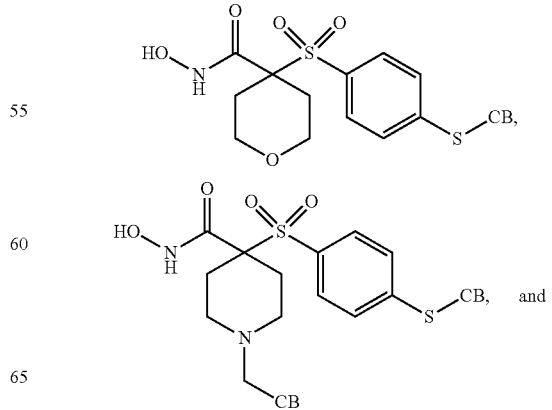
and -continued

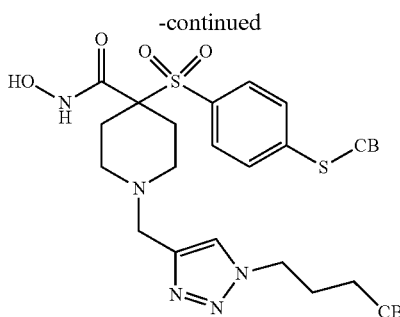

or a pharmaceutically acceptable salt thereof.

Another aspect of the disclosure provides a pharmaceutical formulation comprising the compound or salt described herein and a pharmaceutically acceptable excipient.

Yet another aspect of the disclosure provides a method of inhibiting matrix metalloproteinase ("MMP") in a cell, comprising contacting the cell with the compound or salt of described herein, or the composition described herein, in an amount effective to inhibit MMP. In some embodiments, the MMP is MMP-13, MMP-2, MMP-9, or a combination thereof. In various embodiments, the contacting occurs in vivo. In some cases, the contacting comprises administering to a subject in need thereof. In various cases, the subject suffers from cancer, rheumatoid arthritis, or both.

Another aspect of the disclosure provides a method of treating a disease in a subject comprising administering to the subject a therapeutically effective amount of the pharmaceutical formulation described herein. In some embodiments, the disease is cancer or rheumatoid arthritis.

A further aspect of the disclosure provides a tert-butyldimethylsilyl ether propyl azido carborane compound having a structure:

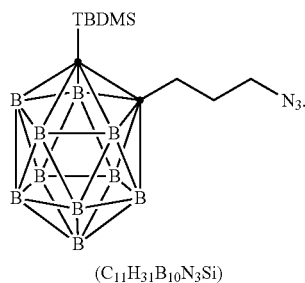

$(C_{11}H_{31}B_{10}N_3Si)$

DETAILED DESCRIPTION

Disclosed herein are orally bioavailable matrix metalloproteinase ("MMP") inhibitors and agents that bind with high potency and specificity to overexpressed MMP enzymes. The inhibitors and agents described herein exhibit long half-lives, have good metabolic stability, and low clearance. Because the inhibitors and agents described herein have a high potency for a range of MMP enzymes, such as the collagenase MMP-13 and the gelatinases MMP-2 and MMP-9, they can accumulate in tumors and inhibit angiogenesis, invasion, and metastasis of tumors, as well as MMP-induced destruction of articular cartilage.

The inhibitors and agents described herein have a high neutron-capture cross section, and work by delivering a high density of boron atoms to tumors to enable binary treatment of the tumors using boron neutron capture therapy ("BCNT"). These inhibitors and agents also can deliver a high density of boron atoms to arthritic tissue to treat the tissue using boron neutron capture synovectomy ("BNCS").

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_{2-7}$ alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkynyl" is defined identically as "alkyl" except for containing at least one carbon-carbon triple bond, and having two to thirty carbon atoms, for example, two to twenty carbon atoms, or two to ten carbon atoms. The term $C_n$ means the alkynyl group has "n" carbon atoms. For example, $C_4$ alkynyl refers to an alkynyl group that has 4 carbon atoms. $C_{2-7}$ alkynyl refers to an alkynyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkynyl groups include ethynyl, 1-propynyl, 2-propynyl, and butynyl. Unless otherwise indicated, an alkynyl group can be an unsubstituted alkynyl group or a substituted alkynyl group.

As used herein, the term "alkylene" refers to an alkyl group having a substituent. For example, the term "alkylene-aryl" refers to an alkyl group substituted with an aryl group. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group.

As used herein, the term "heterocycloalkyl" is defined similarly as cycloalkyl, except the ring contains one to three heteroatoms independently selected from oxygen, nitrogen, and sulfur. Nonlimiting examples of heterocycloalkyl groups include piperdine, pyrazolidine, tetrahydrofuran, tetrahydropyran, dihydrofuran, morpholine, thiophene, pyrrolidine, and the like. Cycloalkyl and heterocycloalkyl groups are non-aromatic, and can be saturated or partially unsaturated ring systems optionally substituted with, for example, one to three groups, independently selected alkyl, alkyleneOH, $C(O)NH_2$, $NH_2$, oxo (=O), aryl, haloalkyl, halo, and OH. Heterocycloalkyl groups optionally can be further N-substituted with alkyl, hydroxyalkyl, alkylenearyl, and alkyleneheteroaryl.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, "halo" refers to fluoro, chloro, bromo, or iodo.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, ether, polyether, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

As used herein, the term "therapeutically effective amount" means an amount of a compound or combination of therapeutically active compounds (e.g., an MMP inhibitor or agent, or combination of MMP inhibitors and/or agents) that ameliorates, attenuates or eliminates one or more symptoms of a particular disease or condition (e.g., cancer), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans). The terms patient and subject includes males and females.

As used herein, the term "pharmaceutically acceptable" means that the referenced substance, such as a compound of the present invention, or a formulation containing the compound, or a particular excipient, are safe and suitable for administration to a patient or subject. The term "pharmaceutically acceptable excipient" refers to a medium that does not interfere with the effectiveness of the biological activity of the active ingredient(s) and is not toxic to the host to which it is administered.

As used herein the terms "treating", "treat" or "treatment" and the like also include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

As used herein, the term "MMP agent" refers to a compound that binds to MMP.

Carborane Hydroxamic Acid MMP Inhibitors and Agents

In one aspect, the inhibitors and agents of the disclosure have a structure of Formula (I), or a pharmaceutically acceptable salt thereof:

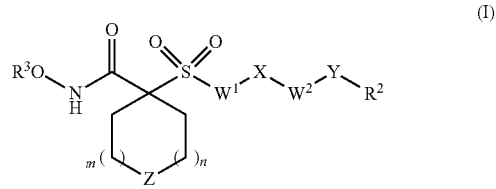

wherein
each of m and n is 0 or 1, and m+n is 1 or 2;
$W^1$ and $W^2$ are each absent, or one of $W^1$ and $W^2$ is piperdinyl, piperazinyl, or pyrrolidinyl, and the other of $W^1$ and $W^2$ is absent;
X is aryl or $C_{3-8}$heteroaryl;
Y is $CH_2$, $C_{0-2}$alkylene-O, $C_{0-2}$alkylene-S, $C_{0-2}$alkylene-$NR^3$, C=O, OC=O, OC(=O)$NR^3$, $NR^3$C=O, or absent;
Z is $NR^1$, $NSO_2R^1$, O, S, C=O, SO, or $SO_2$;
$R^1$ is either
  (a) $C_{1-6}$alkylene-CB; $CH(CB)_2$, $C_{0-4}$alkylene-$CH(C_{1-6}$alkylene-CB)$_2$, $C_{0-4}$alkylene-$C(C_{1-6}$alkylene-CB)$_3$, $C_{1-6}$alkylene-$C_{3-8}$heteroaryl-$C_{1-6}$alkylene-CB, $C_{0-4}$alkylene-CH($C_{1-3}$alkylene-$C_{3-8}$heteroaryl-$C_{1-6}$alkylene-CB)$_2$, or $C_{0-4}$alkylene-C($C_{1-3}$alkylene-$C_{3-8}$heteroaryl-$C_{1-6}$alkylene-CB)$_3$, or
  (b) H, $C_{1-10}$alkyl, $C_{1-6}$alkynyl, $C_{1-6}$alkylene-O$C_{1-6}$alkyl, $C_{1-6}$alkylene-S$C_{1-6}$alkyl, $C_{1-6}$alkylene-Oaryl, $C_{1-6}$alkylene-Saryl, $C_{0-6}$alkylene-cycloalkyl, $C_{0-6}$alkylene-$C_{3-8}$heterocycloalkyl, $C_{0-6}$alkylene-aryl, or $C_{0-6}$alkylene-$C_{3-8}$heteroaryl;
$R^2$ is either
  (a) $C_{0-6}$alkylene-CB, $C_{1-6}$alkylene-aryl-$C_{0-3}$alkylene-CB, or $C_{1-6}$alkylene-$C_{3-8}$heteroaryl-$C_{1-6}$alkylene-CB, or (b) $C_{0-2}$alkylene-aryl-$R^4$, $C_{3-8}$heteroaryl-$R^4$, $C_{0-2}$alkylene-cycloalkyl-$R^4$, or $C_{0-2}$alkylene-$C_{3-8}$heterocycloalkyl-$R^4$, with the proviso that
(i) when $R^1$ is absent or (b), then $R^2$ is (a), and
(ii) when $R^2$ is (b), then Z is $NR^1$ or $NSO_2R^1$, and $R^1$ is (a);

$R^3$ is H or $C_{1-3}$alkyl;

$R^4$ is H, halo, $C_{1-10}$alkyl, $C_{1-10}$alkenyl, $C_{0-6}$alkylene-cycloalkyl, $C_{0-6}$alkylene-aryl, $C_{0-6}$alkylene-heteroaryl, $C_{0-6}$alkylene-O$C_{1-6}$alkyl, $C_{0-6}$alkylene-S$C_{1-6}$alkyl, $C_{0-6}$alkylene-Oaryl, or $C_{0-6}$alkylene-Saryl; and CB is carborane, wherein each of $C_{3-8}$heteroaryl and $C_{3-8}$heterocycloalkyl include 1, 2, or 3 heteroatoms selected from the group consisting of N, O, and S.

In some embodiments, one of m or n is 0 and the other is 1. In these embodiments, the compound of Formula (I) has a structure of Formula (Ia') or (Ia"):

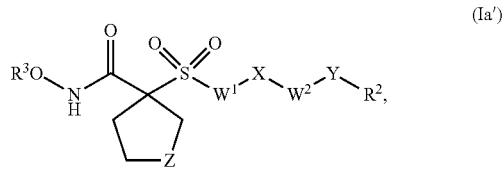
(Ia')

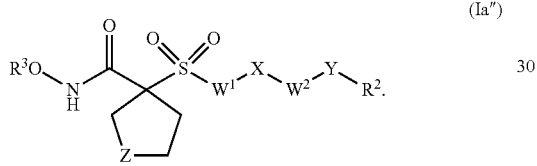
(Ia")

In various embodiments, each of m and n is 1, and the compound of Formula (I) has a structure of Formula (Ib):

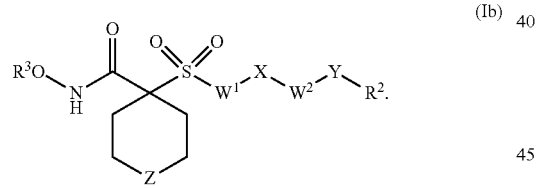
(Ib)

In some cases, W and W are each absent and the compound of Formula (I) has a structure of Formula (II), such as Formula (IIa'), Formula (IIa") or Formula (IIb):

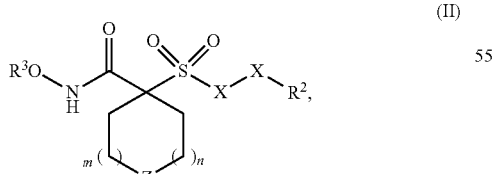
(II)

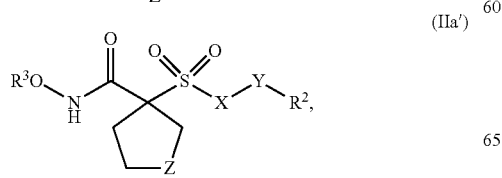
(IIa')

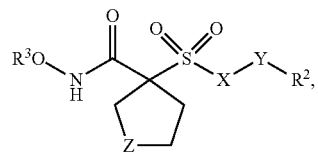
(IIa")

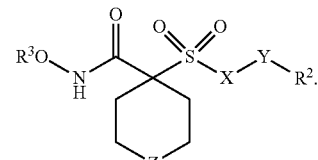
(IIb)

In various cases, $W^1$ is piperdinyl, piperazinyl, or pyrrolidinyl and $W^2$ is absent. In these cases, the compound of Formula (I) has a structure of Formula (III), such as Formula (IIIa'), Formula (IIIa"), or Formula (IIIb).

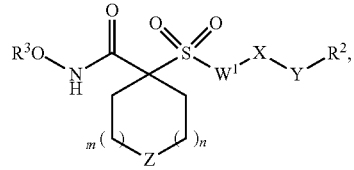
(III)

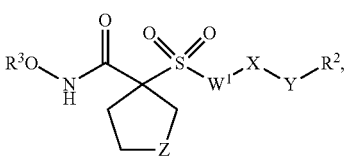
(IIIa')

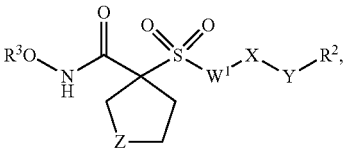
(IIIa")

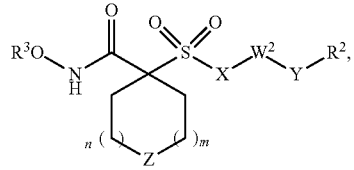
(IIIb)

In some cases, $W^1$ is piperdinyl. In various embodiments, $W^1$ is piperazinyl. In some embodiments, $W^1$ is pyrrolidinyl.

In some embodiments, $W^2$ is piperdinyl, piperazinyl, or pyrrolidinyl and $W^1$ is absent. In these embodiments, the compound of Formula (I) has a structure of Formula (IV), such as Formula (IVa'), Formula (IVa"), or Formula (IVb).

(IV)

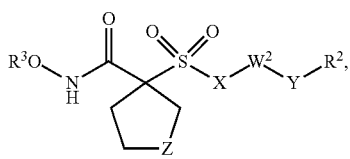
(IVa')

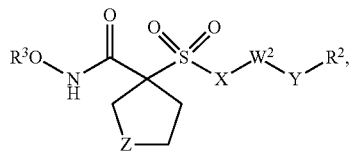
(IVa")

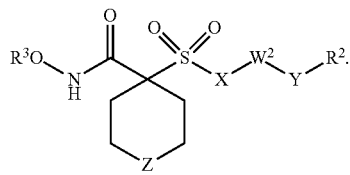
(IVb)

In some of these cases, $W^2$ is piperdinyl. In various cases, $W^2$ is piperazinyl. In some embodiments, $W^2$ is pyrrolidinyl.

The following selections are envisioned for any of the formulas disclosed herein (e.g., I, Ia', Ia", Ib, II, IIa', IIa", IIb, III, IIIa', IIIa", IIIb, IV, IVa', IVa", or IVb). In some cases, X is aryl. Suitable aryl groups include, but are not limited to, phenylenyl, naphthylenyl, tetrahydronaphthylenyl, phenanthrenylenyl, indanylenyl, indenylenyl, anthracenylenyl, and fluorenylenyl. In some embodiments, X is phenylenyl or naphthalenenyl. In some cases, X is phenylenyl. In various cases, X is heteroaryl. Suitable heteroaryl groups include, but are not limited to, pyridylenyl, pyrazinylenyl, pyrimidinylenyl, pyrrolylenyl, pyrazolylenyl, imidazolylenyl, thiazolylenyl, triazolenyl, tetrazolylenyl, oxazolylenyl, isooxazolylenyl, thiadiazolylenyl, oxadiazolylenyl, furanylenyl, thiophenenyl, quinolinylenyl, isoquinolinylenyl, benzoxazolylenyl, benzimidazolylenyl, and benzothiazolylenyl. For example, X can be pyrazolylenyl. In some cases, compounds of Formula (I) can have a structure selected from the group consisting of:

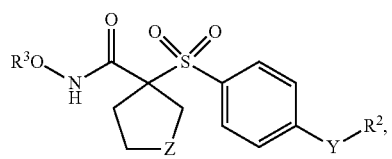

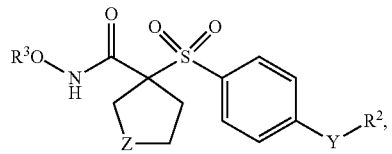

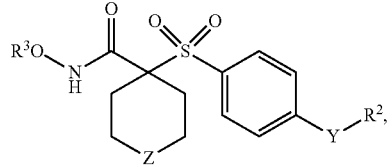

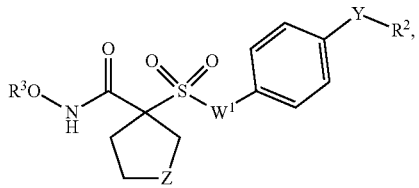

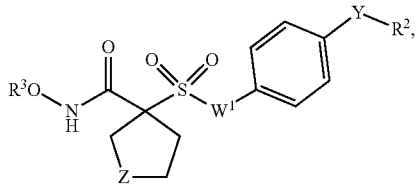

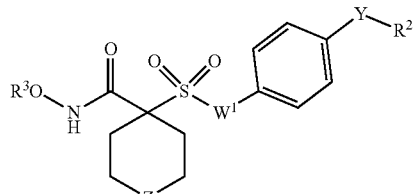

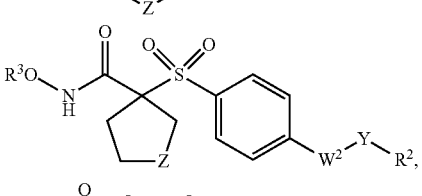

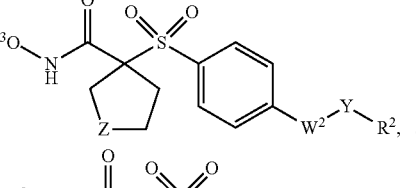
and

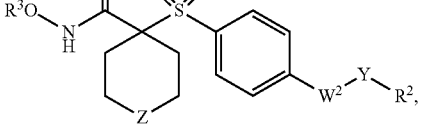

or a pharmaceutically acceptable salt thereof.

The following selections are envisioned for any of the formulas disclosed herein (e.g., I, Ia', Ia", Ib, II, IIa', IIa", IIb, III, IIIa', IIIa", IIIb, IV, IVa', IVa", or IVb). In some embodiments, Y is $CH_2$. In various embodiments, Y is $C_{0-2}$alkylene-O (e.g., O, $CH_2O$, or $CH_2CH_2O$). In some embodiments, Y is $C_{0-2}$alkylene-S (e.g., S, $CH_2S$, or $CH_2CH_2S$). In some cases, Y is $C_{0-2}$alkylene-$NR^3$ (e.g., $NR_3$, $CH_2NR_3$, or $CH_2CH_2NR_3$). In some of these cases, $R^3$ can be H, and Y can be NH, $CH_2NH$, or $CH_2CH_2NH$. In various of these cases, $R^3$ can be $C_{1-3}$akyl (Me, Et, Pr, or Pr). For example, Y can be NMe, $CH_2NMe$, or $CH_2CH_2NMe$. In some embodiments, Y is C=O, OC=O, OC(=O)$NR^3$, or $NR^3$C=O. In some of these embodiments, $R^3$ is H and Y is OC(=O)NH or NHC=O. In various of these embodiments, $R^3$ can be $C_{1-3}$alkyl (Me, Et, Pr, or Pr). For example, Y can be OC(=O)NMe or NMeC=O. In various cases Y is absent. In some cases, compounds of Formula (I) can have a structure selected from the group consisting of:

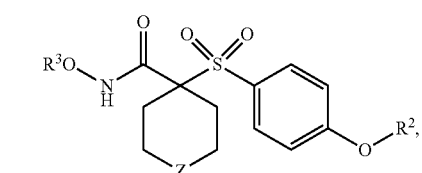
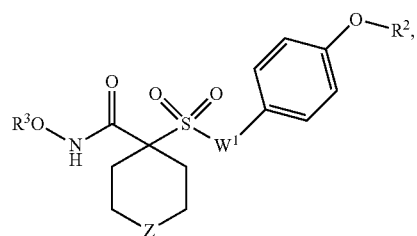
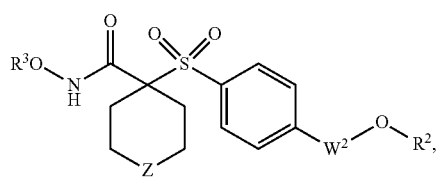
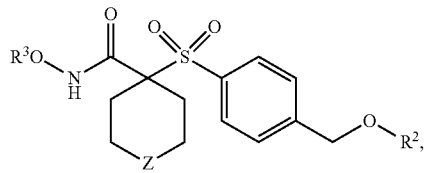
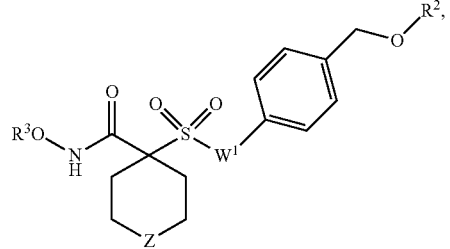
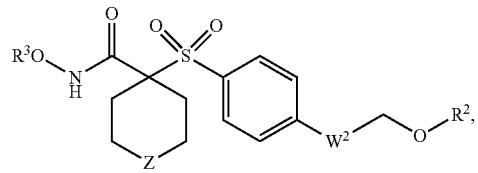
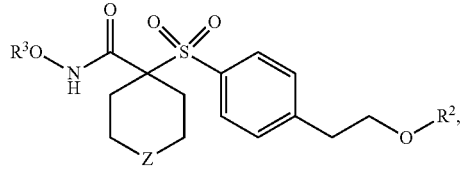
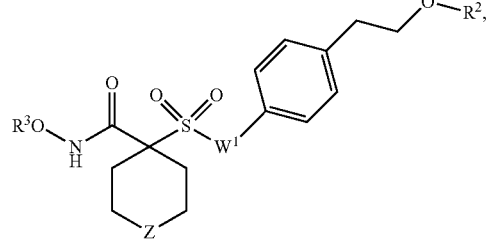
-continued
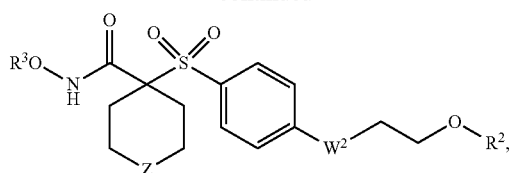
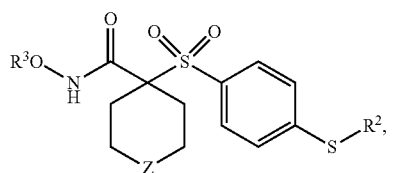
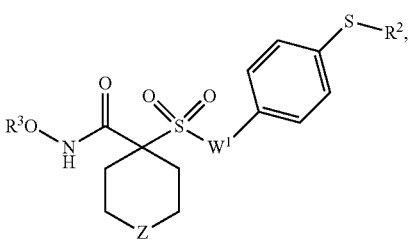
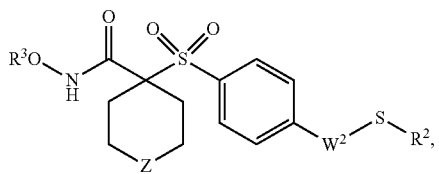
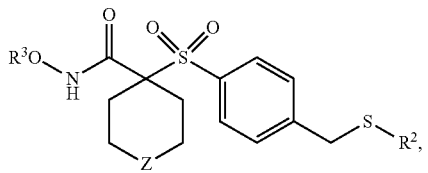
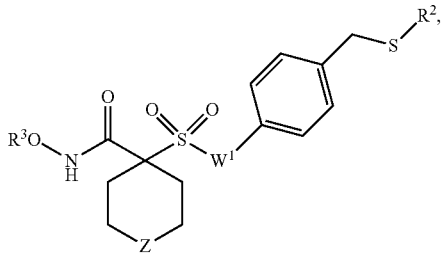
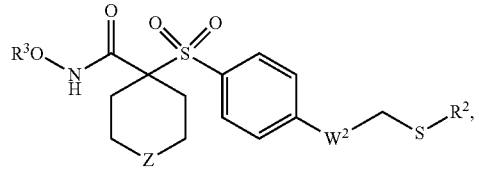
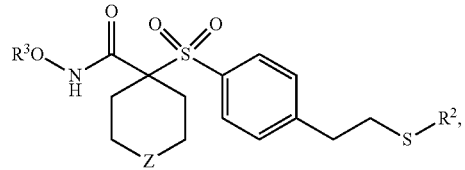

-continued

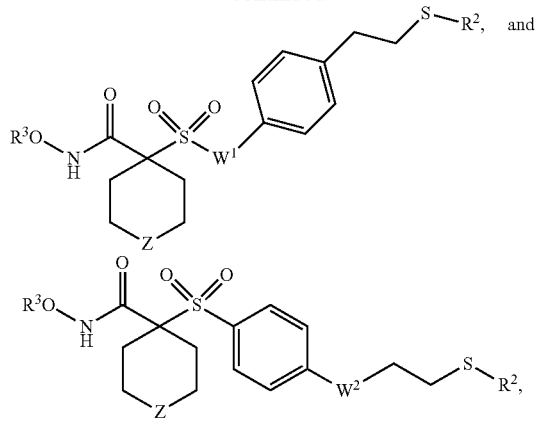

pharmaceutically acceptable salt thereof.

The following selections are envisioned for any of the formulas disclosed herein (e.g., I, Ia', Ia", Ib, II, IIa', IIa", IIb, III, IIIa', IIIa", IIIb, IV, IVa', IVa", or IVb). In some embodiments, at least one $R^3$ is H. In these embodiments, the compound of Formula (I) can have a structure:

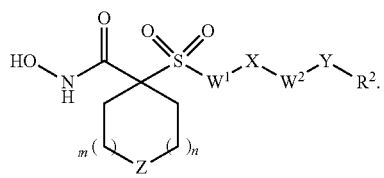

For example, the compound of Formula (I) can have a structure selected from the group consisting of:

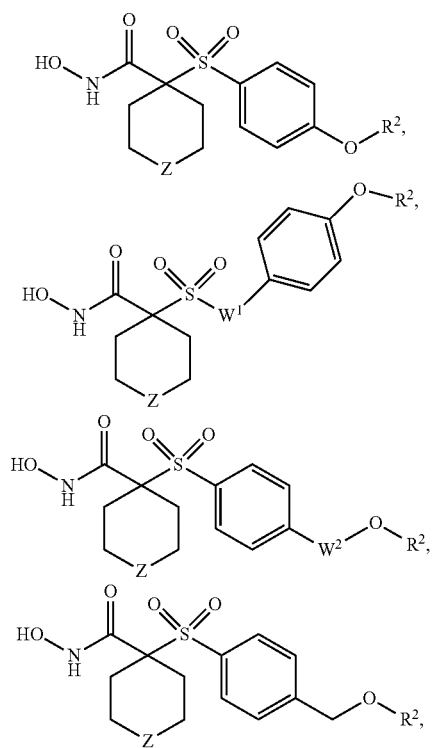

-continued

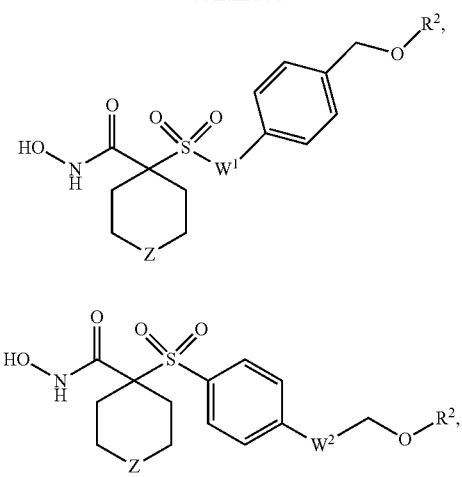

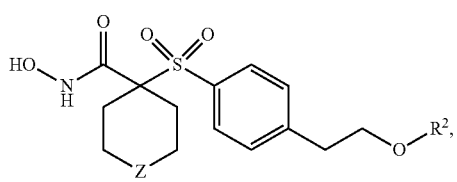

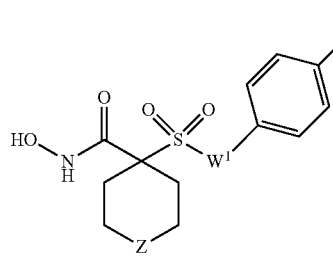

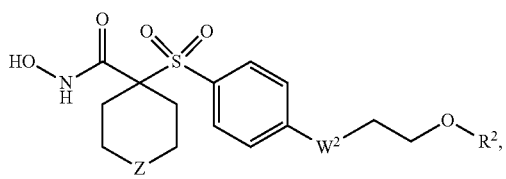

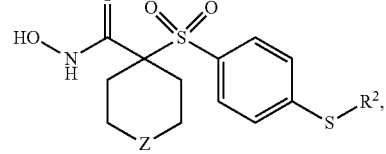

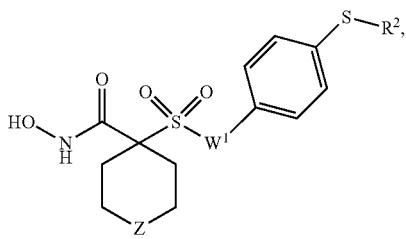

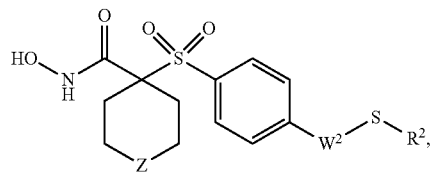

-continued

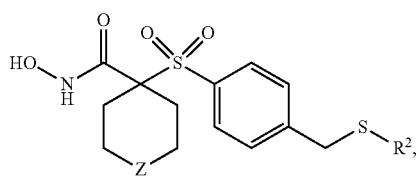

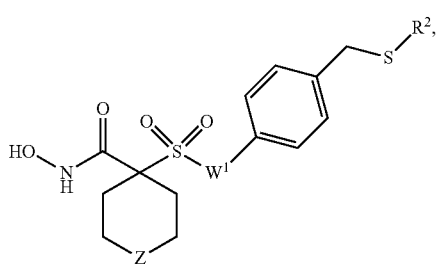

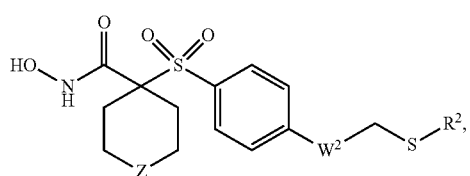

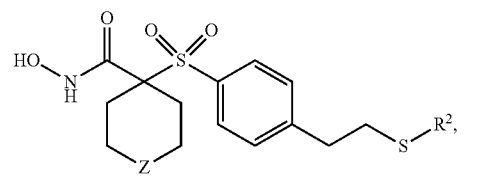

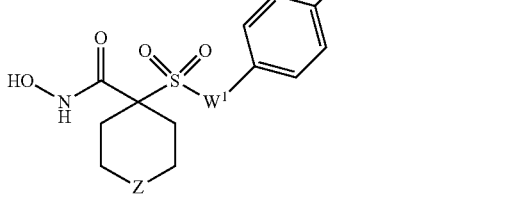

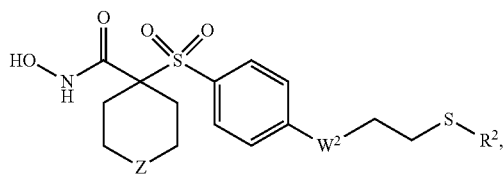

or a pharmaceutically acceptable salt thereof. In various embodiments, at least one $R^3$ is $C_{1-3}$alkyl, such as methyl, ethyl, propyl, or isopropyl. In some embodiments, the compound of Formula (I) can have a structure selected from the group consisting of:

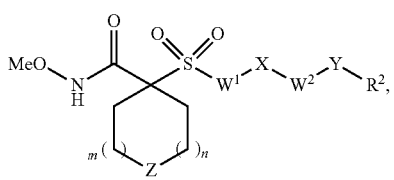

-continued

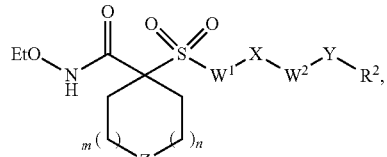

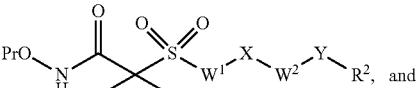

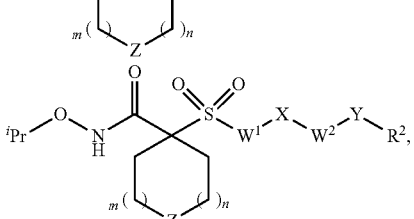

or a pharmaceutically acceptable salt thereof. In various cases, Y can be, for example, NMe-$C_{0-2}$alkylene, $C_{0-2}$alkylene-NMe, OC(=O)NMe, or NMeC=O.

The following selections are envisioned for any of the formulas disclosed herein (e.g., I, Ia', Ia", Ib, II, IIa', IIa", IIb, III, IIIa', IIIa", IIIb, IV, IVa', IVa", or IVb). In some embodiments, Z is $NR^1$ or $NSO_2R^1$ and $R^1$ is $C_{1-6}$alkylene-CB; $C_{0-4}$alkylene-CH($C_{1-6}$alkylene-CB)$_2$, $C_{0-4}$alkylene-C($C_{1-6}$alkylene-CB)$_3$, $C_{1-6}$alkylene-heteroaryl-$C_{0-6}$alkylene-CB, $C_{0-4}$alkylene-CH($C_{1-3}$alkylene-heteroaryl-$C_{0-6}$alkylene-CB)$_2$H, or $C_{0-4}$alkylene-C($C_{1-3}$alkylene-heteroaryl-$C_{0-6}$alkylene-CB)$_3$. In some cases, Z is $NR^1$. In some embodiments, $R^1$ is $C_{1-6}$ alkylene-CB. In various cases, $R^1$ is $CH_2$—CB, $CH_2CH_2$—CB, $CH_2CH_2CH_2$—CB, $CH_2CH_2CH_2CH_2$—CB, $CH_2CH_2CH_2CH_2CH_2$—CB, or $CH_2CH_2CH_2CH_2CH_2CH_2$—CB. In some cases, $R^1$ is $CH_2$—CB. In some embodiments, $R^1$ is $CH(CB)_2$ or $C_{0-4}$alkylene-CH($C_{1-6}$alkylene-CB)$_2$. Contemplated $R^1$ groups include $CH(CB)_2$ $CH(CH_2$—CB)$_2$, $CH(CH_2CH_2$—CB)$_2$, $CH(CH_2CH_2CH_2$—CB)$_2$, $CH(CH_2CH_2CH_2CH_2$—CB)$_2$, $CH_2CH(CH_2$—CB)$_2$, $CH_2CH(CH_2CH_2$—CB)$_2$, $CH_2CH(CH_2CH_2$—CB)$_2$, $CH_2CH(CH_2CH_2CH_2$—CB)$_2$, $CH_2CH(CH_2CH_2CH_2CH_2$—CB)$_2$, $CH_2CH_2CH_2CH_2$—CB)$_2$, $CH_2CH_2CH(CH_2$—CB)$_2$, $CH_2CH_2CH(CH_2CH_2$—CB)$_2$, $CH_2CH_2CH(CH_2CH_2CH_2$—CB)$_2$, $CH_2CH_2CH(CH_2CH_2CH_2CH_2$—CB)$_2$, or $CH_2CH_2CH(CH_2CH_2CH_2CH_2$—CB)$_2$. In some embodiments, $R^1$ is $CH(CB)_2$ $CH(CH_2$—CB)$_2$, or $CH(CH_2CH_2$—CB)$_2$. In some cases, $R^1$ is $C_{0-4}$alkylene-C($C_{1-6}$ alkylene-CB)$_3$. Contemplated $R^1$ groups include $C(CH_2$—CB)$_3$, $C(CH_2CH_2$—CB)$_3$, $C(CH_2CH_2CH_2$—CB)$_3$, $C(CH_2CH_2CH_2CH_2$—CB)$_2$, $CH_2C(CH_2$—CB)$_3$, $CH_2C(CH_2CH_2$—CB)$_3$, $CH_2C(CH_2CH_2CH_2$—CB)$_3$, $CH_2C(CH_2CH_2CH_2CH_2$—CB)$_3$, $CH_2CH_2C(CH_2$—CB)$_3$, $CH_2CH_2C(CH_2CH_2$—CB)$_3$, $CH_2CH_2C(CH_2CH_2CH_2$—CB)$_3$, or $CH_2CH_2C(CH_2CH_2CH_2CH_2$—CB)$_3$. In various embodiments, $R^1$ is $C(CH_2$—CB)$_3$, $C(CH_2CH_2$—CB)$_3$, or $C(CH_2CH_2CH_2$—CB)$_3$. In some embodiments, $R^1$ is $C_{1-6}$alkylene-heteroaryl-$C_{0-6}$alkylene-CB. Contemplated $R^1$ groups include $CH_2$-heteroaryl-CB, $CH_2CH_2$-heteroaryl-CB, $CH_2CH_2CH_2$-heteroaryl-CB, $CH_2CH_2CH_2CH_2$-heteroaryl-CB, $CH_2CH_2CH_2CH_2CH_2$-heteroaryl-CB, $CH_2CH_2CH_2CH_2CH_2CH_2$-heteroaryl-$CH_2$—CB, $CH_2$-heteroaryl-$CH_2$—CB, $CH_2$-heteroaryl-$CH_2$—CB, $CH_2CH_2$-heteroaryl-$CH_2$—CB, $CH_2$-heteroaryl-$CH_2CH_2$—CB, $CH_2CH_2$-heteroaryl-$CH_2CH_2$—CB, $CH_2CH_2CH_2$-heteroaryl- CH$_2$CH$_2$—CB, CH$_2$-heteroaryl-CH$_2$CH$_2$CH$_2$—CB, CH$_2$CH$_2$-heteroaryl-CH$_2$CH$_2$CH$_2$—CB, CH$_2$CH$_2$CH$_2$-heteroaryl-CH$_2$CH$_2$CH$_2$—CB, CH$_2$-heteroaryl-CH$_2$CH$_2$CH$_2$CH$_2$—CB, CH$_2$-heteroaryl-CH$_2$CH$_2$CH$_2$CH$_2$—CB, or CH$_2$CH$_2$CH$_2$-heteroaryl-CH$_2$CH$_2$CH$_2$CH$_2$—CB. In some embodiments, R$^1$ is CH$_2$-heteroaryl-CH$_2$CH$_2$—CB or CH$_2$-heteroaryl-CH$_2$CH$_2$CH$_2$—CB. In various embodiments, R$^1$ is CH$_2$-heteroaryl-CH$_2$CH$_2$CH$_2$—CB. In some cases, R$^1$ is C$_{0-4}$alkylene-CH(C$_{1-3}$alkylene-heteroaryl-C$_{0-6}$alkylene-CB)$_2$H. Contemplated R$^1$ groups include CH(CH$_2$-heteroaryl-CB)$_2$, CH(CH$_2$CH$_2$-heteroaryl-CB)$_2$, CH(CH$_2$CH$_2$CH$_2$-heteroaryl-CB)$_2$, CH(CH$_2$CH$_2$CH$_2$CH$_2$-heteroaryl-CB)$_2$, CH$_2$CH(CH$_2$-heteroaryl-CB)$_2$, CH$_2$CH(CH$_2$CH$_2$-heteroaryl-CB)$_2$, CH$_2$CH(CH$_2$CH$_2$CH$_2$-heteroaryl-CB)$_2$, CH$_2$CH(CH$_2$CH$_2$CH$_2$CH$_2$-heteroaryl-CB)$_2$, CH$_2$CH$_2$CH(CH$_2$-heteroaryl-CB)$_2$, CH$_2$CH$_2$CH(CH$_2$CH$_2$-heteroaryl-CB)$_2$, CH$_2$CH$_2$CH(CH$_2$CH$_2$-heteroaryl-CB)$_2$, CH$_2$CH$_2$CH(CH$_2$CH$_2$CH$_2$-heteroaryl-CB)$_2$, or CH$_2$CH$_2$CH(CH$_2$CH$_2$CH$_2$CH$_2$-heteroaryl-CB)$_2$. In some embodiments, R$^1$ is CH(CH$_2$-heteroaryl-CB)$_2$ or CH(CH$_2$CH$_2$-heteroaryl-CB)$_2$. In various cases, R$^1$ is CH(CH$_2$-heteroaryl-CB)$_2$ or C(CH$_2$-heteroaryl-CB)$_3$. In some embodiments, R$^1$ is C$_{0-4}$alkylene-C(C$_{1-3}$alkylene-heteroaryl-C$_{0-6}$alkylene-CB)$_3$. Contemplated R$^1$ groups can include C(CH$_2$-heteroaryl-CB)$_3$, C(CH$_2$CH$_2$-heteroaryl-CB)$_3$, C(CH$_2$CH$_2$CH$_2$-heteroaryl-CB)$_3$, C(CH$_2$CH$_2$CH$_2$CH$_2$-heteroaryl-CB)$_3$, CH$_2$C(CH$_2$-heteroaryl-CB)$_3$, CH$_2$C(CH$_2$CH$_2$-heteroaryl-CB)$_3$, CH$_2$C(CH$_2$CH$_2$CH$_2$-heteroaryl-CB)$_3$, CH$_2$C(CH$_2$CH$_2$CH$_2$CH$_2$-heteroaryl-CB)$_3$, CH$_2$CH$_2$C(CH$_2$-heteroaryl-CB)$_3$, CH$_2$CH$_2$C(CH$_2$CH$_2$-heteroaryl-CB)$_3$, CH$_2$CH$_2$C(CH$_2$CH$_2$CH$_2$-heteroaryl-CB)$_3$, or CH$_2$CH$_2$C(CH$_2$CH$_2$CH$_2$CH$_2$-heteroaryl-CB)$_3$. In some cases, R$^1$ is C(CH$_2$-heteroaryl-CB)$_3$ or C(CH$_2$CH$_2$-heteroaryl-CB)$_3$. Suitable heteroaryl groups for these embodiments can be those previously described for variable X. In some embodiments, the heteroaryl group can be triazolenyl. In some embodiments, Z has a structure selected from the group consisting of CH$_2$—CB, CH$_2$CH$_2$—CB, CH$_2$-triazolenyl-CH$_2$CH$_2$CH$_2$—CB, CH(CH$_2$-triazolenyl-CB)$_2$, and C(CH$_2$-triazolenyl-CB)$_3$.

The following selections are envisioned for any of the formulas disclosed herein (e.g., I, Ia', Ia'', Ib, II, IIa', IIa'', IIb, III, IIIa', IIIa'', IIIb, IV, IVa', IVa'', or IVb). In some embodiments, Z is NR$^1$ or NSO$_2$R$^1$ and R$^1$ is H, C$_{1-10}$alkyl, C$_{1-6}$alkynyl, C$_{1-6}$alkylene-OC$_{1-6}$ alkyl, C$_{1-6}$alkylene-SC$_{1-6}$ alkyl, C$_{1-6}$alkylene-Oaryl, C$_{1-6}$alkylene-Saryl, C$_{0-6}$alkylene-cycloalkyl, C$_{0-6}$alkylene-heterocycloalkyl, C$_{0-6}$alkylene-aryl, or C$_{0-6}$alkylene-heteroaryl. In some cases, R$^1$ is H. In various cases, R$^1$ is C$_{1-10}$alkyl (e.g., Me, Et, Pr, $^i$Pr) or C$_{1-6}$alkynyl (e.g., CH$_2$CCH). For example, R$^1$ can be Me or CH$_2$CCH. In various embodiments, R$^1$ is C$_{1-6}$ alkylene-OC$_{1-6}$alkyl or C$_{1-6}$alkylene-SC$_{1-6}$alkyl (e.g., CH$_2$CH$_2$OCH$_3$, CH$_2$CH$_2$CH$_2$OCH$_3$, CH$_2$OCH$_2$CH$_3$, CH$_2$CH$_2$OCH$_2$CH$_3$, CH$_2$CH$_2$CH$_2$OCH$_2$CH$_3$, CH$_2$SCH$_3$, CH$_2$CH$_2$SCH$_3$, CH$_2$CH$_2$CH$_2$SCH$_3$, CH$_2$SCH$_2$CH$_3$, CH$_2$CH$_2$SCH$_2$CH$_3$, or CH$_2$CH$_2$CH$_2$SCH$_2$CH$_3$). For example, R$^1$ can be CH$_2$CH$_2$OCH$_3$. In various embodiments, R$^1$ is C$_{1-6}$alkylene-Oaryl, C$_{1-6}$ alkylene-Saryl, C$_{0-6}$alkylene-aryl, or C$_{0-6}$alkylene-heteroaryl. Suitable aryl and heteroaryl groups have been previously described, such as in the context of variable X. In some embodiments, the aryl group is phenyl. In various embodiments, the heteroaryl group is pyrazolyl. In some embodiments, R$^1$ is C$_{0-6}$alkylene-cycloalkyl or C$_{0-6}$alkylene-heterocycloalkyl. Suitable cycloalkyl groups include, for example, cyclopropyl, cyclobutyl, cyclopentyl, and cyclohexyl. In some cases, the cycloalkyl group is cyclopropyl. Suitable heterocycloalkyl groups include, for example, pyrrolidinyl, piperdinyl, or pyrazolidinyl. In some cases, the heterocycloalkyl group is pyrrolidinyl or piperdinyl. For example, R$^1$ can be cyclopropyl or CH$_2$cyclopropyl.

The following selections are envisioned for any of the formulas disclosed herein (e.g., I, Ia', Ia'', Ib, II, IIa', IIa'', IIb, III, IIIa', IIIa'', IIIb, IV, IVa', IVa'', or IVb). In some cases, Z is O, S, C=O, SO, or SO$_2$. In some embodiments, Z is O. In various embodiments, Z is S. In various cases, Z is C=O. In some cases, Z is SO. In various embodiments Z is SO$_2$.

The following selections are envisioned for any of the formulas disclosed herein (e.g., I, Ia', Ia'', Ib, II, IIa', IIa'', IIb, III, IIIa', IIIa'', IIIb, IV, IVa', IVa'', or IVb). In some embodiments, R$^2$ is C$_{0-2}$alkylene-aryl-R$^4$, C$_{0-2}$alkylene-heteroaryl-R$^4$, C$_{0-2}$alkylene-cycloalkyl-R$^4$, or C$_{0-2}$alkylene-heterocycloalkyl-R$^4$. In some cases, R$^2$ is C$_{0-2}$alkylene-aryl-R$^4$. Suitable aryl groups have been previously described herein for variable X. In some embodiments, the aryl group is phenyleneyl. In various cases, R$^2$ is C$_{0-2}$alkylene-heteroaryl-R$^4$. Suitable heteroaryl group have been previously described herein for variable X. In some cases, the heteroaryl group is pyrrazolyl, pyridylenyl, imidazolylenyl, thiazolylenyl, furanylenyl, thiofuranylenyl, quinolinylenyl, isoquinolinylenyl, benzoxazolylenyl, benzimidazolylenyl, or benzothiazolylenyl. In various cases, the heteroaryl group is pyrrazolyl or pyridylenyl. In some embodiments, R$^2$ is C$_{0-2}$alkylene-cycloalkyl-R$^4$. Suitable cycloalkyl groups include, for example, cyclopropyl, cyclobutyl, cyclopentyl, and cyclohexyl. In some cases, the cycloalkyl group is cyclopentyl, cyclohexyl, or tetrahydropyranyl. In various cases, the cycloalkyl group is cyclopentyl. In some cases, R$^2$ is or C$_{0-2}$alkylene-heterocycloalkyl-R$^4$. Suitable heterocycloalkyl groups include, for example, pyrrolidinylenyl, piperdinylenyl, pyrazolidinenyl, tetrahydrofuranenyl, tetrahydropyranenyl, dihydrofuranenyl, morpholinenyl, and thiophenenyl. In some cases, the heterocycloalkyl group is pyrrolidinylenyl or piperdinylenyl. In various cases, the heterocycloalkyl group is pyrrolidinylenyl.

The following selections are envisioned for any of the formulas disclosed herein (e.g., I, Ia', Ia'', Ib, II, IIa', IIa'', IIb, III, IIIa', IIIa'', IIIb, IV, IVa', IVa'', or IVb). In some embodiments, R$^4$ is H. In some cases, R$^4$ is halo (e.g., Br, Cl, or F). In various embodiments, R$^4$ is C$_{1-10}$alkyl (e.g., Me, Et, Pr, or $^i$Pr) or C$_{1-10}$alkenyl. The alkyl or alkenyl group can be unsubstituted or substituted, such as with fluorine (e.g., CF$_3$ or CF$_2$CF$_3$). In some embodiments, R$^4$ is CF$_3$. In various cases, R$^4$ is C$_{0-6}$alkylene-cycloalkyl. In these embodiments, the cycloalkyl group can include, for example, cyclopropyl, cyclobutyl, cyclopentyl, and cyclohexyl. In some cases, the cycloalkyl group is cyclopropyl. In some embodiments, R$^4$ is C$_{0-6}$alkylene-aryl or C$_{0-6}$alkylene-heteroaryl. Suitable aryl groups have been described previously herein, such as in the context of R$^2$ (e.g., phenyl or naphthyl). In some embodiments, the aryl group is phenyl. For example, R$^4$ can include Ph, CH$_2$Ph, CH$_2$CH$_2$Ph, naphthyl, and CH$_2$naphthyl. Suitable heteroaryl groups have been described previously herein, such as in the context of variable X (e.g., pyridinyl, imidazolyl, and triazolyl). In some embodiments, the heteroaryl group is pyridinyl. In various cases, R$^4$ is C$_{0-6}$alkylene-OC$_{1-6}$alkyl or C$_{0-6}$alkylene-SC$_{1-6}$alkyl. For example, R$^4$ can be OCH$_3$, OCH$_2$CH$_3$, CH$_2$CH$_2$OCH$_3$, OCF$_3$, OCH$_2$CF$_3$, OCF$_2$CF$_3$, SCH$_3$, CH$_2$SCH$_3$, CH$_2$CH$_2$SCH$_3$, SCF$_3$, SCH$_2$CF$_3$, or SCF$_2$CF$_3$. In some cases, R$^4$ is OCH$_3$, OCH$_2$CH$_3$, CH$_2$OCH$_3$, CH$_2$CH$_2$OCH$_3$, OCF$_3$, OCH$_2$CF$_3$, or OCF$_2$CF$_3$. In various cases, R$^4$ is OCH$_3$ OCF$_3$, OCF$_2$CF$_3$, or SCF$_3$. In various cases, $R^4$ is $OCF_3$. In some embodiments, $R^4$ is $C_{0-6}$alkylene-Oaryl, or $C_{0-6}$alkylene-Saryl. Suitable aryl groups have been previously described for $R^4$. For example, $R^4$ can be OPh, $CH_2$OPh, SPh, or $CH_2$SPh. For example, $R^4$ can be selected from the group consisting of H, Br, Cl, F, Me, Et, Pr, $CF_3$, $CF_2CF_3$, $CH(CF_3)_2$, cyclopropyl, $CH_2$Ph, $OCH_3$, $OCH_2CH_3$, $CH_2OCH_3$, $CH_2CH_2OCH_3$, $OCF_3$, $OCH_2CF_3$, $OCF_2CF_3$, OPh, and $CH_2$OPh.

The following selections are envisioned for any of the formulas disclosed herein (e.g., I, Ia', Ia", Ib, II, IIa', IIa", IIb, III, IIIa', IIIa", IIIb, IV, IVa', IVa", or IVb). In some cases, $R^2$ is $C_{0-6}$alkylene-CB, $C_{1-6}$alkylene-aryl-$C_{0-3}$alkylene-CB, or $C_{1-6}$alkylene-heteroaryl-$C_{1-6}$ alkylene-CB. In some cases, $R^2$ is $C_{0-6}$alkylene-CB. For example, $R^2$ can be CB, $CH_2$—CB, $CH_2CH_2$—CB, $CH_2CH_2CH_2$—CB, $CH_2CH_2CH_2CH_2$—CB, $CH_2CH_2CH_2CH_2CH_2$—CB, or $CH_2CH_2CH_2CH_2CH_2CH_2$—CB. In some embodiments, $R^2$ is CB, $CH_2$—CB, $CH_2CH_2$—CB. In various embodiments, $R^2$ is $CH_2$—CB, In various cases, $R^2$ is $C_{1-6}$alkylene-aryl-CB. Suitable aryl groups have been previously described in the context of $R^1$. In some embodiments, the aryl group is phenyleneyl or naphthaleneyl. For example, $R^2$ can be Ph-CB or $CH_2$-Ph-CB. In some cases, $R^2$ is $C_{1-6}$alkylene-heteroaryl-$C_{1-6}$alkylene-CB. Suitable heteroaryl groups for these embodiments can be those previously described in the context of $R^1$. In some embodiments, the heteroaryl group can be triazolenyl. For example, $R^2$ can be $CH_2$-triazolenyl-CH—CB, $CH_2$-triazolenyl-$CH_2CH_2$—CB or $CH_2$-triazolenyl-$CH_2CH_2CH_2$—CB. In some embodiments, $R^2$ has a structure selected from the group consisting of CB, $CH_2$—CB, $CH_2CH_2$—CB and $CH_2$-triazolenyl-$CH_2CH_2CH_2$—CB.

The term "CB" can be any carborane (i.e., a polyhedron cluster composed of boron, carbon and hydrogen atoms) known to one skilled in the art. The carborane can be closo-, nido-, arachno-, or hypho-carboranes. For example, the carborane can be a closo-carborane or nido-carborane. In some cases, the carborane can be a closo-carborane. In various embodiments, the carborane can be a nido-carborane. Further, the carborne may be an ortho-carborane, meta-carborane, or para-carborane. Any depiction of an inhibitor or agent described herein is exemplary and is intended to include all carborane regioisomers. In some embodiments, the carborane is ortho. In some embodiments, the carborane is meta. In some cases, CB is unsubstituted. In various cases, CB is substituted. In some embodiments, CB is substituted with a fluoroalkyl group, such as $CF_3$. As used herein, a carborane can be depicted as

which can represent any regioisomer (e.g., ortho, meta, or para) of any type of carborane (closo-, nido-, arachno-, or hypho-carborane).

The following selections are envisioned for any of the formulas disclosed herein (e.g., I, Ia', Ia", Ib, II, IIa', IIa", IIb, III, IIIa', IIIa", IIIb, IV, IVa', IVa", or IVb). In some embodiments, the MMP inhibitors and agents described herein include one or more fluorine ($^{19}$F) atoms. The $^{19}$F atom allows the inhibitor and/or agent to be detected in tumors using magnetic resonance spectroscopy, which demonstrates that the inhibitor and/or agent has localized to the desired target tissue. Klomp et. al., *Magnetic Resonance Med.* 50(2):303-8 (2003).

In some cases, the carborane species is conjugated to a known MMP inhibitor, such as an MMP inhibitor described in, for example, U.S. Pat. No. 6,750,228, U.S. Patent Application Publication No. 2003/0073718, and PCT Publication Nos. 2000/046221, 2000/050396, 2000/069821, and 2004/091549, each of which is incorporated by reference. In these embodiments, the carborane species is conjugated to either the nitrogen of the piperidine ring or to the side chain of MMP species, similarly as described for the compounds of Formula (I).

Because the piperidine-N-substituent is directed into solvent and is outside of the enzyme active site, very large groups may be placed in this position without a significant loss of potency. Freskos et al., *Bioorg Med Chem Lett* 23:5566-5570 (2013). Thus one, two, or three carborane clusters can be appended from the piperidine nitrogen enabling formation of potent MMP ligands that contain a large density of boron atoms, which makes them highly suitable for BNCT. Further, because a carborane is lipophilic and has comparable dimensions to a phenyl ring (Grimes, *J. Chem. Educ.*, 81(5):657 (2004)), it can occupy the P1' pocket of MMP.

Examples of the compound of Formula (I) include, but are not limited to:

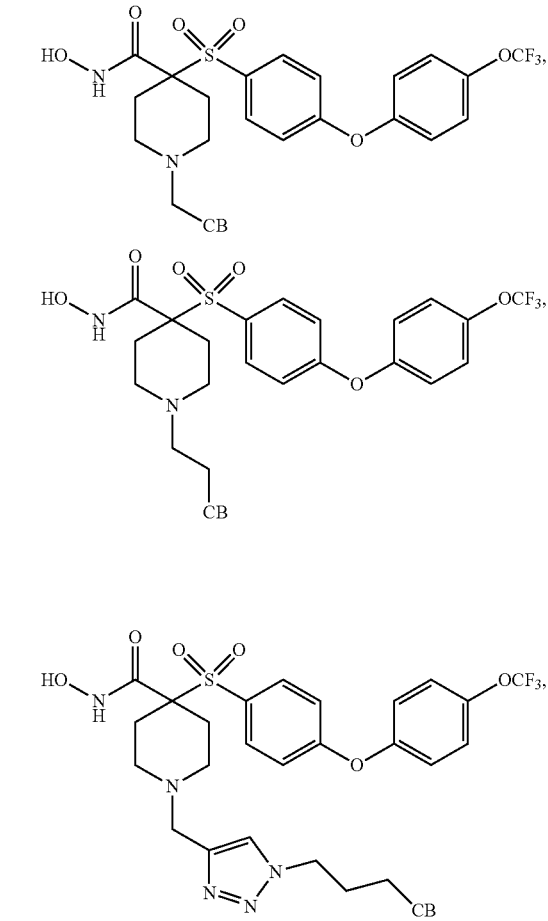

25
-continued
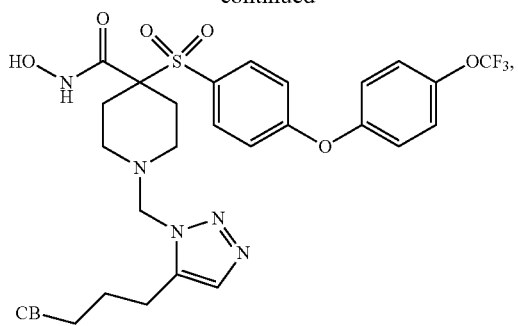
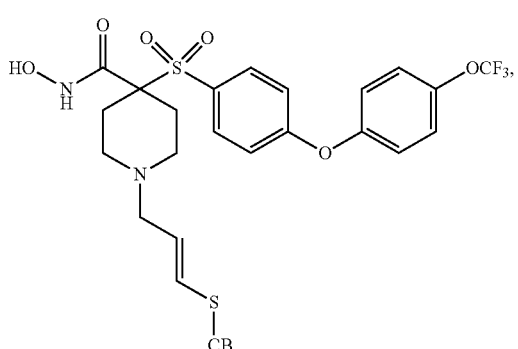
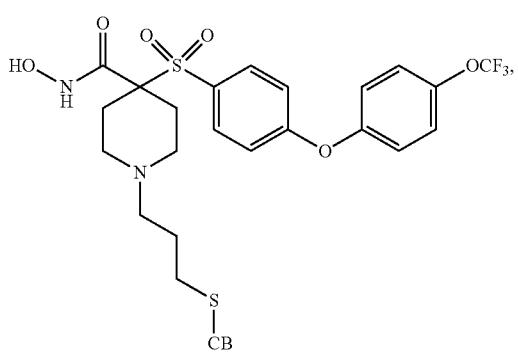
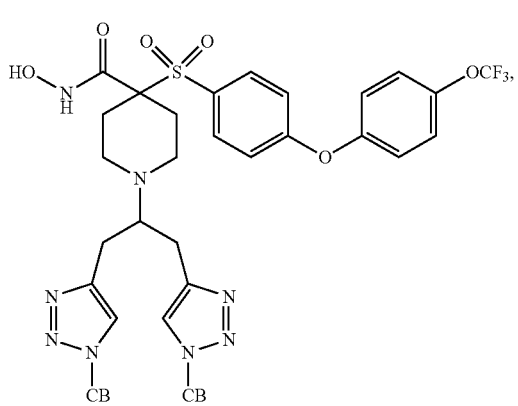
26
-continued
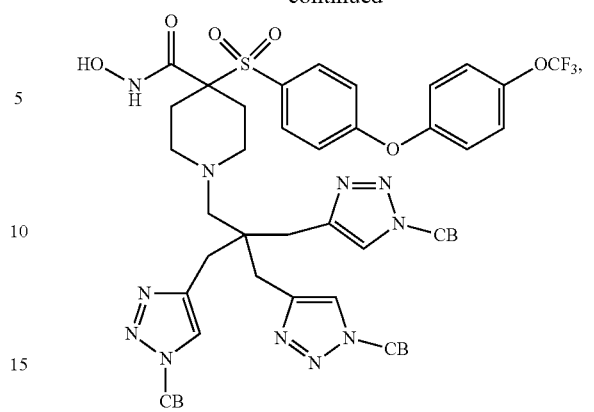
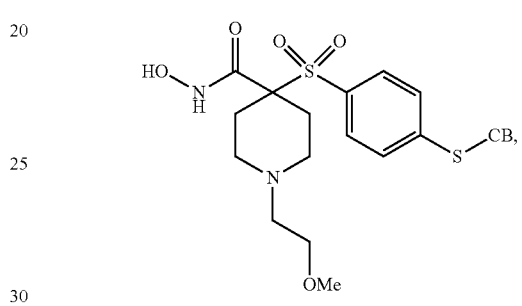
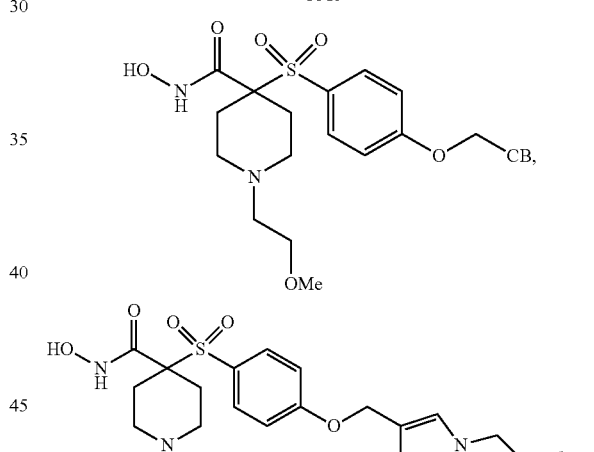
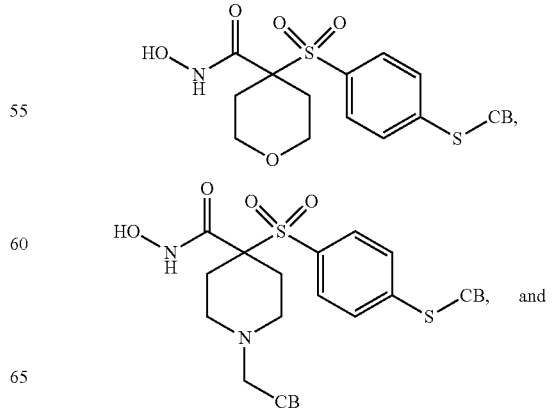
and

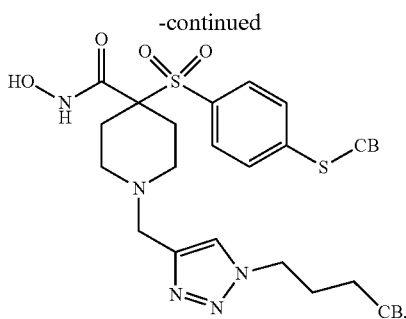

or pharmaceutically acceptable salts thereof.

In some cases, the compounds described herein (e.g., the compounds of Formulae Ia', Ia", Ib, II, IIa', IIa", IIb, III, IIIa', IIIa", IIIb, IV, IVa', IVa", or IVb or pharmaceutically acceptable salts thereof) inhibit or act at MMP with an $IC_{50}$ of about 1000 nM or less. In some embodiments, the compounds described herein (e.g., the compounds of Formulae Ia', Ia", Ib, II, IIa', IIa", IIb, III, IIIa', IIIa", IIIb, IV, IVa', IVa", or IVb or pharmaceutically acceptable salts thereof) have an $IC_{50}$ value for MMP of less than about 100 nM, or less than about 10 nM, or less than about 1 nM. In various cases, the $IC_{50}$ value of the compounds described herein (e.g., the compounds of Formulae Ia', Ia", Ib, II, IIa', IIa", IIb, III, IIIa', IIIa", IIIb, IV, IVa', IVa", or IVb or pharmaceutically acceptable salts thereof) is about 1 nM to about 100 nM, or about 0.1 nM to about 1 μM.

Preparation of the Carborane Hydroxamic Acid MMP Inhibitors and Agents

Compounds of the present disclosure can be prepared by any method known to one skilled in the art. In embodiments wherein a piperidine is an intermediate, isolation of the compounds can be accomplished through crystallization of a salt, such as a hydrochloride salt.

In some embodiments, the compounds are prepared using a nucleophilic substitution reaction. For example, an alkyne-substituted MMP inhibitor or agent can be reacted with a cyano-substituted carborane (e.g., $B_{10}H_{12}(CH_3CN)_2$), as described by Giovenzana et al., *Tetrahedron* 55(49):14123 (1999), and shown in the scheme, below.

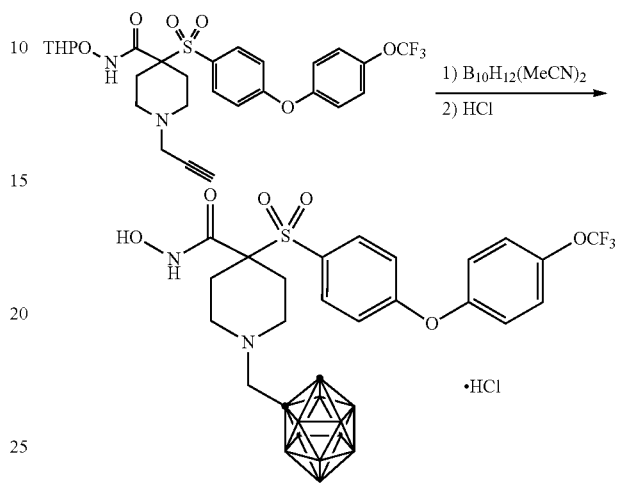

In some cases, the compounds are prepared using a [3+2] "Click" cycloaddition reaction. For example, an alkyne-substituted MMP inhibitor or agent can be reacted with an azido-substituted carborane (see, e.g., Matuszewski et al., *New J Chem* 39:1202-1221 (2015); Dash et al., *Organometallics*, 31(7):2931-2935 (2012)), followed by acidic deprotection of the THP ether to afford the carborane-bearing hydroxamates MMP inhibitor ligand as the HCl salt, as shown in the scheme below.

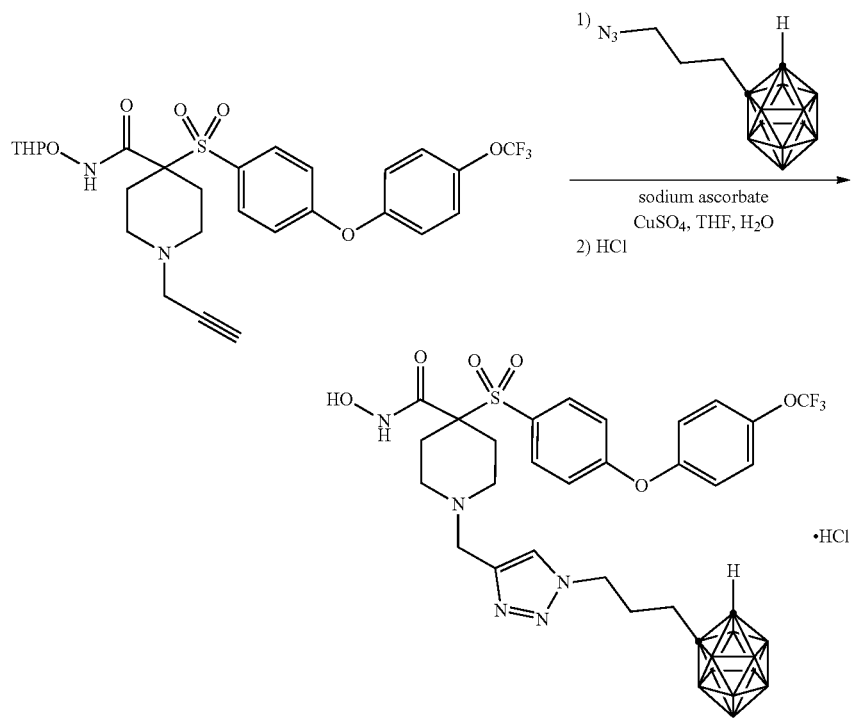

The piperidine-N-substituent is directed into solvent and is outside of the enzyme active site. Therefore, very large groups may be placed in this position without a significant loss of potency. Freskos et al., *Bioorg Med Chem Lett* 23:5566-5570 (2013). Thus one, two, or three carborane clusters can be appended from the piperidine nitrogen enabling formation of potent MMP ligands that contain a large density of boron atoms, which makes them highly suitable for BNCT. These di- and tri-substituted inhibitors and agents can be prepared using a di- or triyne piperidine substituent as a starting material, as shown in the schemes, below. For example, a diyne piperidine substituent can be derived from commercially available hept-1,6-diyne-4-ol, which is converted to the corresponding bromide via reaction with phosphorus tribromide to alkylate the piperidine-NH precursor.

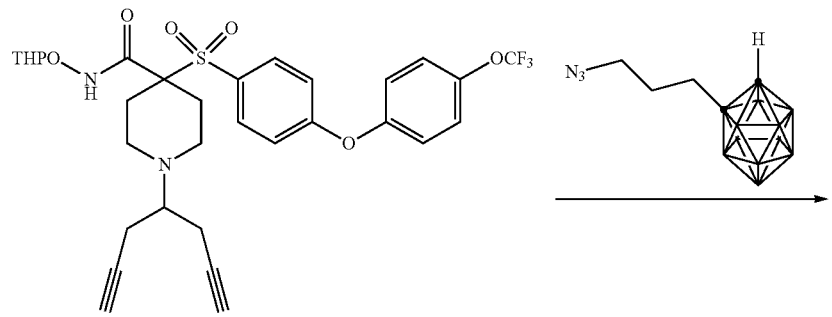

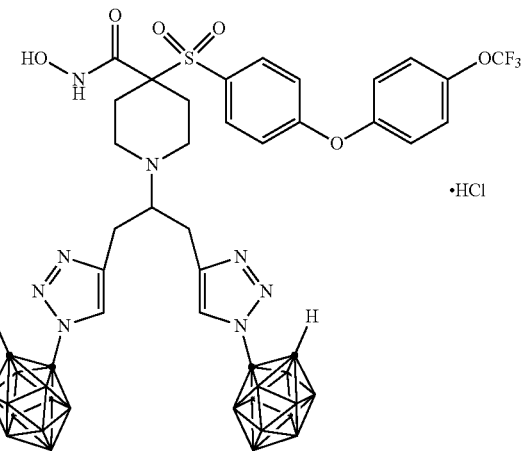

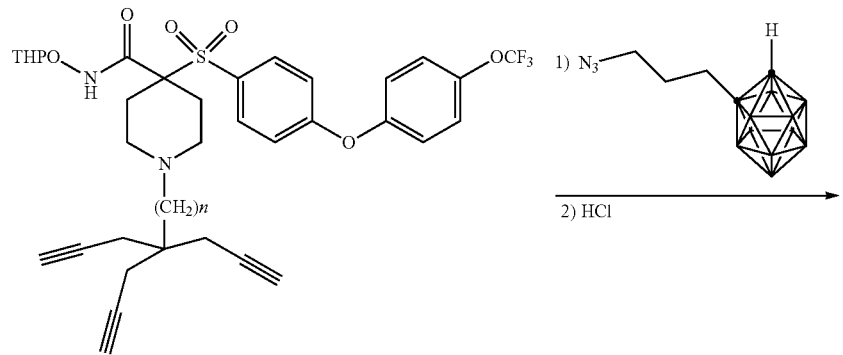

-continued

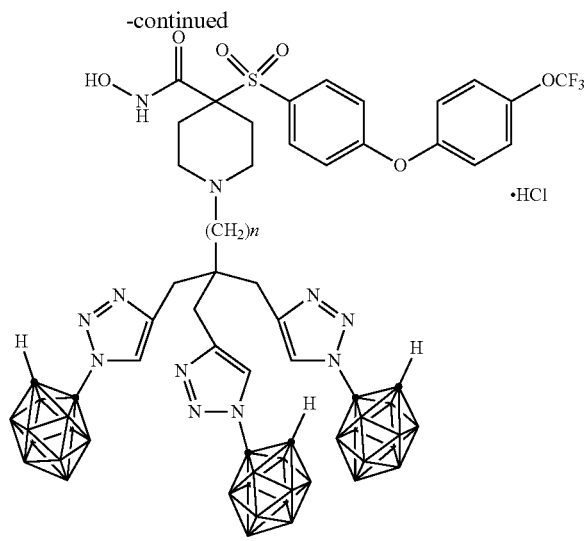

A carborane is lipophilic and has comparable dimensions to a phenyl ring (Grimes, *J. Chem. Educ.,* 81(5):657 (2004)). Therefore, the distal phenyl ring of the MMP inhibitor or agent that occupies the P1' pocket may be replaced with a carborane. These types of compounds are available through nucleophilic aromatic substitution reaction on the THP-protected N-methoxyethyl piperidine 4-fluorosulfone (see, e.g., U.S. Pat. Appl. Publ. No. 2003/0073718, which is incorporated herein by reference) with a carborane bearing a thiol or hydroxyl group, as exemplified by reaction with m-carborane-1-thiol and m-carborane-9-thiol, shown in the scheme below.

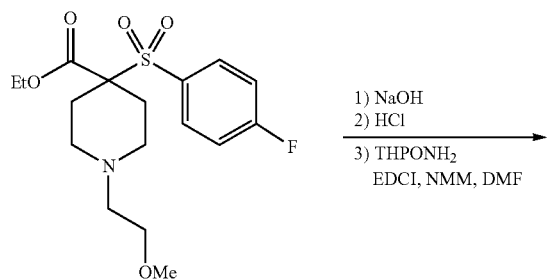

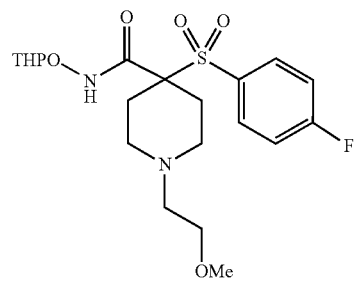

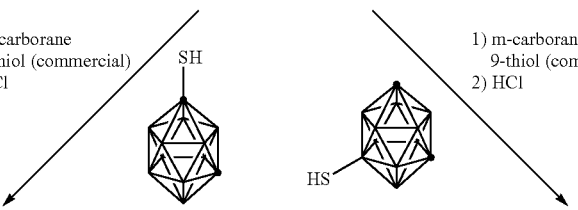

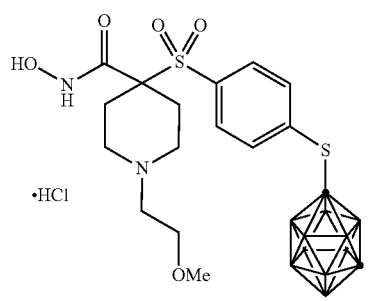
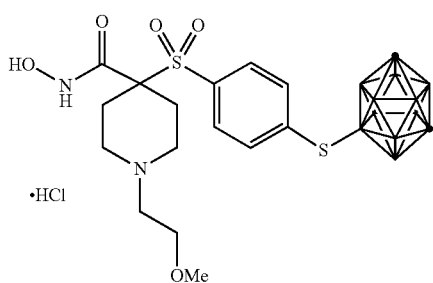

The inhibitors and agents described herein also can be prepared via nucleophilic aromatic substitution of the THP-protected 4-fluorophenylsulfone with an alkyne-bearing alcohol, such as propargyl alcohol, followed by reaction with $B_{10}H_{12}(CH_3CN)_2$ to append the carborane, or by reaction of the intermediate alkyne with the azidopropyl-orthocarborane to place the carborane moiety in the P1' region, as shown in the scheme below.

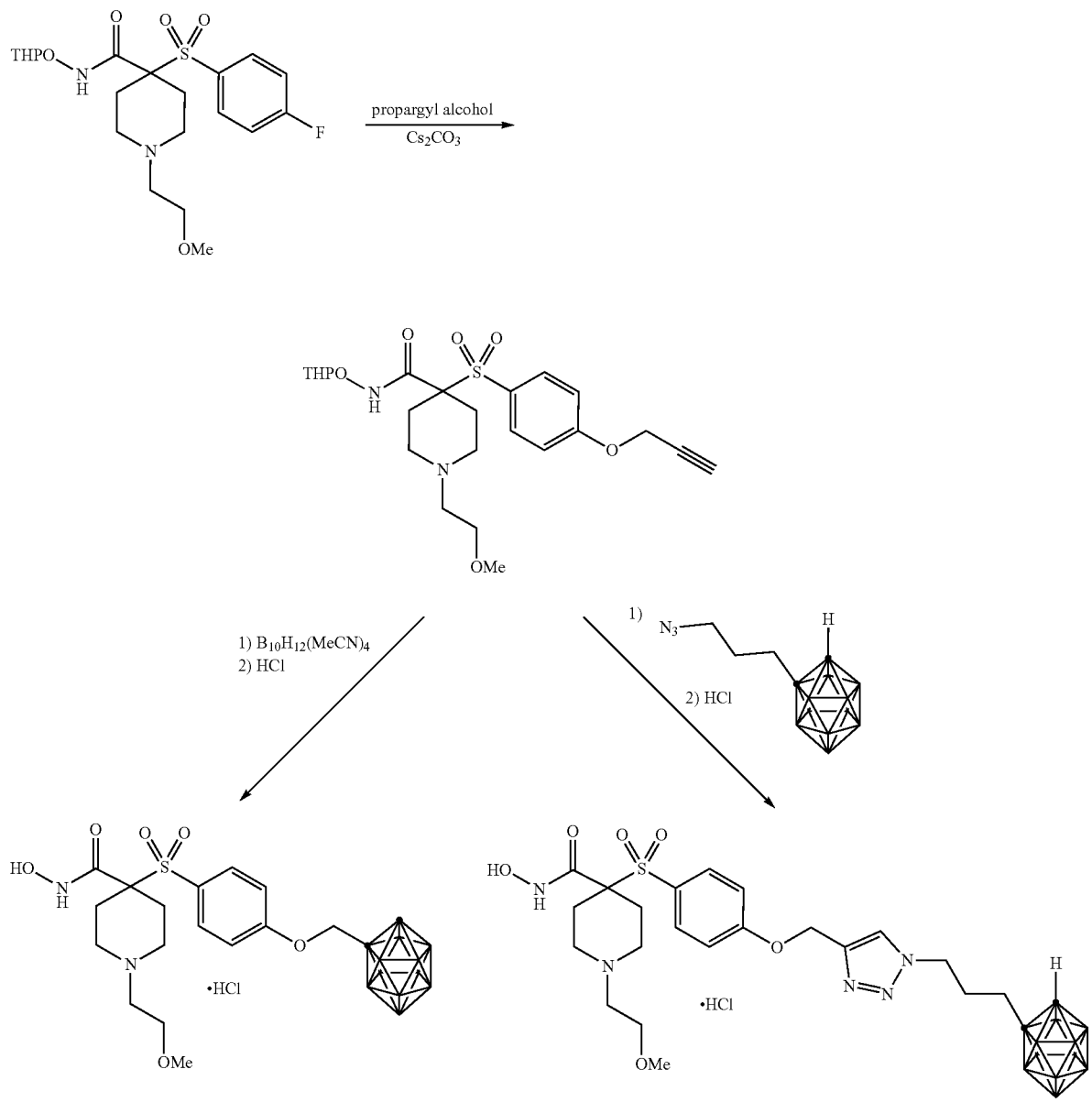

Complementary, neutral (uncharged) tetrahydropyran hydroxamates can be obtained from 4-((4-fluorophenyl)sulfonyl)-N-((tetrahydro-2H-pyran-2-yl)oxy)tetrahydro-2H-pyran-4-carboxamide (see Becker et al., *Med. Chem.* 48:6713-6730 (2005)) through nucleophilic aromatic substitution reaction with a carborane bearing a thiol moiety or hydroxy functionality, as exemplified by reaction with m-carborane-1-thiol and m-carborane-9-thiol in the scheme, below.

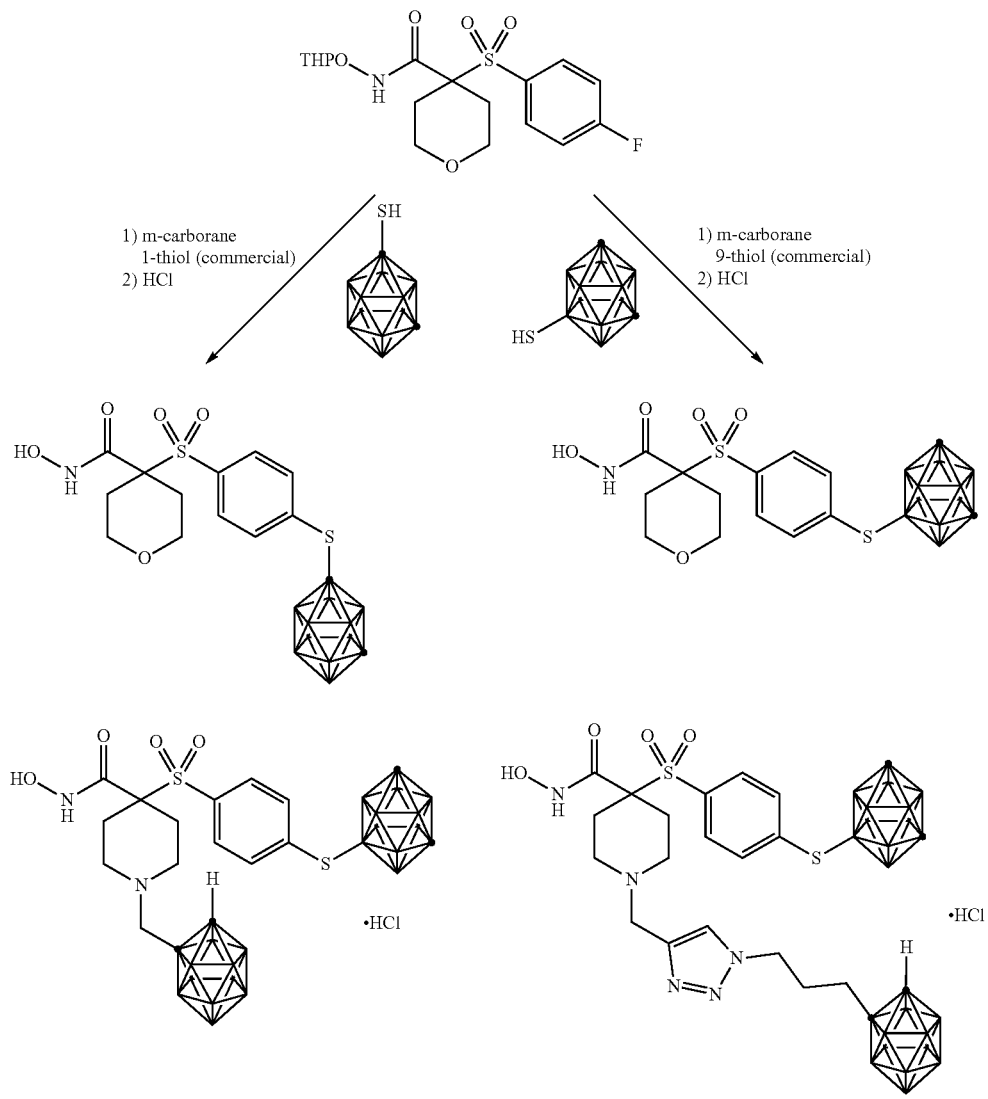

Improved Synthetic Route to 9

One synthetic route to the compounds described herein is based on the literature preparation of known intermediate 9. See Becker et al., J. Med. Chem. 2005, 48, 6713-6730; Becker, J. Med. Chem. 2010, 53, 6653-6680]. The synthetic route was improved during process development. The alkyne was selected as a key linking moiety, based on the fact that decaborane can react to produce carboranyl derivatives. Alkynes can also be used in Click chemistry to produce triazole-carboranyl derivatives, and thiols can be added to alkynes. The improved preparation of 9 is illustrated in Scheme 1.

Scheme 1

Step 1

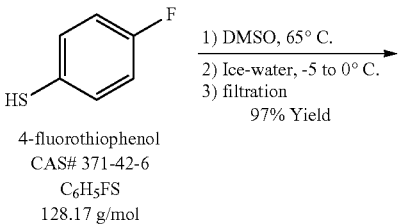

4-fluorothiophenol
CAS# 371-42-6
C₆H₅FS
128.17 g/mol

1) DMSO, 65° C.
2) Ice-water, -5 to 0° C.
3) filtration
97% Yield

37
-continued

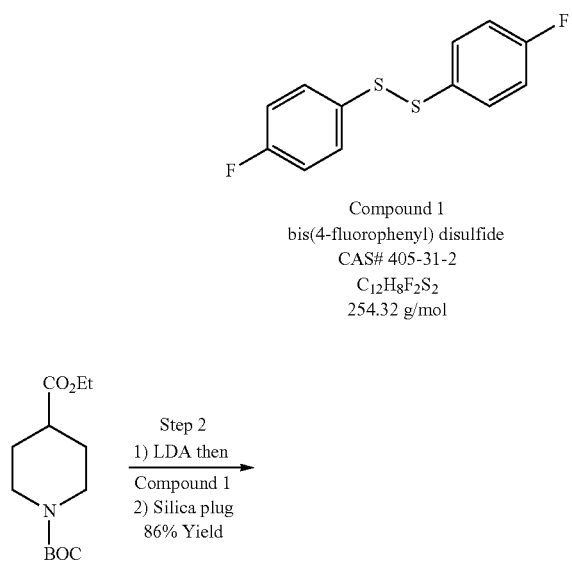

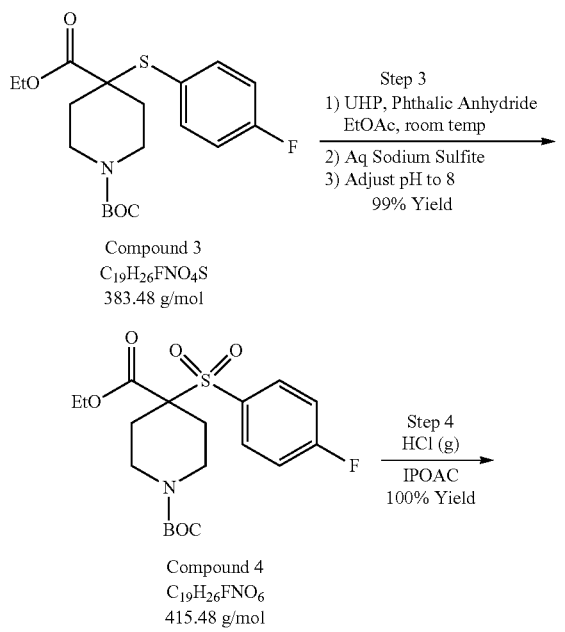

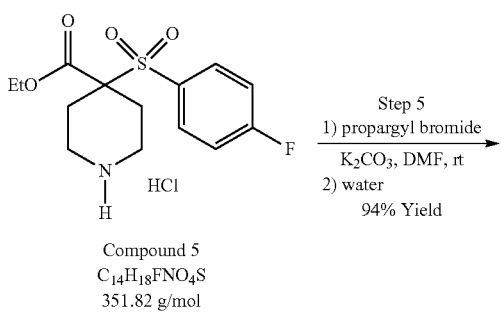

38
-continued

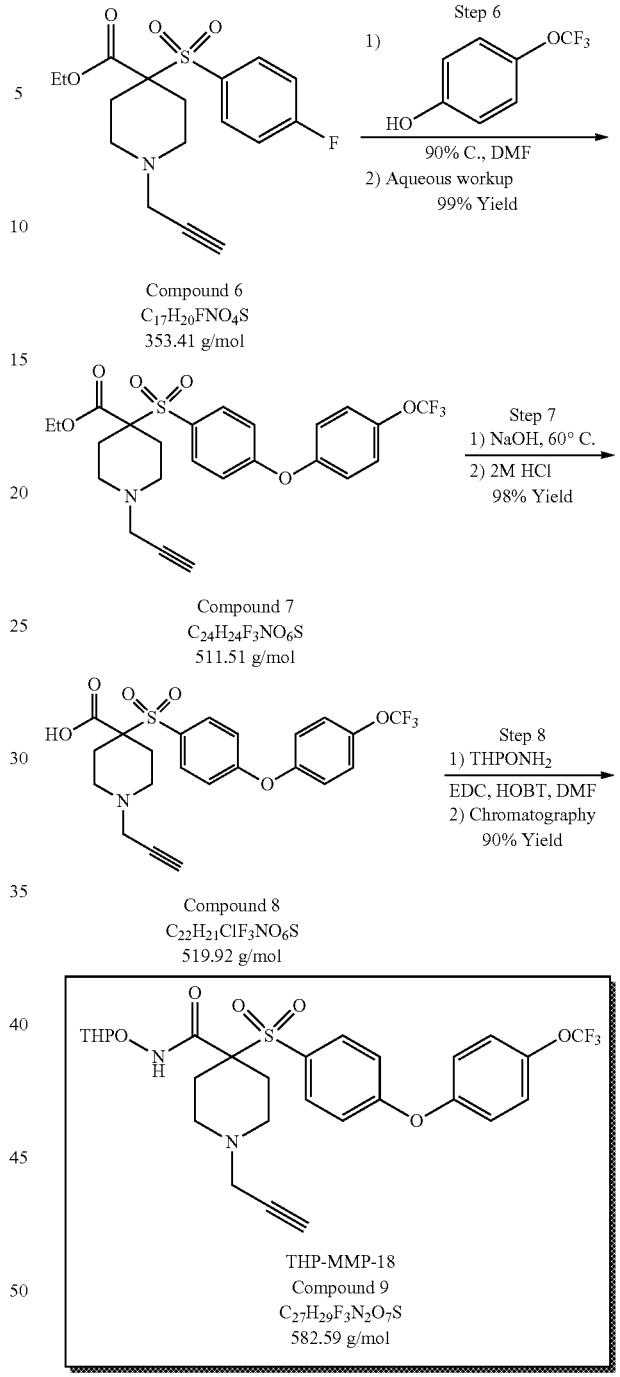

As shown in Scheme 1, the synthesis commences with the reaction of inexpensive and commercially available ethyl N-Boc-piperidine-4-carboxylate (2) with n-butyl lithium under cryogenic conditions to produce the enolate anion that subsequently reacts with disulfide (1) to produce the sulfide adduct (3). The preparation of disulfide (1) was achieved by the reaction of 4-fluorothiophenol in DMSO. It is noteworthy that the process and yield of the disulfide (1) was drastically improved by isolating the disulfide at 0-5° C., providing crystalline material as a low melting solid. The corresponding sulfide adduct (2) was originally oxidized to the sulfone (3) using MCPBA and required chromatographic purification. However, the process for oxidation of the sulfide to the sulfone was significantly improved with the use of the newly-developed, safe and efficient, scalable, and cost-efficient urea hydrogen peroxide (UHP)/phthalic anhydride system in ethyl acetate which allowed this oxidation to be easily carried out on a 180 g scale, and enabled facile isolation of highly pure sulfone via an extractive workup that did not require chromatography. See Lutz et al., *Synthesis* 50(11):2231-2234 (2018). The corresponding N-Boc sulfone 4 was reacted with hydrogen chloride gas in isopropyl acetate to cleave the Boc protecting group producing the piperidine as the hydrochloride salt 5, which was then alkylated with propargyl bromide and potassium carbonate in DMF to cleanly produce the propargylamine adduct 6 in high yield. SNAr reaction of propargylamine 6 with 4-(trifluoromethoxy)phenol and potassium carbonate in DMF cleanly produced the diphenyl ether adduct 7 in high yield. Alkaline hydrolysis of diphenyl ether (7) in ethanol used an excess (10 equiv. of NaOH) of hydroxide and overnight heating to achieve at least 90% conversion of ester to carboxylic acid 8. Lastly, the reaction of carboxylic acid (8) with O-(tetrahydro-2H-pyran-2-yl)hydroxylamine using EDC, HOBt and DIPEA in DMF afforded pure compound 9 after purification via normal phase chromatography. During the development of step 2, it was observed that the sulfone 3 can also be directly accessed by reaction of enolate with 4-fluorophenyl sulfonyl chloride as shown below (Scheme 2).

Scheme 2: Enolate and Sulfonyl chloride to produce Sulfone Adduct 4

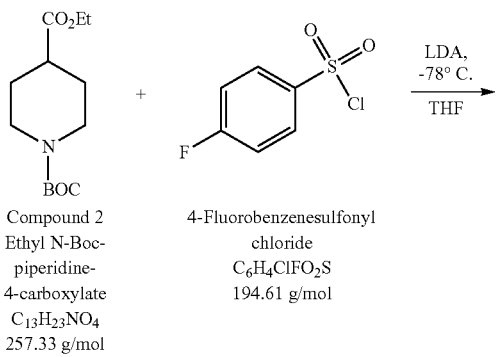

Compound 2
Ethyl N-Boc-
piperidine-
4-carboxylate
$C_{13}H_{23}NO_4$
257.33 g/mol 4-Fluorobenzenesulfonyl
chloride
$C_6H_4ClFO_2S$
194.61 g/mol

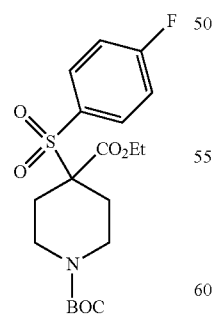

Compound 4
Sulfone Adduct
$C_{19}H_{26}FNO_6S$
415.48 g/mol

Borane-Alkyne Reactions and Synthesis of the 1,2-C2B10 Carborane Cluster

Reactions involving alkynes and decaborane have been a useful method of covalently attaching boron clusters to carrier molecules for a wide range of chemical fields including electronics, nanomaterials, and medicine. See Giovenzana, et. al. *Tetrahedron* 1999, 55, 14123-14136. There are a variety of methods for carrying out this transformation to prepare ortho-closo-carboranes. The classical method requires the formation of activated decaborane complex, $B_{10}H_{12}(MeCN)_2$, which can be prepared in situ or can be isolated and stored at ambient temperature for some time. The reagent $B_{10}H_{12}(MeCN)_2$ is typically prepared in toluene and acetonitrile (typically in excess) and the generated $B_{10}H_{12}(MeCN)_2$ complex can be isolated as a solid with a moderate shelf-life when stored under an inert atmosphere. Alternatively, the $B_{10}H_{12}(MeCN)_2$ complex can be prepared in situ for direct carborane synthesis. Preparation of the $B_{10}H_{12}(MeCN)_2$ complex is typically performed at 80-120° C. for at least 1 hour. Subsequent reaction of $B_{10}H_{12}(MeCN)_2$ and an alkyne at 80-120° C. affords the closo-carboranyl derivative, usually involving overnight heating to fully consume the alkyne starting material. However, the reaction can be accelerated when a catalytic amount of silver nitrate is added, reducing the reaction time to 1-4 hours. See Toppino et al. *Inorg. Chem.*, 2013, 52, 15, 8743-8749. In addition, direct reaction of alkynes with decaborane can be carried out efficiently using ionic liquids as the solvent/activator, and this process does not require the use of a Lewis base to form a $B_{10}H_{12}$(Lewis base)$_2$ complex. The use of the ionic liquid also allows very short reactions at 100-120° C. to achieve reaction completion which makes this process amenable for flow chemistry since it is a fast reaction, and the toxic decaborane can be more safely handled.

The reaction of 9 and $B_{10}H_{12}(MeCN)_2$ can serve as a convenient pathway to prepare and isolate carboranyl targets for BNCT (Scheme 3). Conditions that were evaluated included temperature, solvent, prior preparation of the $B_{10}H_{12}(MeCN)_2$ complex, in situ generation of the $B_{10}H_{12}(MeCN)_2$ complex, stoichiometry of $B_{10}H_{12}(MeCN)_2$, and catalytic addition of silver nitrate.

Scheme 3: Reaction of THP-MMP 18 with decaborane activated complex to form Compound 24

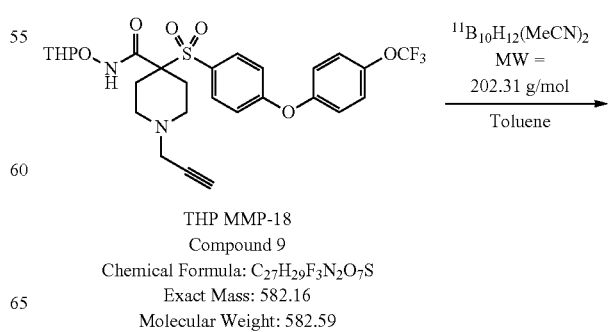

THP MMP-18
Compound 9
Chemical Formula: $C_{27}H_{29}F_3N_2O_7S$
Exact Mass: 582.16
Molecular Weight: 582.59

-continued

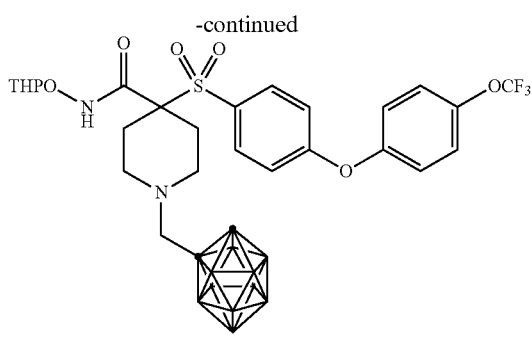

($^{11}$B)-THP MMP-18 closo-carborane
Compound 24
Chemical Formula: $C_{27}H_{39}B_{10}F_3N_2O_7S$
Molecular Weight: 700.78

This reaction tended to yield complex mixtures, which may be due to the hydroxamate moiety undergoing chelation with decaborane or the corresponding decaborane activated complex. Without being bound by any particular theory, a more hindered protecting group than THP for the Hydroxamate can address this issue.

According to Kliegel et al., Eur J Inorg Chem 1983, 116, 2616-2629, reaction of 9-BBN with a THP protected hydroxymate can generate boron chelates, and based on this precedent, this chelation can be a contributing factor to the complex reaction of 9 with decaborane or $B_{10}H_{12}(MeCN)_2$. Kliegel et al. showed that hydroxamic acids chelate 9-BBN, but also demonstrated that O-THP protected hydroxamates can chelate to Lewis acidic boron compounds such as 9-BBN, $BF_3$, and diphenylborinic anhydride. Thus, the hydroxamate can be protected by precomplexation with a borane such as 9-BBN.

An approach (Scheme 6) involved hydroboration of ethyl ester 7 with $B_{10}H_{12}(MeCN)_2$, which generated the ortho-closo-carborane ethyl ester adduct. In addition to the carboranyl ethyl ester 22, another component was formed and identified to be the nido ethyl ester form 23 which is also of interest for BNCT agents in the present disclosure.

Scheme 6: MMP-18 Ethyl Ester Reaction with Decaborane

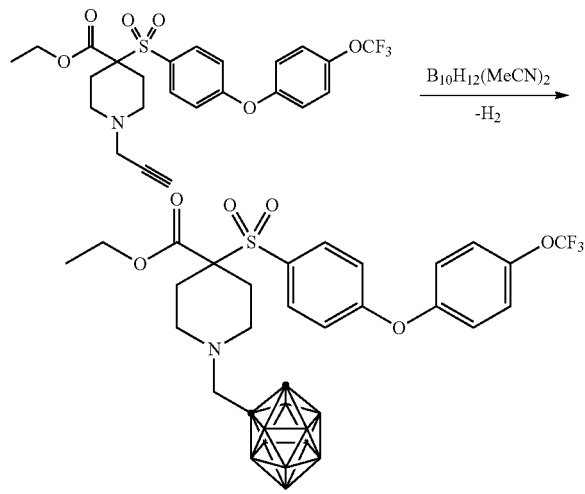

Reaction of ethyl ester 7 with activated after 19 h at 80-85° C. resulted in a 70% conversion to the desired carborane (20) along with 16% of a major impurity which was identified and assigned as the nido ethyl ester species (21) based on HRMS analysis. The desired carboranyl ethyl ester (20) was isolated in 35% yield after flash chromatography. As shown in Scheme 7 below, direct access to carboranyl acid was explored by using a carboxylic acid and activated decaborane, which led to essentially complete consumption of carboxylic acid after 17 h at 80° C. yielding 18% of the desired carboranyl acid.

Scheme 7: Reaction of MMP-Carboxylic Acid with activated decaborane

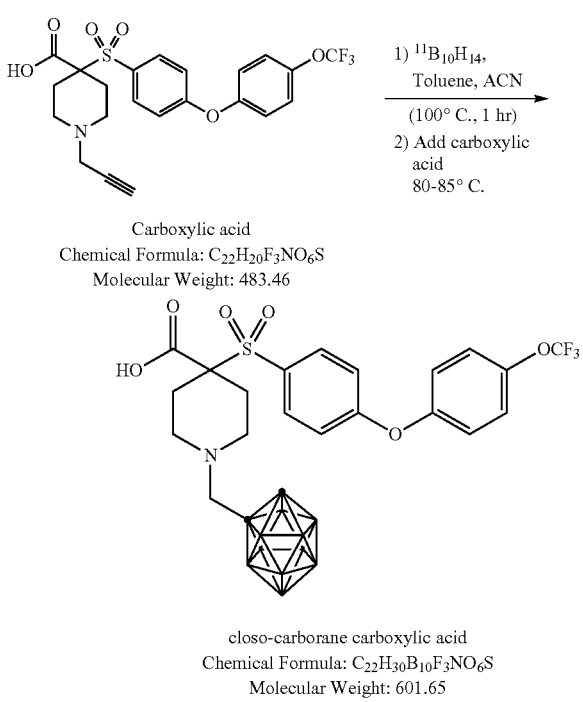

Hydrolysis of carboranyl ester 20 was accomplished in acidic mixtures employing conventional heating of an acid, for example, hydrochloric acid, hydrobromic acid, sulfuric acid, or methanesulfonic acid at 100° C., and also at higher temperatures under microwave irradiation. The addition of acetic acid was beneficial to ensure that the mixtures remained homogeneous. The use of hydrochloric acid generated larger amounts of nido carboxylic acid form, whereas the use of sulfuric acid generated lower levels of nido carboxylic acid, and the use of methanesulfonic acid also generated larger amounts of nido carboxylic acid form compared to sulfuric acid. Performing the hydrolysis for 60 minutes in the microwave using 90% sulfuric acid (125 volumes) and acetic acid (250 volumes) gave the desired carboranyl acid product (~80% conversion), with near consumption of starting material, and <10% of nido impurities. UPLC/MS confirmed the correct molecular ion [M+H]+= 602 m/z for the desired carboranyl acid product. The hydrolysis was also successful under flow conditions at 150° C. for 75 minutes providing the same conversion observed with microwave irradiation. The use of continuous flow generated substantially cleaner product with a residence time of 75 minutes and achieved 78-80% conversion to product with 18-20% unreacted starting materiel ethyl ester which can be easily recovered by normal-phase chromatography and subsequently recycled for continuous flow processing.

After the desired carboranyl acid 22 was produced, the rest of the synthesis focused on preparation of the acid chloride, subsequently forming the protected hydroxamate using THPONH$_2$ and lastly cleaving the THP group with acidic reagent to isolate the carboranyl salt as illustrated in Scheme 8.

Scheme 8: Synthetic Pathway to access Carbonyl final product

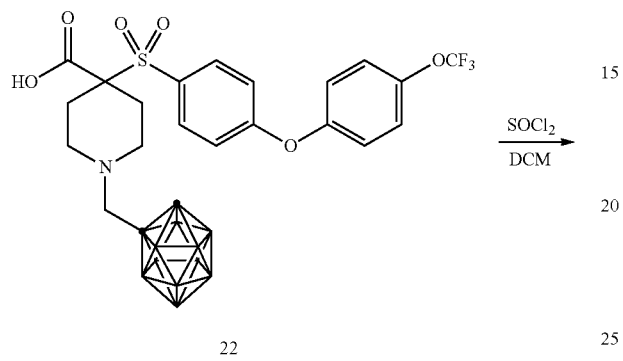

22
closo-carborane carboxylic acid
C$_{22}$H$_{30}$B$_{10}$F$_3$NO$_6$S
Molecular Weight: 601.65

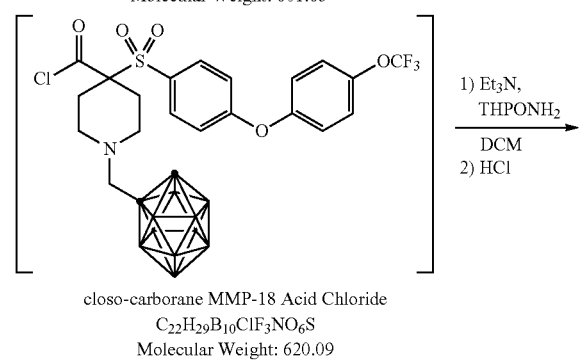

closo-carborane MMP-18 Acid Chloride
C$_{22}$H$_{29}$B$_{10}$ClF$_3$NO$_6$S
Molecular Weight: 620.09

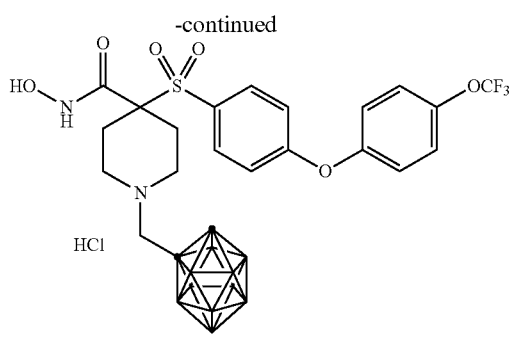

closo-carborane MMP-18 HCl salt
C$_{22}$H$_{32}$B$_{10}$ClF$_3$N$_2$O$_6$S
Molecular Weight: 653.12

Click Chemistry to Attach Boron Cluster to Alkyne 9

The scope of the next phase of this project revolved around the use of Click chemistry to attach boron clusters to the alkyne moiety of 9. There are a number of methods of employing Click chemistry coupling azides to alkynes either thermally or via copper or ruthenium catalysis (CuAAC or RuAAC, respectively). However, since matrix metalloproteinases (MMPs) are being targeted, the use of copper may cause downstream issues since MMPs have an affinity for divalent metals. The thermal Click reaction without metal catalysis was first used to prepare both the 1,4-disubstituted and 1,5-disubstituted Click products.

The overall synthetic scheme to prepare both the 1,4-disubstituted and 1,5-disubstituted Click products was accomplished by preparation of protected carboranyl propyl azide and subsequent Click reaction with 9 in toluene at elevated temperatures (120-140° C.). The synthetic scheme for preparation of carboranyl propyl azide is shown below in Scheme 9:

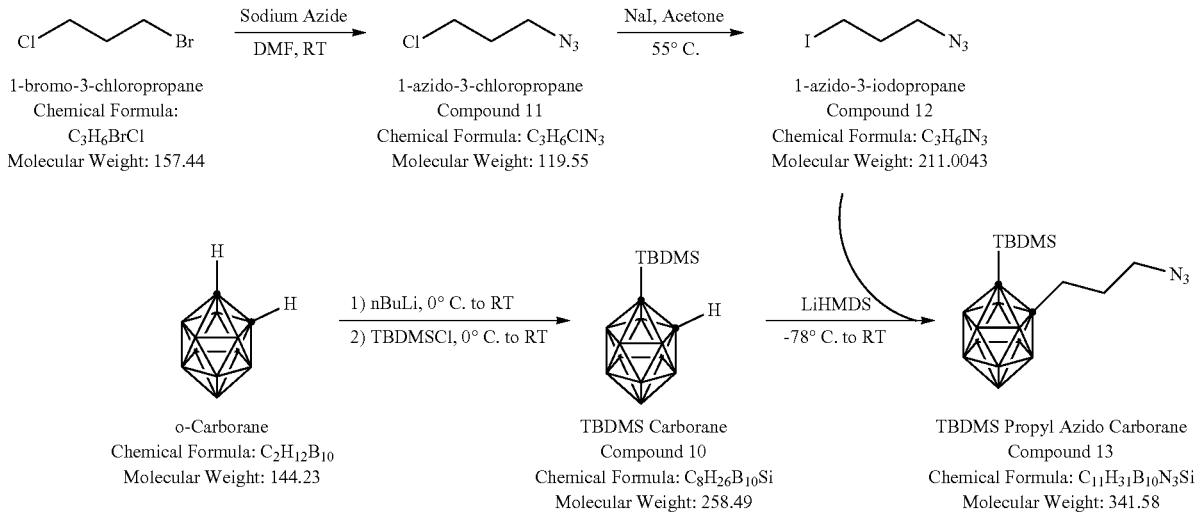

Formation of 1-azido-iodopropane was accomplished based on literature precedent, which entailed an $S_N2$ reaction of sodium azide and 1-bromo-3-chloropropane in DMF, providing a 95% yield of 1-azido-3-chloropropane as the major product along with ~15% of 1-azido-3-bromopropane, which was taken forward without further purification. See Choi, Shirley et al. Angew Chem Int Ed Engl, 2017 7420-7424. The crude 1-azido-3-halopropane was subjected to Finkelstein conditions using sodium iodide in warm acetone that generated pure 1-azido-3-iodopropane in 81% isolated yield after silica plug purification. The next reaction involved preparation of the TBDMS-protected carborane derivative (13), which entailed deprotonation of the o-carborane with n-butyllithium (n-BuLi), generating the carborane anion that subsequently attacks TBDMSCI affording highly pure TBDMS carborane (10) in 94% isolated yield post silica plug purification. The last step to prepare the TBDMS propyl azido carborane (13) uses novel anion generating conditions. The deprotonation was accomplished using lithium hexamethyldisilazide (LiHMDS) to generate the carboranyl anion that sequentially attacks 1-azido-3-iodo-propane to furnish pure TBDMS propyl azido carborane in 98% isolated yield post silica plug purification. Thus, also provided herein is a tert-butyldimethylsilyl ether propyl azido carborane compound having a structure:

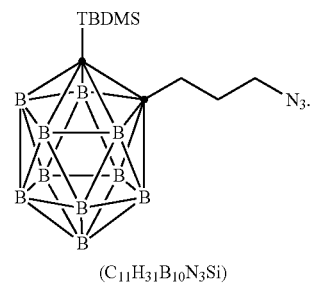

$(C_{11}H_{31}B_{10}N_3Si)$

The thermal heating of an azide and an alkyne without copper and ruthenium agents generates a mixture of 1,4-disubstituted and 1,5-disubstituted triazole products. Executing the Click chemistry on TBDMS propyl azido carborane (13) and 9 confirmed formation of 1,4-disubstituted triazole and 1,5-disubstituted triazole products. Two separate reactions were carried out using copper to facilitate the selective formation of the 1,4-disubstituted Click product and ruthenium catalysis to promote selective formation of the 1,5-disubstituted Click product. Scheme 10 depicts the thermal click reaction.

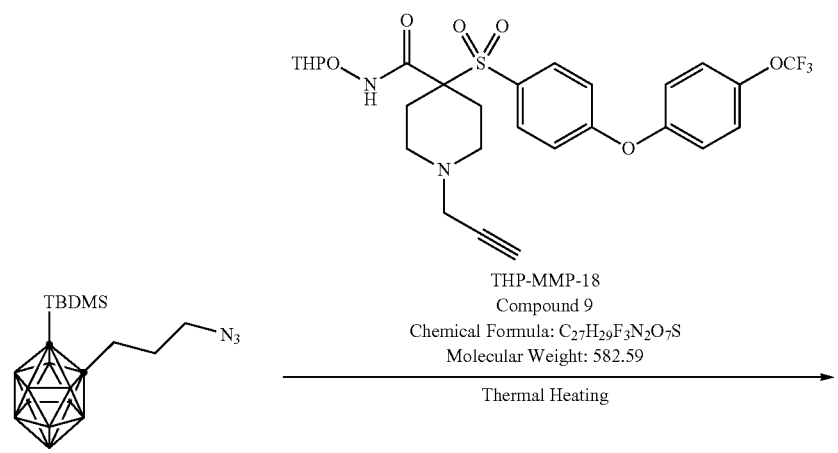

Scheme 10: Thermal click reaction between alkyne (9) and azide (13)

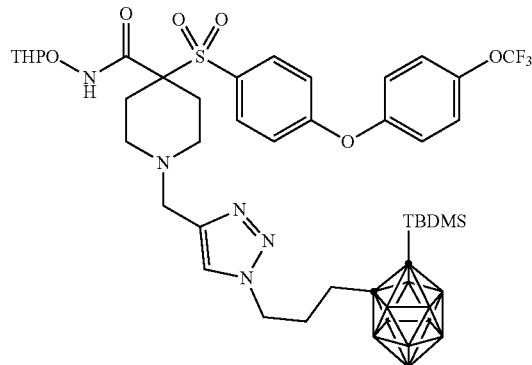

THP MMP-18 1,4-Click TBDMS Product
Chemical Formula: $C_{38}H_{60}B_{10}F_3N_5O_7SSi$
Molecular Weight: 924.17

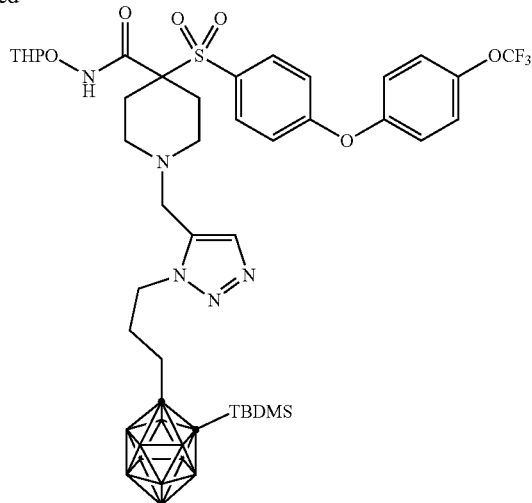

THP MMP-18 1,5-Click TBDMS Product
Chemical Formula: $C_{38}H_{60}B_{10}F_3N_5O_7SSi$
Molecular Weight: 924.17

Carrying out the CuAAC reaction (Scheme 11) using stoichiometric copper sulfate and excess sodium ascorbate in aqueous THF at room temperature produced solely the 1,4-disubstituted triazole.

Scheme 11: CuAAC Reaction of Alkyne 9 and Carboranyl Azide

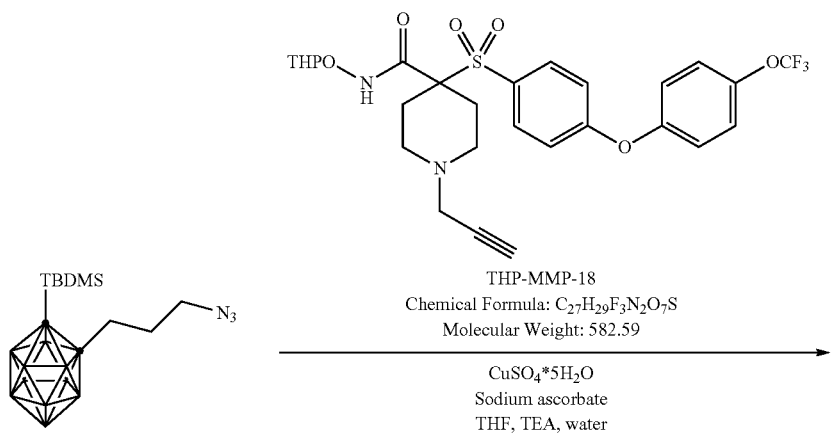

TBDMS Propyl Azido Carborane
Chemical Formula: $C_{11}H_{31}B_{10}N_3Si$
Molecular Weight: 341.58

THP-MMP-18
Chemical Formula: $C_{27}H_{29}F_3N_2O_7S$
Molecular Weight: 582.59

$CuSO_4*5H_2O$
Sodium ascorbate
THF, TEA, water
Room Temp

-continued

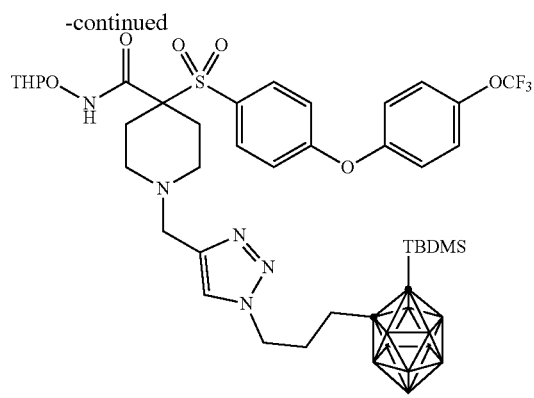

THP MMP-18 Click TBDMS Product
Chemical Formula: $C_{38}H_{60}B_{10}F_3N_5O_7SSi$
Molecular Weight: 924.17

Performing the RuAAC reaction (illustrated in Scheme 12) generated the 1,5-disubstituted triazole with only trace amounts (<2% AUC) of the 1,4-click product when performing the reaction at ambient temperature.

Scheme 12: RuAAC Reaction of Alkyne 9 and Carboranyl Azide

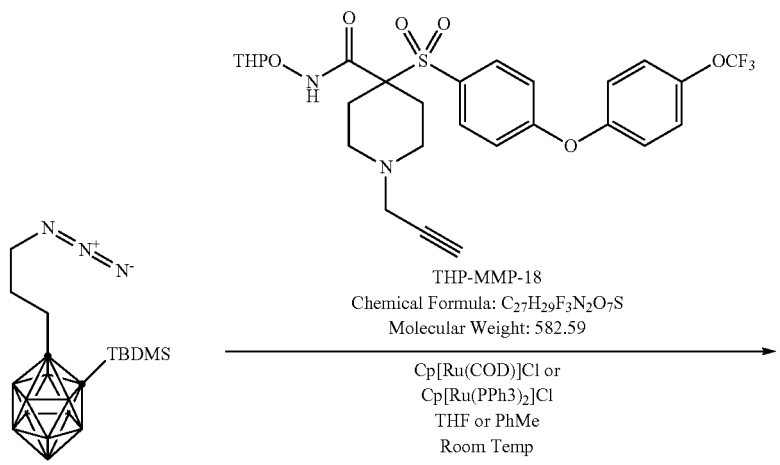

TBDMS Propyl Azido Carborane
Chemical Formula: $C_{11}H_{31}B_{10}N_3Si$
Molecular Weight: 341.58

THP-MMP-18
Chemical Formula: $C_{27}H_{29}F_3N_2O_7S$
Molecular Weight: 582.59

Cp[Ru(COD)]Cl or
Cp[Ru(PPh3)$_2$]Cl
THF or PhMe
Room Temp

-continued

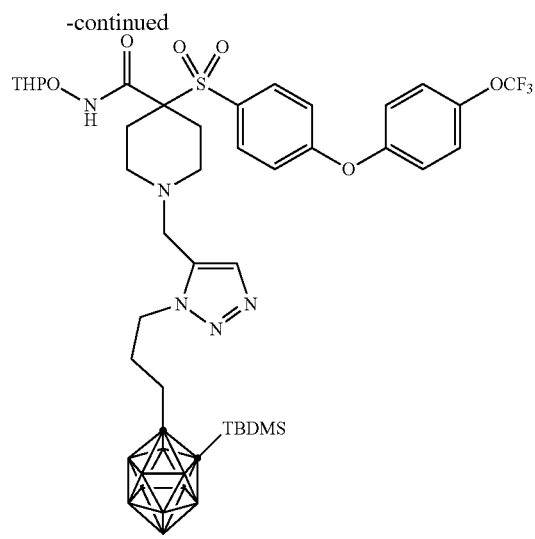

1,5-Disubstituted Click TBDMS Product
Chemical Formula: $C_{38}H_{60}B_{10}F_3N_5O_7SSi$
Molecular Weight: 924.17

RuAAC Reaction of Alkyne 9 and Carboranyl Azide

During the evaluation of the RuAAC chemistry, a series of two common ruthenium catalysts were screened in either toluene or tetrahydrofuran to determine which catalyst/solvent system was most effective in generating the 1,5-disubstituted triazole. The chloro(pentamethylcyclopentadienyl)(cyclooctadiene)ruthenium(II) (Cp*Ru(COD)Cl) catalyst was found to be superior to the pentamethylcyclopentadienylbis-(triphenylphosphine)ruthenium(II) chloride (Cp*Ru(PPh$_3$)$_2$Cl) catalyst. Further, performing the reaction in a polar solvent (THF) generated higher conversion to the 1,5-click product compared to running the reaction in nonpolar solvent such as toluene.

Given the work to identify which component was either 1,4-Click or 1,5-Click product, the next phase was to optimize the thermal click reaction in toluene as the solvent medium. The temperatures screened for the thermal click reaction were 100° C., 120° C., and 140° C. The click reaction at 100° C. is significantly slower compared to the reactions at 120° C. and 140° C. The reaction at 120° C. was capable of progressing to 62% conversion (sum of both Click regioisomers) after 42 hours, but the reaction at 140° C. for 19 hours performed slightly better with a total conversion of 69% (sum of both Click regioisomers) and contained less starting material alkyne (22%). The formation of nido was lower at 120° C. even after 42 hours and slightly elevated at 140° C. after 19 hours. However, heating the mixture for longer periods of time at 140° C. does consume more starting material alkyne, but at the expense of forming significantly higher amount of nido-like by-products.

Batch preparation of the Click regioisomers was executed on a gram scale using batch-type pressure vessels at 120° C. for 58 hours. HPLC analysis of the reaction after 58 hours showed ~65% conversion (sum of Click regioisomers) with ~20% unreacted alkyne. HPLC analysis confirmed that the thermal Huisgen 1,3-dipolar cycloaddition reaction gives 1,4-Click and 1,5-Click products with a ratio of 1.6 to 1, respectively, which agrees with a study reported in Sharpless et al., Angewandte Chemie 2002, 114, 2708-2711 regarding the component ratio of the Click regioisomers. Cleavage of the TBDMS group was executed using 1M tetrabutylammonium fluoride (TBAF) in THF, which is shown in Scheme 13 for the 1,4-Click regioisomer and in Scheme 14 for the 1,5-Click regioisomer.

Scheme 13-Cleaving the TBDMS group of the 1,4-Click regioisomer

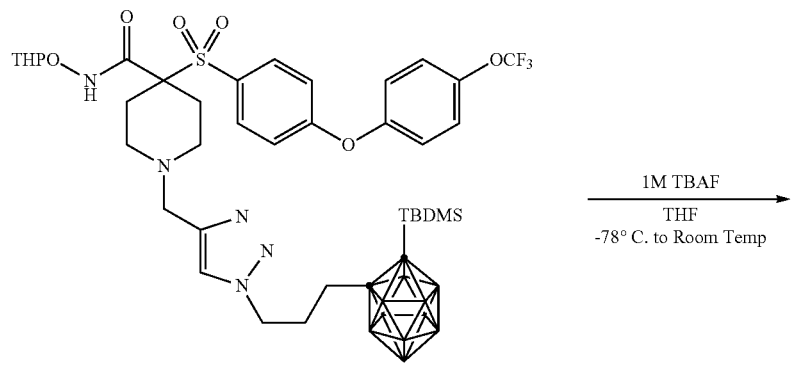

1,4-Click Product
THP MMP-18 1,4-Click TBDMS Product
Chemical Formula: $C_{38}H_{60}B_{10}F_3N_5O_2SSi$
Molecular Weight: 924.17

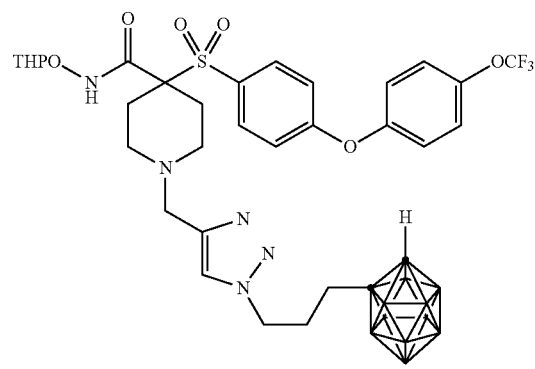

1,4-Click Product
THP MMP-18 1,4-Click TBDMS Product
Chemical Formula: $C_{32}H_{40}B_{10}F_3N_5O_2S$
Molecular Weight: 609.91

Scheme 14 - Cleaving the TBDMS group of the 1,5-Click regioisomer

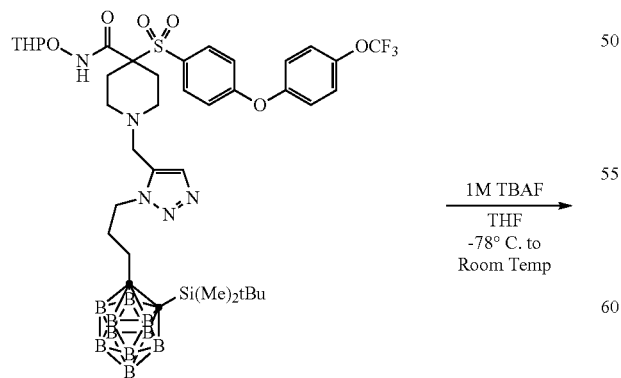

THP MMP-18 1,5-Disubstituted Click
TBDMS Product
Chemical Formula: $C_{38}H_{60}B_{10}F_3N_5O_7SSi$
Molecular Weight: 924.17

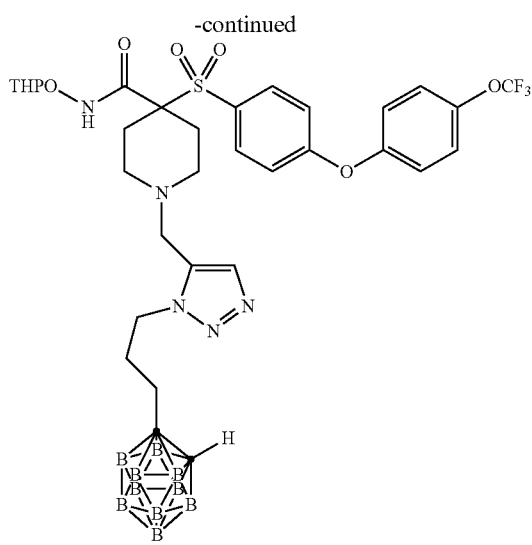

1,5-Click Product
THP MMP-18 1,5-Click Product
Chemical Formula: C₃₂H₄₆B₁₀F₃N₅O₇S
Molecular Weight: 809.91

Deprotection of the THP protecting group was executed using 4N HCl in 1,4-dioxane at room temperature as depicted in Scheme 15 and Scheme 16 below. Once the reaction was complete, the reaction mixture was concentrated, redissolved in dichloromethane, and subsequently precipitated using diethyl ether.

Scheme 15: Cleaving the THP group of the 1,4-Click regioisomer

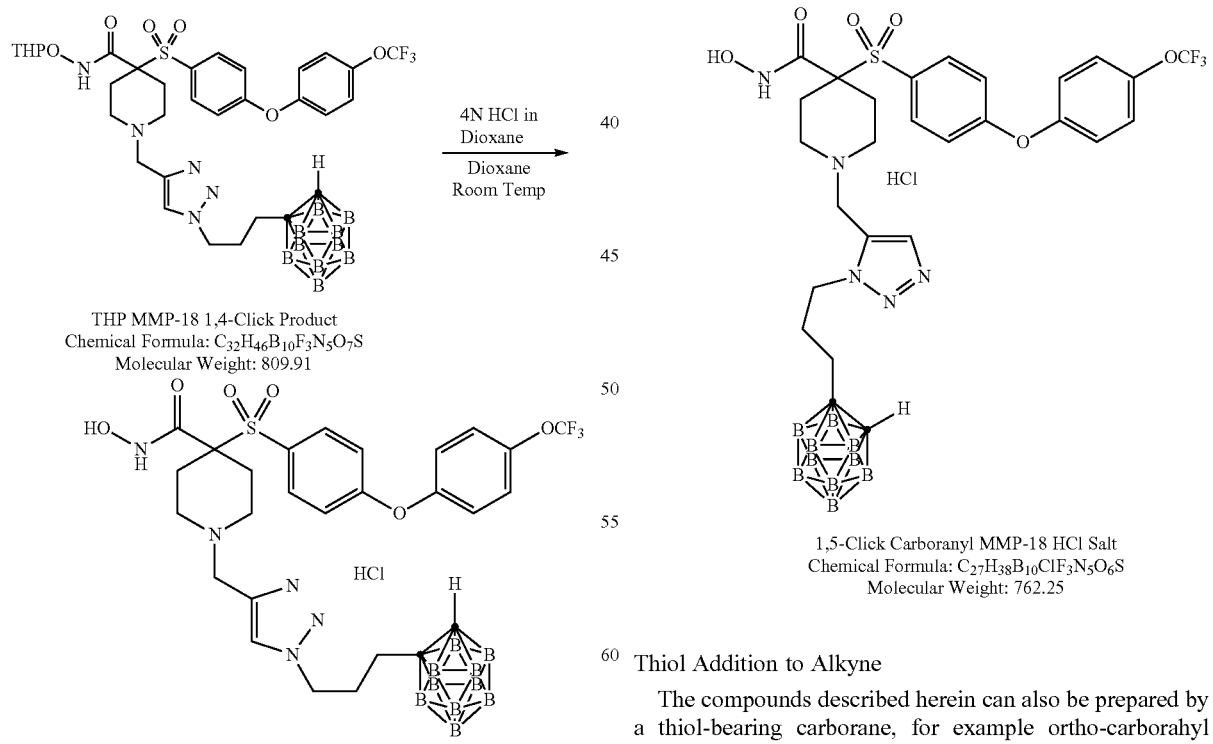

THP MMP-18 1,4-Click Product
Chemical Formula: C₃₂H₄₆B₁₀F₃N₅O₇S
Molecular Weight: 809.91

1,4-Click Carboranyl MMP-18 HCl Salt
Chemical Formula: C₂₇H₃₉B₁₀ClF₃N₅O₆S
Molecular Weight: 762.25

Scheme 16: Cleaving the THP group of the 1,5-Click regioisomer

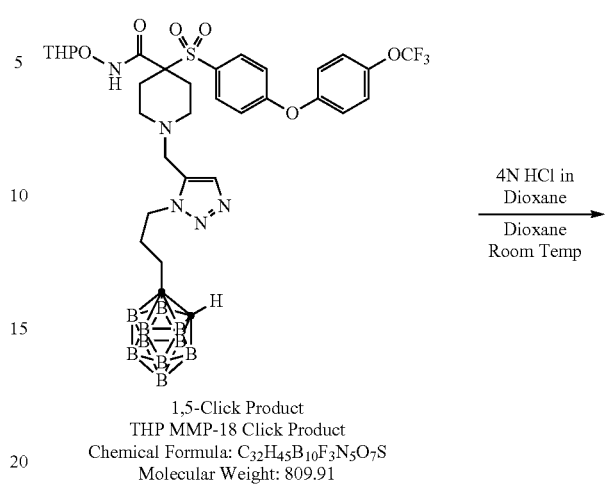

1,5-Click Product
THP MMP-18 Click Product
Chemical Formula: C₃₂H₄₅B₁₀F₃N₅O₇S
Molecular Weight: 809.91

1,5-Click Carboranyl MMP-18 HCl Salt
Chemical Formula: C₂₇H₃₈B₁₀ClF₃N₅O₆S
Molecular Weight: 762.25

Thiol Addition to Alkyne

The compounds described herein can also be prepared by a thiol-bearing carborane, for example ortho-carborahyl thiol (Scheme 17), or a different isomer such as meta-carboranyl thiol, or for example using a carboranyl alkylene thiol. The radical addition may be accomplished for example in toluene or in 1,4-dioxane.

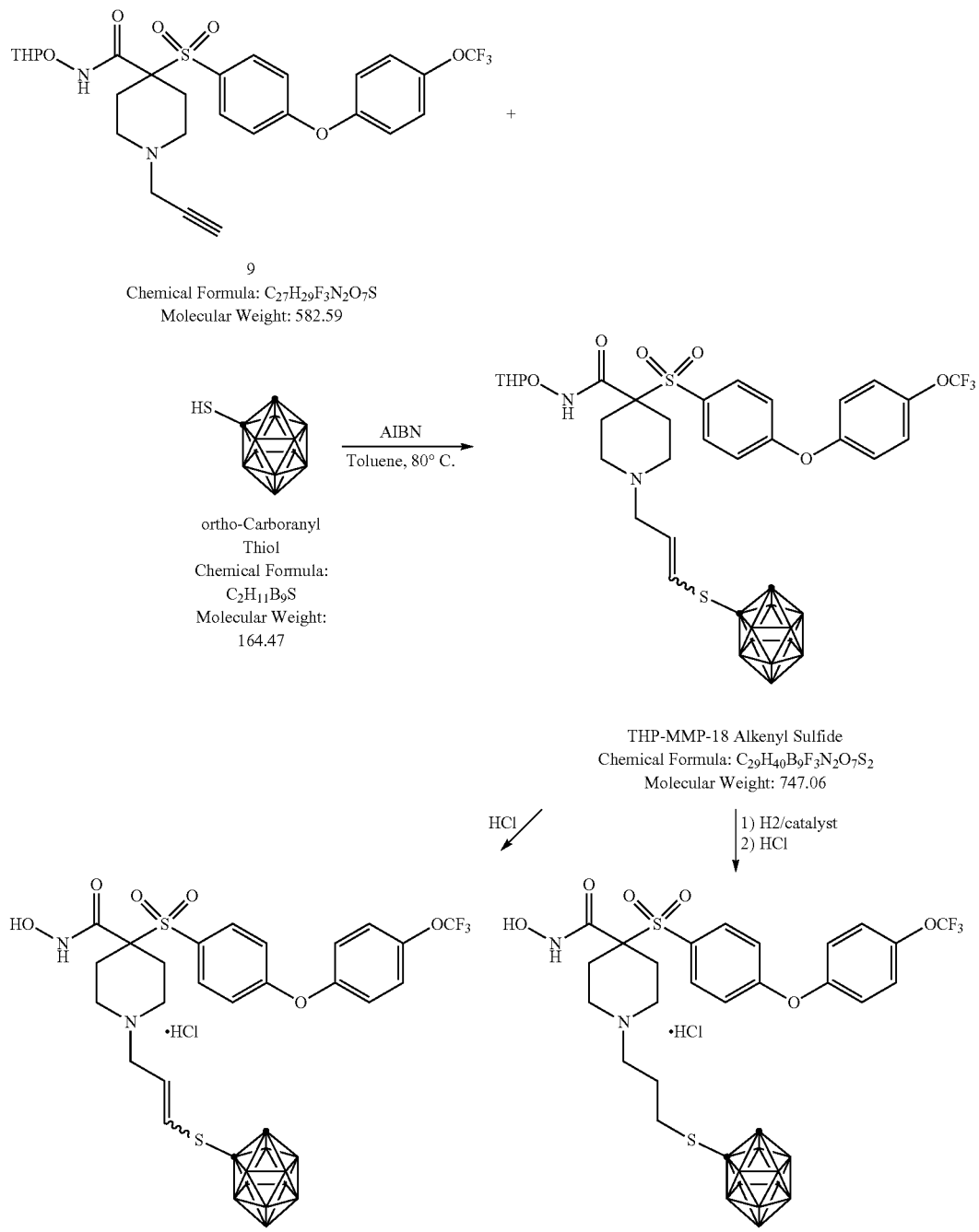

Scheme 17.

MMP-2 and MMP-9 Inhibitory Potency

The MMP inhibitory potency of the Click isomers was tested, and demonstrate that the compounds are potent binders to MMP receptors that are upregulated in tumor cells. See Example 26 for further guidance/discussion.

Boron Neutron Capture Therapy Using [10]B Enriched Compounds

Any of the compounds described herein may be prepared with [10]B-enriched boron to further enhance the efficiency and efficacy of BNCT.

Additional guidance for preparing the compounds described herein can be found in the Examples section.

Methods of Use

The compounds described herein (e.g., the compounds of Formula I, Ia', Ia", Ib, II, IIa', IIa", IIb, III, IIIa', IIIa", IIIb, IV, IVa', Va", or IVb or pharmaceutically acceptable salts thereof) can bind to and/or inhibit MMP, such as MMP-13, MMP-2, MMP-9, or combinations thereof. Overexpression of MMP has been implicated in a variety of conditions, including tumor growth and metastasis, and in the degradation of articular cartilage in arthritis. Martel-Pelletier et. al *Best Practice & Research Clinical Rheumatology* 15(5): 805-829 (2001). Thus, the compounds described herein are capable of selectively transporting a high concentration of $^{10}$B atoms in the boron-dense carborane to MMPs. Without intending to be bound by any particular theory, when these cells are exposed to an epithermal neutron beam, the $^{10}$B nuclei adsorbs a neutron to form an excited $^{11}$B nucleus, which undergoes decay via fission to emit an α-particle ($^{4}$He$^{2+}$) as well as a $^{7}$Li$^{3+}$ ion, both with high kinetic energy. These highly charged particles can damage the surrounding tissue. Thus, provided herein is a method of delivering $^{10}$B atoms to matrix metalloproteinase ("MMP") in a cell, comprising contacting the cell with the compound described herein (e.g., the compounds of Formula I, Ia', Ia", Ib, II, IIa', IIa", IIb, III, IIIa', IIIa", IIIb, IV, IVa', IVa", or IVb or pharmaceutically acceptable salts thereof), wherein the compound binds to MMP with an IC$_{50}$ of 1 μM or less.

Also provided herein is a method of inhibiting MMP in a cell comprising contacting the cell with a compound described herein in an amount effective to inhibit the MMP. In some embodiments, the MMP is MMP-13, MMP-2, MMP-9, or a combination thereof. The contacting of the cell can occur in vitro or in vivo. In some cases, contacting of the cell occurs in vitro. In other cases, contacting of the cell occurs in vivo. The compounds described herein can contact a cell in vivo by administering a compound described herein to a subject in need of MMP inhibition, such as MMP-13, MMP-2, and/or MMP-9 inhibition. Therefore, the disclosure includes administering one or more of a compound described herein to a subject, such as a human, in need thereof. In some embodiments, the subject suffers from cancer, rheumatoid arthritis, or both.

In view of the above, in various aspects, the disclosure includes a method of treating a disease in a subject. In some embodiments, the method comprises administering a therapeutically effective amount of a compound described herein to a subject in need of MMP inhibition, such that MMP is inhibited. In various embodiments, the method comprises administering a therapeutically effective amount of a compound described herein to a subject to treat a disease or disorder resulting from overexpression of MMP in a subject (e.g., tumor growth, metastasis, degradation of articular cartilage in arthritis). Conditions resulting from overexpression of MMP can include those related to, for example, cancer and rheumatoid arthritis.

Use of a compound described herein to treat a condition resulting from overexpression of MMP in a subject, as well as use of a compound described herein in the preparation of a medicament for treating the condition, also are contemplated.

Pharmaceutical Formulations

Also provided herein are pharmaceutical formulations that include a compound described herein (e.g., a compound of Formula I, Ia', Ia", Ib, II, IIa', IIa", IIb, III, IIIa', IIIa", IIIb, IV, IVa', IVa", or IVb or a pharmaceutically acceptable salt thereof), as previously described herein, and one or more pharmaceutically acceptable excipients.

The compounds described herein can be administered to a subject in a therapeutically effective amount. The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

The compounds disclosed herein can be administered in combination with one or more additional pharmaceutically active compounds/agents. The additional pharmaceutically active compounds/agents may be small molecules or can be macromolecules such as proteins, antibodies, peptibodies, DNA, RNA or fragments of such macromolecules.

The compounds disclosed herein and other pharmaceutically active compounds, if desired, can be administered to a patient or subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. enteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds described herein can be administered to a patient or subject at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the patient or subject, the severity of the condition or disease being treated, and the pharmacological activity of the compound being administered. The determination of dosage ranges and optimal dosages for a particular patient or subject is within the ordinary skill in the art.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions might be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention.

Example 1: Preparation of Carborane Substituted SC-276 Using Nucleophilic Substitution

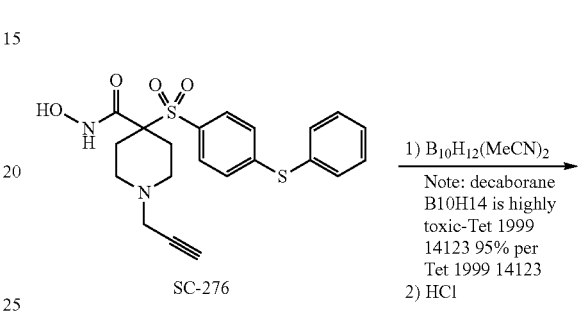

Carborane-substituted SC-276 can be prepared by reacting the alkyne of SC-276 with a cyano-substituted carborane, such as $B_{10}H_{12}(CH_3CN)_2$, according to the methods described by Giovenzana et al., *Tetrahedron* 55(49):14123 (1999).

Example 2: Preparation of Carborane Substituted-SC-276 Using Click Chemistry

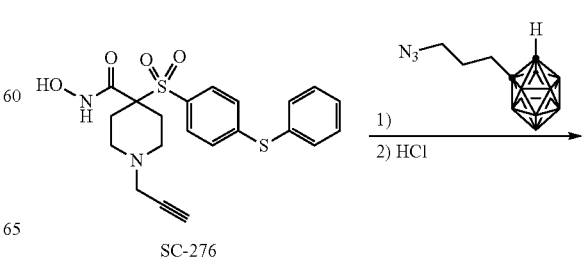

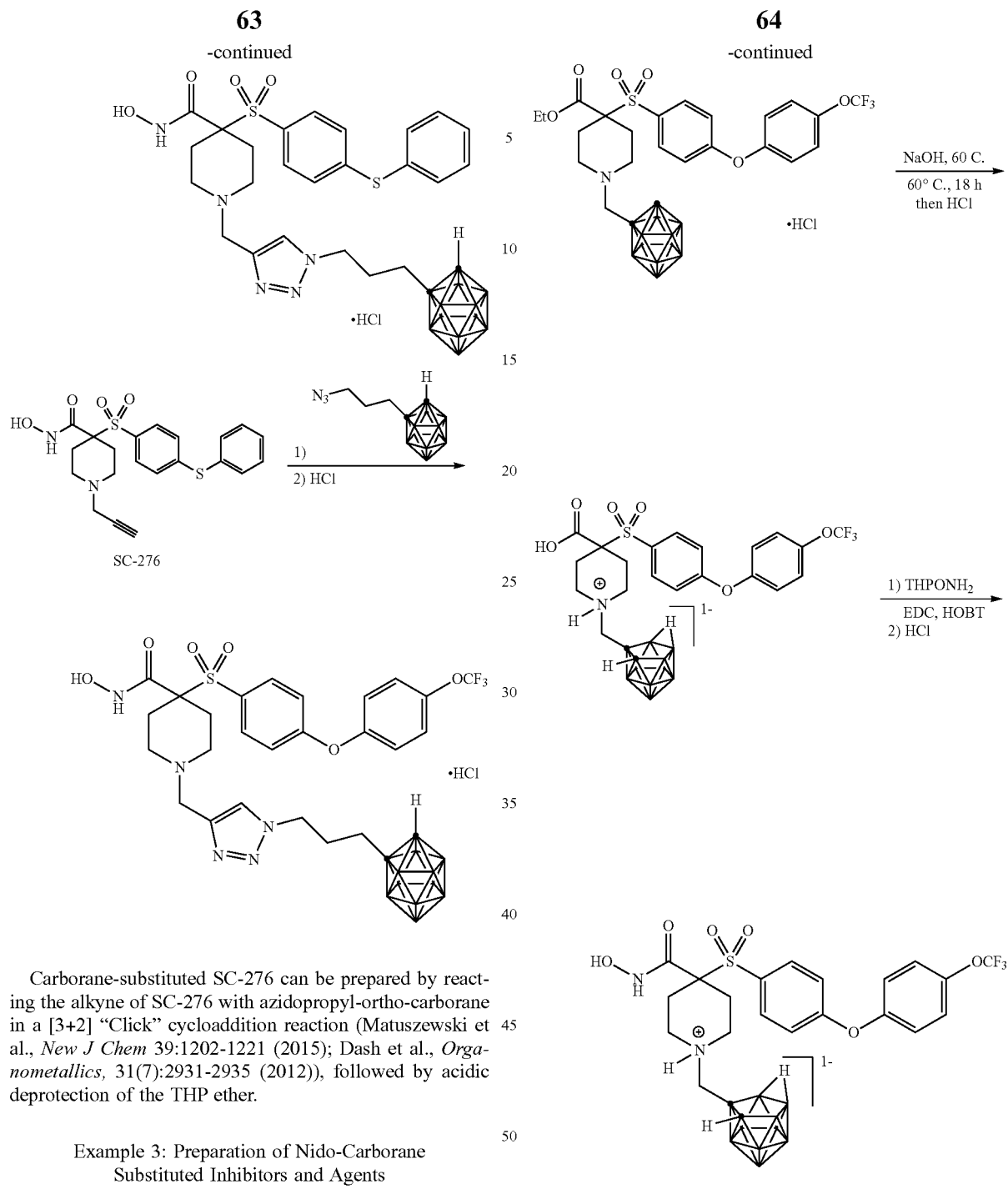

Carborane-substituted SC-276 can be prepared by reacting the alkyne of SC-276 with azidopropyl-ortho-carborane in a [3+2] "Click" cycloaddition reaction (Matuszewski et al., *New J Chem* 39:1202-1221 (2015); Dash et al., *Organometallics*, 31(7):2931-2935 (2012)), followed by acidic deprotection of the THP ether.

Example 3: Preparation of Nido-Carborane Substituted Inhibitors and Agents

Nuceophilic Substitution

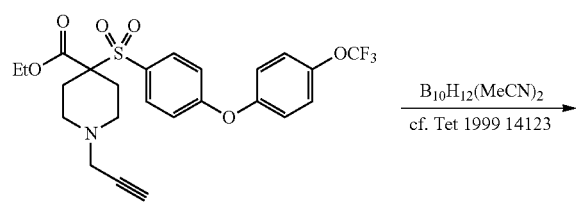

20 JMC 2010 characterization of this intermediate was not reported

Cage-opened anionic nido-carborane complexes can be prepared through treatment of the closo-carborane with nucleophiles, such as hydroxide in alcohol. Thus, the ethyl ester propargyl piperidine (see e.g., Becker et al., Med Chem 53:6653-6680 (2010)) is reacted with $B_{10}H_{12}(MeCN)_2$, followed by concurrent saponification of the ethyl ester moiety and conversion of the closo-carborane to the anionic nido-carborane to yield a zwitterionic carboxylic acid derivative, which is coupled with $THPONH_2$, and then deprotected to yield the hydroxamate target.

Click Chemistry

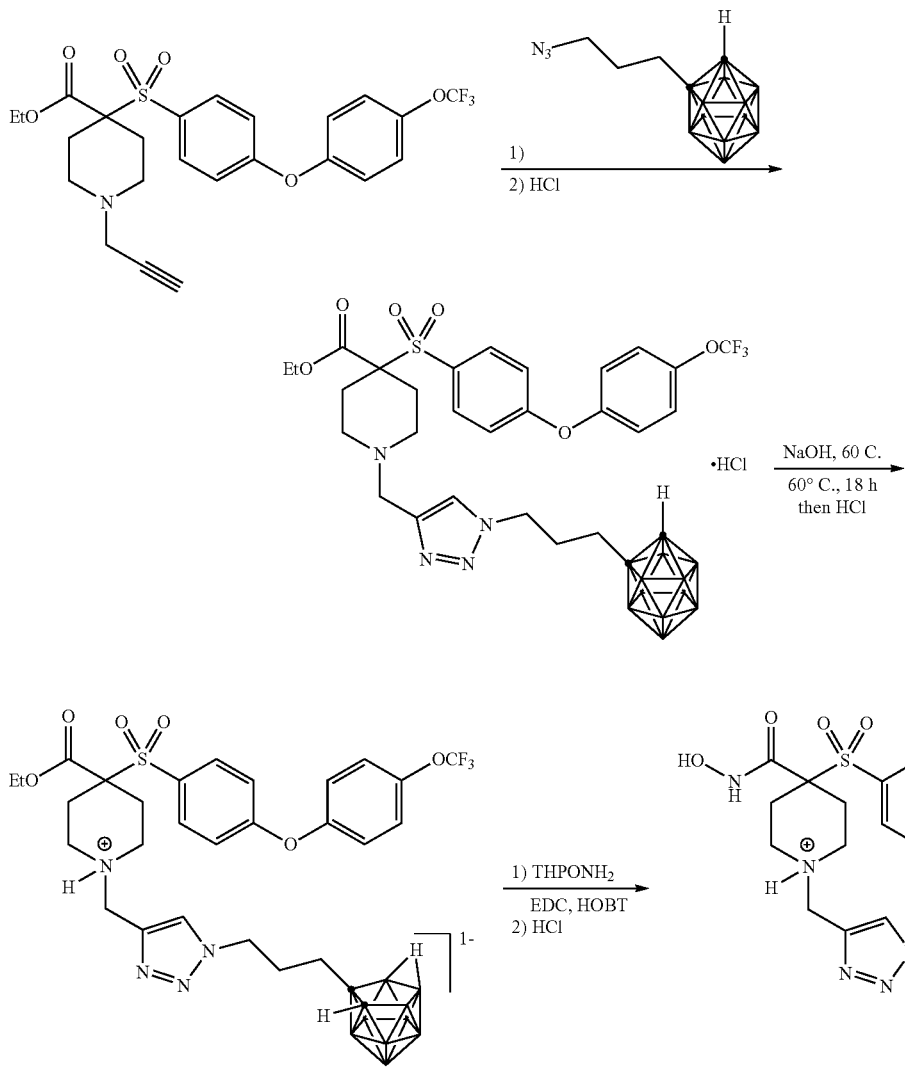

Similarly, Click chemistry on the alkyne forms the triazole linker with the carborane, which undergoes saponification and cage opening with hydroxide, followed by coupling and deprotection to yield the anionic nido-carborane hydroxamates with the protonated piperidine moiety.

Example 4: Preparation of Inhibitors and Agents from Novel Intermediates

-continued

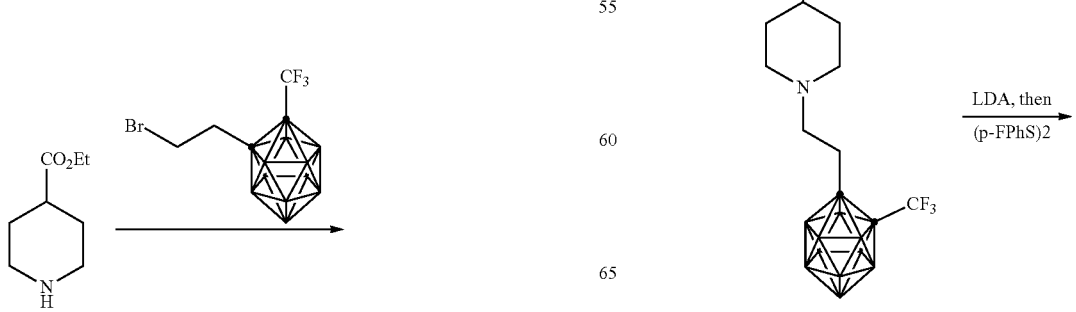

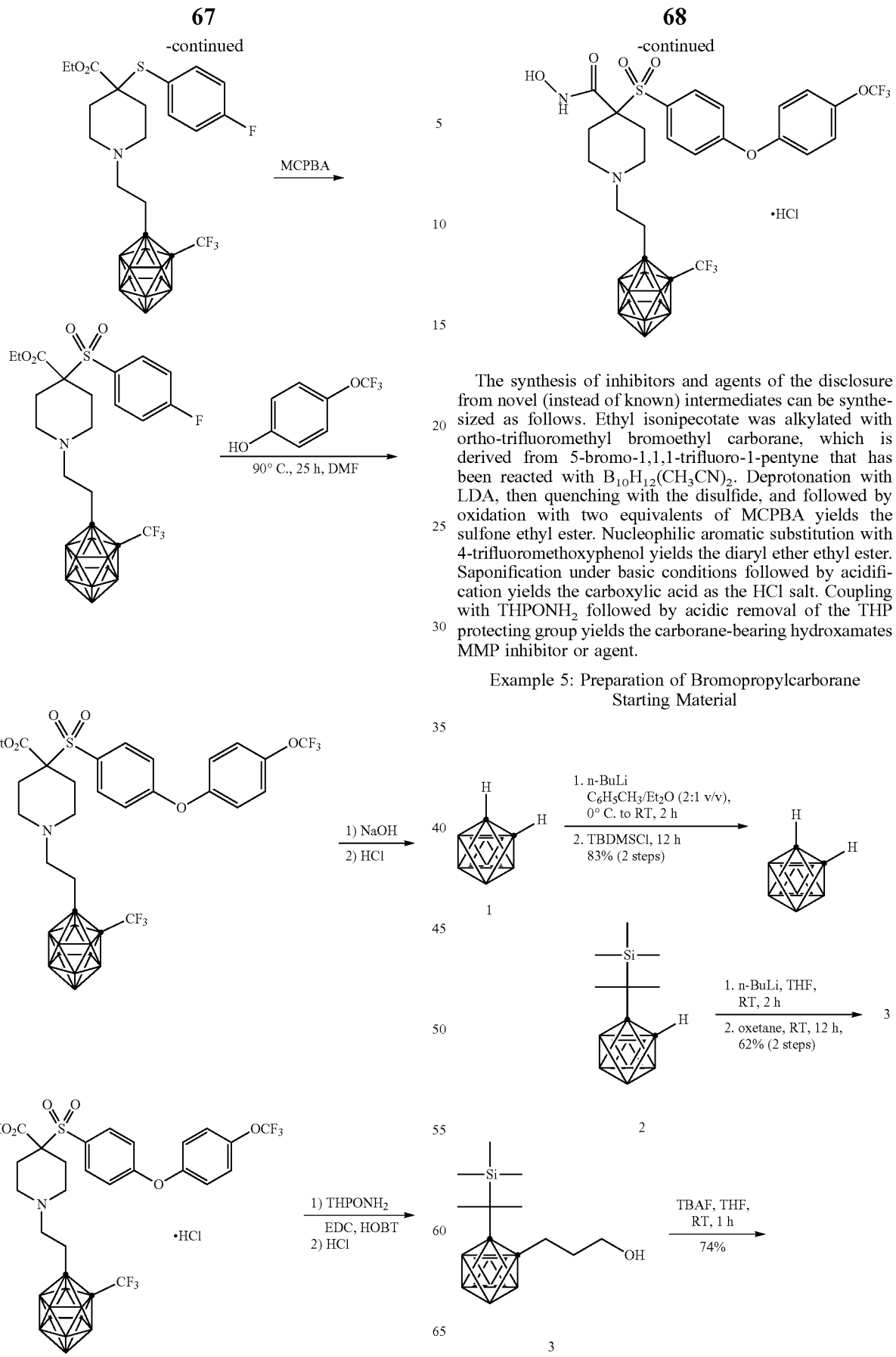

The synthesis of inhibitors and agents of the disclosure from novel (instead of known) intermediates can be synthesized as follows. Ethyl isonipecotate was alkylated with ortho-trifluoromethyl bromoethyl carborane, which is derived from 5-bromo-1,1,1-trifluoro-1-pentyne that has been reacted with $B_{10}H_{12}(CH_3CN)_2$. Deprotonation with LDA, then quenching with the disulfide, and followed by oxidation with two equivalents of MCPBA yields the sulfone ethyl ester. Nucleophilic aromatic substitution with 4-trifluoromethoxyphenol yields the diaryl ether ethyl ester. Saponification under basic conditions followed by acidification yields the carboxylic acid as the HCl salt. Coupling with $THPONH_2$ followed by acidic removal of the THP protecting group yields the carborane-bearing hydroxamates MMP inhibitor or agent.

Example 5: Preparation of Bromopropylcarborane Starting Material

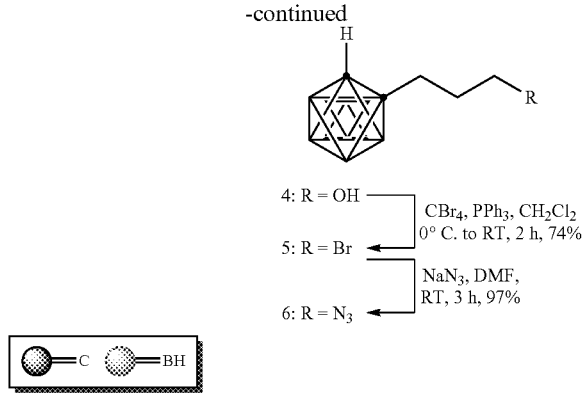

The intermediate, 1-(3-bromopropyl)-1,2-dicarbacloso-dodecaborane (5), is prepared according to the method by Ahrens et al. *J. Med. Chem.* 54:2368 (2011).

Example 6: Preparation of Bis(4-Fluorophenyl) disulfide (Compound 1)

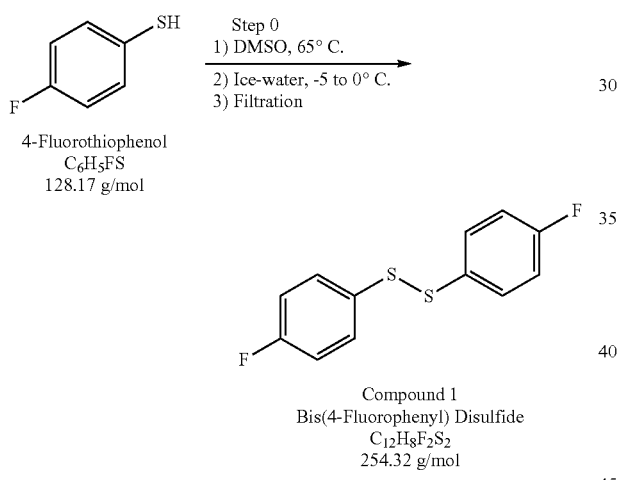

A mixture of 4-fluorothiophenol (215.25 g, 1.68 moles) was heated with DMSO (1.4 liters) at 65° C. for 8 hours. The mixture was cooled to 15° C. and added (via vacuum transfer using a PTFE transfer line) to a separate reactor equipped with an overhead mechanical stirrer that contained a 5 kg mixture of ice/USP purified water to afford a white slurry. The slurry was allowed to stir overnight at 0-5° C. The following day, the slurry was filtered, wetcake solids were washed with cold USP water (1.5 liters), and pulled dry overnight under a stream of nitrogen to provide Compound 1 (white crystalline solids, 207.4 g, low melting solid, 97.1% yield, HPLC purity: 100% AUC, $^1$H NMR and $^{13}$C NMR analysis: conforms to structure). Stored in the fridge under nitrogen. $^1$H NMR (CDCl$_3$, 400 MHz): δ 7.44 (m, 4H), 7.00 (m, 4H). $^{13}$C NMR (CDCl$_3$, 100 MHz): δ 163.96, 161.49, 132.32, 132.29, 131.43, 131.34, 116.51, 116.29, 77.47, 77.16, 76.84

Example 7: Preparation of 1-tert-butyl 4-ethyl 4-(4-fluorophenylthio)piperidine-1,4-dicarboxylate (Compound 3)

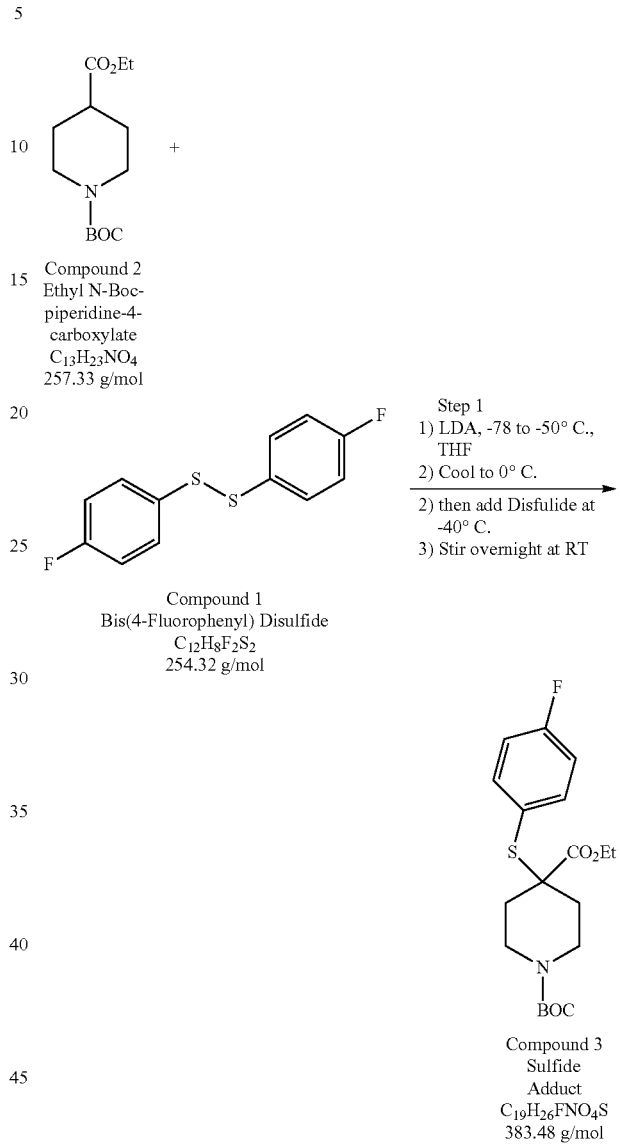

Compound 2 (150.00 g, 0.583 moles) was cooled in anhydrous THF (1.8 liters) to −78° C. To this mixture was slowly added a solution of LDA (2.0 M in THF/Ethylbenzene, 350 mL, 0.700 moles) over 22 minutes such that the temperature did not exceed −70° C. The resulting mixture was allowed to warm to 0° C., then cooled to −40° C., and subsequently a solution of Compound 1 (148.75 g, 0.583 mole) in anhydrous THF (600 mL) was added dropwise over 30 minutes. The mixture was allowed to warm to ambient temperature overnight. The following day, the reaction was deemed complete by HPLC analysis. The reaction mixture was quenched with a solution of acetic acid (7.7 g) in USP water (200 mL), concentrated under reduced pressure at 35-40° C., and the aqueous residue was extracted with ethyl acetate (3×450 mL). The combined organic layers were successively washed with USP water (300 mL), brine (500 mL), dried with sodium sulfate, and concentrated under reduced pressure to provide crude sulfide adduct (232.4 g).

Silica plug (1.2 Kg, 60-200 micron, 5:1 ratio) purification of the crude sulfide using ethyl acetate/heptane provided Compound 3 (light yellow oil, 192.26 g, 86.0% yield, HPLC purity: 99% AUC, $^1$H NMR and $^{13}$C NMR analysis: conforms to structure). $^1$H NMR (CDCl$_3$, 400 MHz): δ 7.41 (m, 2H), 7.02 (m, 2H), 4.13 (q, 2H, J=14.4 Hz), 3.80 (bd, 2H), 3.09 (m, 2H), 2.09 (m, 2H), 1.76 (m, 2H), 2.12-2.06 (m, 2H), 1.75 (m, 2H), 1.45 (s, 9H), 1.22 (t, 3H, J=7.2 Hz). $^{13}$C NMR (CDCl$_3$, 100 MHz): δ 171.72, 165.16, 162.67, 154.71, 139.17, 139.08, 125.16, 125.13, 116.12, 115.90, 79.81, 77.48, 77.16, 76.84, 61.33, 53.79, 33.17, 28.48, 14.16.

Example 8: Preparation of 1-Tert-Butyl 4-Ethyl 4-(4-Fluorophenylsulfonyl)Piperidine-1,4-dicarboxylate (Compound 4)—Alternative Route

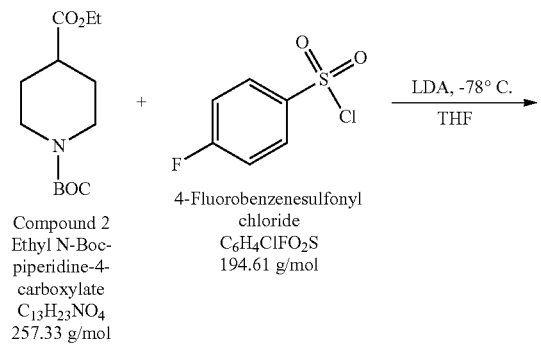

Compound 2
Ethyl N-Boc-piperidine-4-carboxylate
C$_{13}$H$_{23}$NO$_4$
257.33 g/mol 4-Fluorobenzenesulfonyl chloride
C$_6$H$_4$ClFO$_2$S
194.61 g/mol

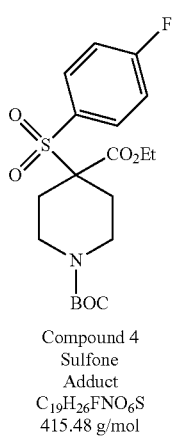

Compound 4
Sulfone Adduct
C$_{19}$H$_{26}$FNO$_6$S
415.48 g/mol

A sulfone adduct (Compound 4) was prepared by generating an anion of a piperidine scaffold, followed by addition of an aryl sulfonyl chloride. In particular, Compound 2 was reacted with LDA, followed by addition of 4-fluorobenzenesulfonyl chloride to produce 80% conversion to desired product.

Example 9: Preparation of 1-tert-butyl 4-ethyl 4-(4-fluorophenylsulfonyl)piperidine-1,4-dicarboxylate (Compound 4)

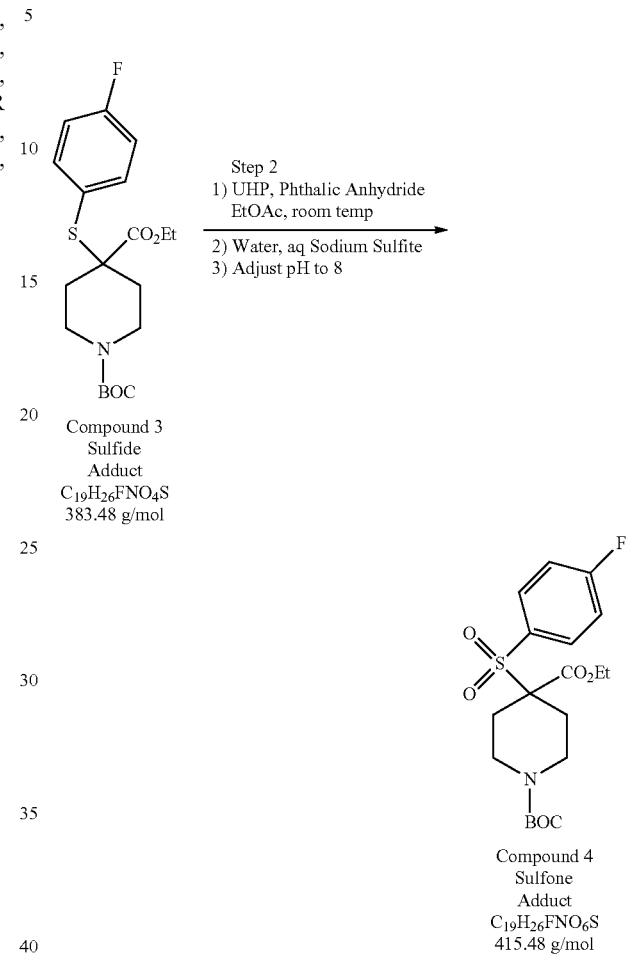

Step 2
1) UHP, Phthalic Anhydride EtOAc, room temp
2) Water, aq Sodium Sulfite
3) Adjust pH to 8

Compound 3
Sulfide Adduct
C$_{19}$H$_{26}$FNO$_4$S
383.48 g/mol

Compound 4
Sulfone Adduct
C$_{19}$H$_{26}$FNO$_6$S
415.48 g/mol

A 5 liter glass reactor (3-necked), equipped with an overhead mechanical stirrer, J-Kem thermocouple, cooling bath (water bath at 15-20° C.), nitrogen inlet, and an additional funnel, was charged with ethyl acetate (1.5 liters), urea hydrogen peroxide (UHP, 132.61 g, 1.41 moles), and Compound 3 (180.00 g, 0.469 moles). Solid phthalic anhydride (209.16 g, 1.41 moles) was added over 5 minutes and ethyl acetate (700 mL) was used as a rinse. The resulting mixture was allowed to stir overnight while the cooling bath remained in place. After 18 hours, HPLC analysis showed complete conversion to the desired sulfone. The reaction slurry was filtered (to remove urea and phthalic acid), and the filtrate was washed with a solution of aqueous 10% sodium sulfite (1.27 liters). The organic layer was digested with aqueous 10% sodium carbonate (800 mL), washed with brine, dried with sodium sulfate, concentrated, and chased with heptane to provide Compound 4 (off-white solid, 193.61 g, 99.3% yield, HPLC purity: 100% AUC, $^1$H NMR and $^{13}$C NMR analysis: conforms to structure). $^1$H NMR (CDCl$_3$, 400 MHz): δ 7.81 (m, 2H), 7.25 (m, 2H), 4.20 (m, 4H), 2.63 (vbs, 2H), 2.30 (bs, 2H), 2.04 (td, 2H, J=12.0, 4.0 Hz), 1.45 (s, 9H), 1.25 (t, 3H, J=8.0 Hz). $^{13}$C NMR (CDCl$_3$, 100 MHz): δ 167.66, 166.7, 165.10, 154.40, 133.26, 133.16, 131.11, 131.08, 116.41, 116.18, 80.26, 77.48, 77.16, 76.84, 72.58, 62.77, 28.41, 27.80, 13.99, 0.05. HRMS (ESI-ToF): m/z calcd for $C_{19}H_{26}FNNaO_6S^+$ [M+Na]+: 438.1363, found 438.1361. m.p. 89-97° C.

Example 10: Preparation of Ethyl 4-(4-Fluorophenylsulfonyl)Piperidine-4-Carboxylate Hydrochloride (Compound 5)

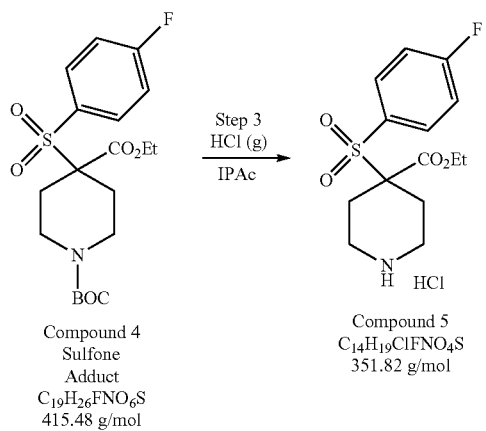 [SMILES: CCOC(=O)C1(S(=O)(=O)c2ccc(F)cc2)CCN(C(=O)OC(C)(C)C)CC1 ; CCOC(=O)C1(S(=O)(=O)c2ccc(F)cc2)CCNCC1 ; Cl ; "IPAc"]

Compound 4
Sulfone Adduct
$C_{19}H_{26}FNO_6S$
415.48 g/mol

Compound 5
$C_{14}H_{19}ClFNO_4S$
351.82 g/mol

Into a solution of Compound 4 (10.25 g, 24.7 mmol) in isopropylacetate (IPAc, 120 mL) was sparged HCl gas (10.00 g), and the resulting solution was allowed to stir overnight at room temperature. HPLC analysis confirmed the absence of starting material. The mixture was concentrated under reduced pressure to afford Compound 5 (8.72 g, 100% yield, HPLC purity: 100% AUC, $^1$H NMR and $^{13}$C NMR analysis: conforms to structure). $^1$H NMR (DMSO-d$_6$, 400 MHz): δ 9.65 (bs, 1H), 9.42 (bs, 1H), 7.89 (m, 2H), 7.58 (t, 2H, J=8.8 Hz), 4.13 (q, 2H, J=14.4 Hz), 3.41 (d, 2H J=13.2 Hz), 2.76 (bs, 2H), 2.32 (m, 4H), 1.10 (t, 3H, J=7.2 Hz). $^{13}$C NMR (CDCl$_3$, 100 MHz): δ 170.74, 167.94, 165.97, 165.36, 133.46, 133.36, 130.33, 130.30, 116.79, 116.56, 77.47, 77.15, 76.84, 70.05, 67.69, 63.58, 41.32, 25.12, 21.88, 21.50, 13.92, 0.05. HRMS (ESI-ToF): m/z calcd for $C_{14}H_{19}FNO_4S^+$ [M+H]+: 316.1019, found 316.1019.

Example 11: Preparation of ethyl 4-(4-fluorophenylsulfonyl)-1-(prop-2-vinyl)piperidine-4-carboxylate (Compound 6)

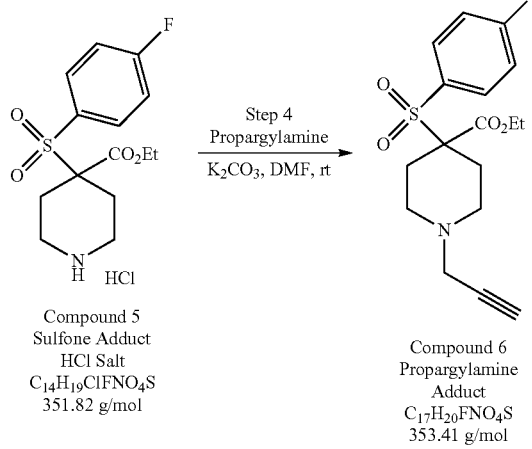

Compound 5
Sulfone Adduct
HCl Salt
$C_{14}H_{19}ClFNO_4S$
351.82 g/mol

Compound 6
Propargylamine Adduct
$C_{17}H_{20}FNO_4S$
353.41 g/mol

In a 2-liter reactor, Compound 5 (30.00 g, 85.27 mmol) was charged with anhydrous DMF (600 mL) and potassium carbonate (23.8 g, 172.20 mmol), and the resulting mixture was allowed to stir (mechanical stirring) for 10 minutes. Propargylamine (97% purity, 10.35 g, 87.00 mmol) was added, and the reaction was allowed to stir for 23 hours at room temperature in which HPLC analysis revealed 11.75% AUC of unreacted Compound 5 and 87.3% AUC of Compound 6. The reaction was charged with an additional portion of propargylamine (1.58 g, 1.00 mL, 8.41 mmol), and the reaction was allowed to stir for an additional 1 hour at room temperature until HPLC indicated that the reaction was complete (2.3% AUC of unreacted Compound 5 was noted and 96.3% AUC of Compound 6). The reaction mixture was transferred to a 5-liter reactor and diluted with ice-cold USP purified water (2.5 liters) to initiate crystallization. The resulting slurry was stirred overnight at 0-5° C. via mechanical stirring, filtered, washed with USP water (150 mL), and pulled dry under a stream of nitrogen to provide Compound 6 (28.44 g, 94.4% yield, light beige solids, HPLC analysis: 99.81% AUC, $^1$H NMR and $^{13}$C NMR analysis: conforms to desired product). $^1$H NMR (CDCl$_3$, 400 MHz): δ 7.82 (m, 2H), 7.23 (m, 2H), 4.21 (q, 2H, J=12.0 Hz), 3.26 (d, 2H, J=4.0 Hz), 2.90 (m, 2H), 2.39 (m, 2H), 2.20 (m, 5H), 1.25 (t, 3H, J=12.0 Hz). $^{13}$C NMR (CDCl$_3$, 100 MHz): δ 167.5, 166.8, 165.0, 133.2, 133.1, 131.4, 116.3, 116.1, 78.2, 77.4, 77.1, 76.8, 73.5, 71.9, 62.5, 49.1, 46.6, 49.1, 46.6, 28.1, 14.0. HRMS (ESI-ToF): m/z calcd for $C_{17}H_{21}FNO_4S^+$ [M+H]+: 354.1175, found 354.1176.

Example 12: Preparation of ethyl 1-(prop-2-ynyl)-4-(4-(4-(trifluoromethoxy)phenoxy)phenylsulfonyl)piperidine-4-carboxylate (Compound 7)

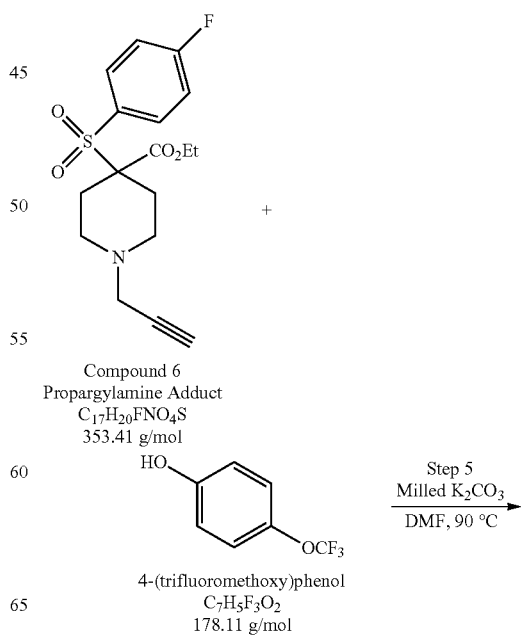

Compound 6
Propargylamine Adduct
$C_{17}H_{20}FNO_4S$
353.41 g/mol 4-(trifluoromethoxy)phenol
$C_7H_5F_3O_2$
178.11 g/mol

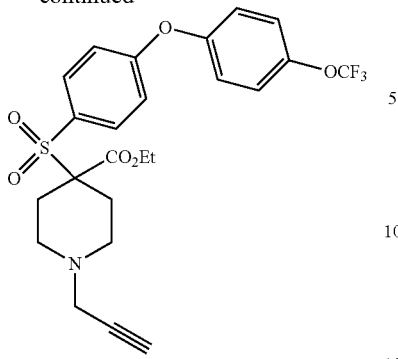

Compound 7
Diaryl Ether Adduct
C$_{24}$H$_{24}$F$_3$NO$_6$S
511.51 g/mol

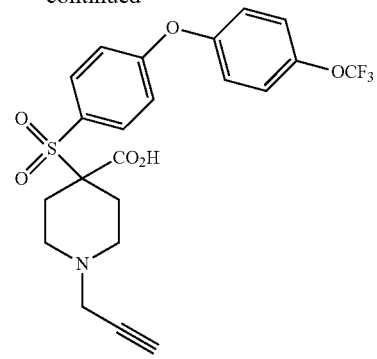

Compound 8
Diaryl Ether Free Acid
C$_{22}$H$_{20}$F$_3$NO$_6$S
483.46 g/mol

A 500-mL reactor equipped with an overhead mechanical stirrer, J-Kem thermocouple, heating mantle, nitrogen inlet, and an additional funnel, was charged with Compound 6 (24.86 g, 70.34 mmol), anhydrous DMF (125 mL), milled potassium carbonate (19.54 g, 141.38 mmol), and 4-(trifluoromethoxy)phenol (25.10 g, 140.69 mmol). The reaction was heated at 90° C. for 19 hours until HPLC analysis showed that the reaction was complete. The reaction mixture was cooled to room temperature and DMF was removed on a rotary evaporator under reduced pressure at 40-60° C. The residue was diluted with MTBE/Toluene (1:1, 300 mL) and washed with 1M NaOH (2×250 mL), USP purified water (250 mL), and brine (250 mL). The solution was dried with sodium sulfate, filtered, and concentrated to furnish Compound 7 (36.06 g, 100% yield, oil, HPLC analysis: 98.03% AUC, $^1$H NMR and $^{13}$C NMR analysis conforms to desired product). $^1$H NMR (CDCl$_3$, 400 MHz): δ 7.76 (m, 2H), 7.27 (m, 2H), 7.10 (m, 2H), 7.06 (m, 2H), 4.23 (m, 2H), 3.25 (s, 2H), 2.90 (bs, 2H), 2.40 (bd, 2H), 2.19 (m, 5H), 1.27 (m, 3H). $^{13}$C NMR (CDCl$_3$, 100 MHz): δ 167.0, 162.5, 153.3, 146.1, 132.8, 129.6, 123.0, 121.6, 117.3, 78.3, 77.4, 77.1, 76.7, 73.4, 72.0, 62.4, 49.3, 46.7, 28.3, 14.0. HRMS (ESI-ToF): m/z calcd for C$_{24}$H$_{25}$F$_3$NO$_6$S$^+$ [M+H]$^+$: 512.1355, found 512.1353.

Example 13: Preparation of ethyl 1-(prop-2-ynyl)-4-(4-(4-(trifluoromethoxy)phenoxy)phenylsulfonyl) piperidine-4-carboxylate (Compound 8)

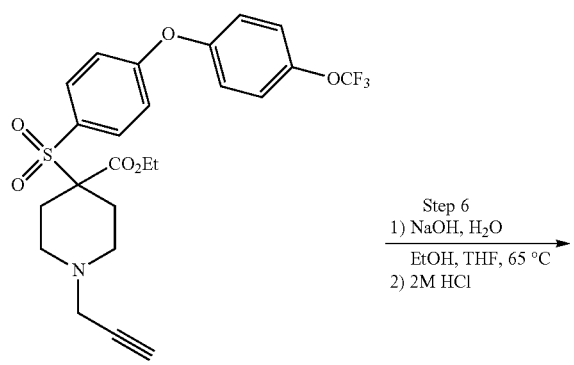

Compound 7
Diaryl Ether Adduct
C$_{24}$H$_{24}$F$_3$NO$_6$S
511.51 g/mol

Step 6
1) NaOH, H$_2$O
EtOH, THF, 65 °C
2) 2M HCl

A 2-liter reactor equipped with an overhead mechanical stirrer, J-Kem thermocouple, heating mantle, reflux condenser with nitrogen inlet, and an additional funnel, was charged with a solution of Compound 7 (28.50 g, 55.72 mmol) in EtOH/THF (1:1, 850 mL), and a solution of NaOH (22.30 g, 557.17 mmol) in USP water (425 mL). The reaction mixture was heated to 65° C. and allowed to stir for 18 hours until HPLC analysis showed complete consumption of Compound 7. The mixture was allowed to cool to ambient temperature, diluted with USP water (300 mL), and concentrated at 45-50° C. on a rotary evaporator to remove EtOH and THF. The aqueous residue was diluted with USP water (600 mL) and the pH was adjusted to pH 2.25 using 2M HCl (282 mL) providing a thick white slurry. The slurry was filtered, washed with USP water (750 mL), pulled dry, and dried further in a vacuum oven at 40° C. to provide Compound 8 (26.30 g, 97.6% yield, white solid, HPLC analysis: 94.4% AUC, $^1$H NMR and $^{13}$C NMR analysis: conforms to desired product). $^1$H NMR (CDCl$_3$, 400 MHz): δ 7.78 (m, 2H), 7.49 (d, 2H, J=8.0 Hz), 7.31 (m, 2H), 7.19 (m, 2H), 3.31 (s, 2H), 3.17 (s, 1H), 2.85 (d, 2H, J=12.0 Hz), 2.19 (d, 2H, J=12.0 Hz), 2.11 (t, 2H, J=12.0 Hz), 1.92 (td, 2H, J=12.0, 4.0 Hz). $^{13}$C NMR (CDCl$_3$, 100 MHz): δ 167.5, 161.7, 153.3, 145.03, 145.01, 132.8, 129.2, 123.32, 122.0, 117.4, 78.5, 76.3, 71.0, 48.4, 45.7, 27.5. HRMS (ESI-ToF): m/z calcd for C$_{22}$H$_{21}$F$_3$NO$_6$S$^+$ [M+H]$^+$: 484.1042, found 484.1042.

Example 14: Preparation of 1-(prop-2-ynyl)-N-(tetrahydro-2H-pyran-2-yloxy)-4-(4-(4-(trifluoromethoxy)phenoxy)phenylsulfonyl)piperidine-4-carboxamide (Compound 9)

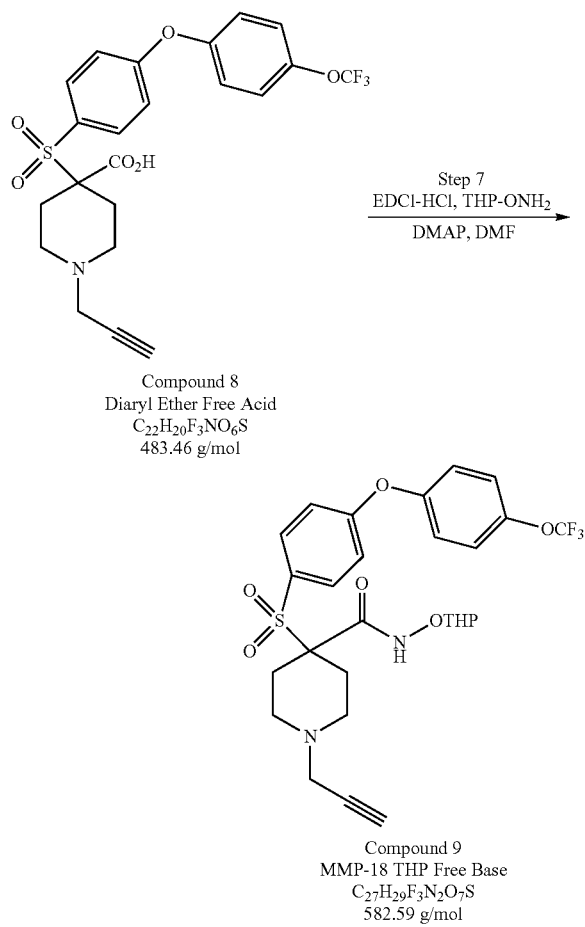

A 500-mL reactor, equipped with a large magnetic stirring bar, J-Kem thermocouple, cooling Dewer, and nitrogen inlet, was charged with Compound 8 (20.00 g, 41.37 mmol) and anhydrous DMF (180 mL). The mixture was allowed to stir for 10 minutes at ambient temperature, then cooled to <5° C. To the cooled mixture was sequentially added o-(tetrahydro-2H-pyran-2-yl)hydroxylamine (7.50 g, 64.02 mmol), EDCl-HCl (10.00 g, 81.85 mmol), and DMAP (8.00 g, 65.36 mmol). The mixture was allowed to stir overnight and gradually warmed to room temperature while the reactor remained in the cooling bath. After 17 hours, HPLC analysis revealed 16.1% of unreacted Compound 8 free acid. The cooling bath was removed and the reaction mixture was allowed to stir an additional 33 hours at room temperature whereby HPLC analysis confirmed that the reaction was complete. The reaction was quenched with USP water (5 mL) and concentrated at 30° C. on a rotovap evaporator to remove DMF. The residue was diluted with ethyl acetate (350 mL) and subsequently washed with saturated aqueous sodium bicarbonate solution (200 mL), brine (200 mL), dried with magnesium sulfate, filtered, and concentrated under reduced pressure to provide crude Compound 9 (34.31 g).

Crude Compound 9 (34.31 g) was purified by silica gel chromatography using a glass gravity column (24 in×3 in) and silica gel (680 g, 60-200 micron, Silicycle, equilibrated with 30% EtOAc in heptane). Crude Compound 9 was dissolved in ethyl acetate (20 mL) then diluted with heptane (20 mL) and subsequently loaded onto the silica bed. The column was eluted with an EtOAc/Heptane gradient (30% to 70%). Appropriate fractions were combined and concentrated to provide Compound 9 (21.78 g, 90.4% yield, white solid, HPLC analysis: 97% AUC, $^1$H NMR and $^{13}$C NMR analysis: conforms to desired product, Mass Spec analysis: [M+H]+=583.46 m/z, FTIR: conforms to desired product). $^1$H NMR (CDCl$_3$, 400 MHz): δ 9.40 (s, 1H), 7.80 (dd, 2H, J=6.9, 2.0 Hz), 7.27 (m, 2H), 7.12 (dd, 2H, J=6.8, 2.3 Hz), 7.05 (dd, 2H, J=6.9, 2.0 Hz), 5.00 (t, 1H, J=2.8 Hz), 4.00 (td, 1H, J=11.2, 2.4 Hz), 3.69 (m, 1H), 3.23 (d, 2H, J=2.4 Hz), 2.92 (m, 2H), 2.35-2.30 (m, 3H), 2.25-2.20 (m, 4H), 1.88-1.76 (m, 3H), 1.68-1.58 (m, 3H). $^{13}$C NMR (CDCl$_3$, 100 MHz): δ 164.0, 162.8, 153.0, 146.1, 146.0, 132.6, 128.0, 123.0, 121.8, 121.7, 119.2, 117.4, 102.0, 78.6, 73.4, 70.3, 62.3, 49.0, 48.9, 46.6, 28.6, 28.4, 27.8, 25.0, 18.3. HRMS (ESI-ToF): m/z calcd for $C_{27}H_{30}F_3N_2O_7S^+$ [M+H]$^+$: 583.1726, found 583.1723.

As shown below, treating a solution of THP-protected MMP-18 (Compound 9, 150 mg) in isopropyl acetate (1.5 mL) and 3,4-Dihydro-2H-pyran (1.0 mL) with 4N HCl in dioxane (0.25 mL) provided THP-protected MMP-18 HCl salt (159 mg, 97.5% yield, HPLC purity: 95% THP HCl salt, and 3% Free Hydroxamic acid).

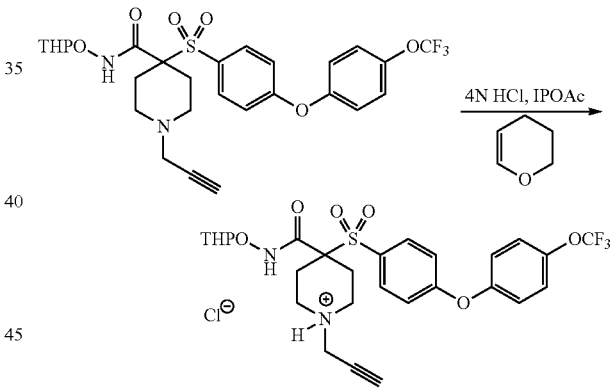

Salt formation of compound 9 was also successful by treating a solution of 9 in ethyl acetate with a solution of oxalic acid dihydrate (1.1 eq) in EtOH/EtOAc.

Example 15: Preparation of TBDMS Carborane

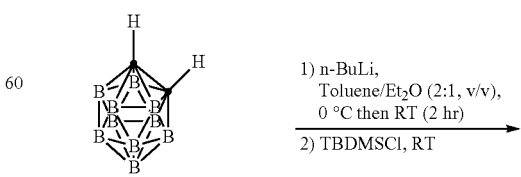

o-Carborane
Chemical Formula: $C_2H_{12}B_{10}$
Molecular Weight: 144.23

-continued

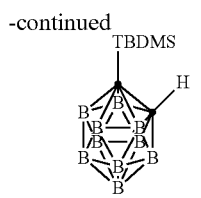

TBDMS Carborane
Chemical Formula: $C_8H_{26}B_{10}Si$
Molecular Weight: 258.49

To a 100 mL round bottom flask was added 3.00 g of o-carborane, 12 mL anhydrous toluene, and 6 mL anhydrous $Et_2O$. The resulting mixture was stirred at room temperature until completely dissolved, then cooled to <5° C. A n-Buli solution (1.66M, 13.2 mL) was added to the mixture over about 5 minutes to result in a murky turbid white mixture. The cooling bath was removed after 5 minutes, and the mixture was stored at room temperature. After 2.5 hours, solid TBDMSCI (3.47 g) was added to the mixture at room temperature as one portion and an endothermic reaction ensued. After 22.5 hours, the reaction slurry was analyzed by TLC (80% Hexane and 20% $Et_2O$), and showed a trace amount of starting material, indicating that the reaction was complete. The reaction mixture was quenched reaction with 30 mL of USP purified $H_2O$, then extracted with $Et_2O$ (3×30 mL). The combined organic layers were dried with $MgSO_4$, filtered, and concentrated to give crude product 7.07 g (pale yellow oil). The crude oil was purified over silica gel as follows. To a glass gravity fitted column (12×2 in) was added sand, n-hexane, and a slurry of 140 g of silica gel (60-200 micron) in n-hexane. The column was further packed under a positive pressure of nitrogen, and a layer of sand was placed on top of the silica bed. Neat crude product (7.07 g) was loaded onto the glass gravity column, and n-hexane was used as a rinse. The column was eluted with n-hexane (250 mL) and 10% $Et_2O$/hexane (825 mL). Ten fractions were collected (each approximately 75 mL) and analyzed using TLC. Appropriate fractions were combined and concentrated on a rotory evaporator at 25-30° C. to give 5.05 g white crystalline solids (93.9% yield). $^1H$ NMR ($CDCl_3$, 400 MHz): δ 3.44 (bs, 1H), 2.87-1.54 (m, 10H), 1.02 (s, 9H), 0.23 (s, 6H). See J. Med. Chem., 2011, 54, 2368. $^{11}B$ NMR (Decoupled, 100 MHz): δ=0.34, −1.76, −7.02, −10.73, −12.31, −13.26. $^{11}B$ NMR (Coupled, 100 MHz): δ=1.01, −0.94, −2.57, −6.29, −7.87, −9.99, −11.62, −12.41, −13.2, −14.26.

Example 16: Preparation of 1-Azido-3-Chloropropane

Cl~~~Br
1-bromo-3-chloropropane
Chemical Formula: $C_3H_6BrCl$
Molecular Weight: 157.44

1) Sodium Azide, DMF, RT
2) Et2O extraction, water washes, Sulfate drying
3) Concentration

→

Cl~~~$N_3$
1-azido-3-chloropropane
Chemical Formula: $C_3H_6ClN_3$
Molecular Weight: 119.55

To a 250 mL round bottomed flask was added 100 mL of anhydrous DMF and 10.02 g of 1-bromo-3-chloropropane, followed by 4.2 g of sodium azide. The reaction was placed in an ambient water bath and stirred overnight (16 hrs) at room temperature. The reaction mixture was diluted with 50 mL of $Et_2O$ and 50 mL USP purified water and stirred for 2-3 minutes. The organic layer (top) was separated. The aqueous layer (bottom) was extracted with $Et_2O$ (2×60 mL). The combined organic layers were washed with USP purified water (3×50 mL), dried with $Na_2SO_4$, filtered and concentrated at 25-30° C. under reduced pressure to give a colorless oil (7.21 g, 95% crude yield), which was taken forward without any further purification. A mixture of 1-azido-3-chloropropane resulted as the major product (81%) and contained ~19% of 1-azido-3-bromopropane. $^1H$ NMR ($CDCl_3$, 400 MHz): δ 3.64 (t, 2H, J=8.0 Hz), 3.51 (t, 3H, J=8.0 Hz), 2.02 (p, 2H, J=12.0, 4.0 Hz). See ACIEE, 56(26), 7420-7424; 2017.

Safety Note on Handling Azido Compounds. Sodium azide is extremely toxic ($LC_{50}$ Inhalation=37 mg/m$^3$ for rats, $LD_{50}$ Dermal=20 mg/kg for rabbits) and very soluble in water (>30 g/100 mL at 0° C.). Sodium azide can be easily absorbed dermally and consequently must be handled with appropriate personal protection equipment (PPE). Sodium azide decomposes above 275° C., generating highly reactive sodium metal. Sodium azide is not compatible with any acid as it spontaneously forms highly explosive hydrazoic acid on contact, even in dilute solution.

Low Molecular Weight Organic Azides. Low molecular weight organic azides are potentially explosive substances that can decompose with a slight input of external energy (heat, friction, pressure etc). Any organic azides where the weight attributed to the azido group exceeds 25% of the molecular weight should be handled with significant caution. It is recommended that a blast shield be used during synthesis and avoid of very large-scale reactions when dealing with these substances. See Sigma-Aldrich, Sodium Azide; MSDS No. 13412 [Online]; Auckland, NZ, Nov. 5, 2012; http://www.sigmaaldrich.com/catalog/product/sial/13412 (accessed Mar. 29, 2017); T. Archibald in Managing Hazardous Reactions and Compounds in Process Chemistry, Vol. 1181 (Eds.: J. A. Pesti, A. F. Abdel-Magid), American Chemical Society: Washington, D C, 2014; pp. 87-109; T. Keicher, S. Löbbecke in Organic Azides: Syntheses and Applications; (Eds.: S. BrAse, K. Banert), Wiley: Chichester, U.K.; 2010; pp 3.

Example 17: Procedure for 1-azido-3-iodopropane

Cl~~~$N_3$
Crude 1-azido-3-chloropropane
Chemical Formula: $C_3H_6ClN_3$
Molecular Weight: 119.55

1) Sodium Iodide, Acetone, reflux 12-32 hrs
2) Concentration to remove acetone
3) Triturate with n-hexane
4) Silica plug (n-hexane)

→

I~~~$N_3$
1-azido-3-iodopropane
Chemical Formula: $C_3H_6IN_3$
Molecular Weight: 211.00

The chloro group was converted to iodine under Finkelstein conditions. See Angewandte Chemie, Int. Ed. Engl. 2017, 56(26), 7420-7424.

To a 1000 mL round bottomed flask (3-necked) was added 19.35 g of NaI, 7.5 g of crude 1-azido-3-chloropropane, and 190 mL of acetone. The reaction was purged with $N_2$, heated to 52° C., then covered with foil. After 40 hours, the reaction was allowed to cool to room temperature. The reaction mixture (yellow slurry) was filtered over a pad of Celite, washed with acetone (~100 mL), and the resulting yellow filtrate was concentrated on a rotovap at 25-30° C. to remove acetone. After concentration, an orange-yellow residue was obtained (oily solids, 26.2 g). About 50 mL of hexane was added to the oil/solid residue (yellowish-orange), which changed the color to a greenish solid. The slurry overnight at room temperature then passed over a short silica plug (65 g) packed in hexane. The resulting mixture was slushed with n-hexane to collect fractions (each 50-70 mL). Appropriate fractions were combined and concentrated at 25° C. to give 10.77 g of a colorless oil. (81.3%). $^1$H NMR ($CDC_3$, 400 MHz): 3.44 (t, 2H), 3.25 (t, 2H), 2.04 (quintet, 2H).

Example 18: Preparation of TBDMS Propyl Azido Carborane

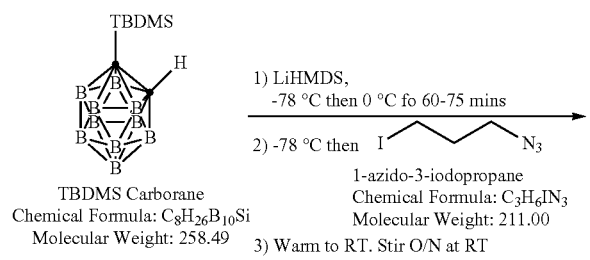

To a dry 100 mL round bottomed flask under a nitrogen atmosphere was added anhydrous THF (18 mL) and 1M LiHMDS (9.7 mL). The mixture was cooled to −78° C. A solution of TBDMS carborane (2.00 g) in anhydrous THF (10 mL) was added to the cryogenic mixture via syringe over 5 min such that the temperature was maintained ≤−65° C. The reaction mixture was allowed to stir an additional 5 minutes at −78° C. then allowed to warm to 0° C., stirred an additional 1.25 hrs at 0° C., and cooled to −78° C. A solution of 1-azido-3-iodopropane (2.15 g) in anhydrous THF (12 mL) was added over 3 minutes at −78° C. The reaction was allowed reaction to stir at −78° C. for 10 minutes, then allowed to warm to room temperature and stirred an additional 1.25 hours at ambient temperature. The reaction was cooled to 0° C., quenched with USP purified water (5 mL), concentrated under reduced pressure, and extracted with diethyl ether (2×20 mL). The combined organic layers were dried with sodium sulfate, filtered and concentrated under reduce pressure to give a crude yellow oil (3.13 g). The crude oil (3.13 g) was dissolved in DCM/n-hexane (3.5 mL, 25/75, v/v) and passed through a large silica plug (40 g) packed in DCM/n-hexane (25/75, v/v). The silica plug was flushed with DCM/n-hexane (200 mL, 25/75, v/v) to collect 8 fractions (each about 10-15 mL). Fractions 2-6 were combined and concentrated to give 2.58 g. (97.7% yield, white solid). The product was stored at 5-10° C. $^1$H NMR ($CDCl_3$, 400 MHz): δ 3.32 (t, 2H), 3.15-1.5 (m, 14H), 1.07 (s, 9H), 0.34 (s, 6H). See Angewandte Chemie, Int. Ed. Engl. 2017, 56(26), 7420-7424. $^{11}$B NMR (Decoupled, 100 MHz): δ=0.29, −3.76, −7.29, −10.18. $^{11}$B NMR (Coupled, 100 MHz): δ=0.99, −0.56, −3.13, −4.62, −6.57, −8.16, −9.48, −11.24

Example 19: Preparation of 1,4 and 1,5-Disubstituted Click Products via Thermal Click Reaction

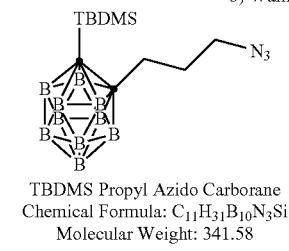

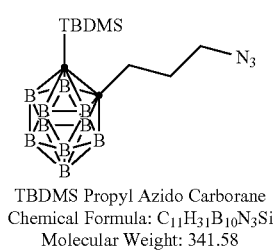

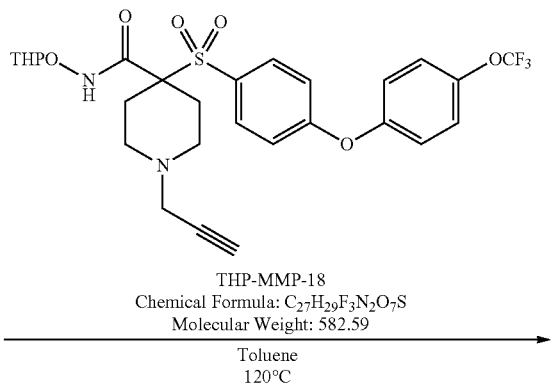

-continued

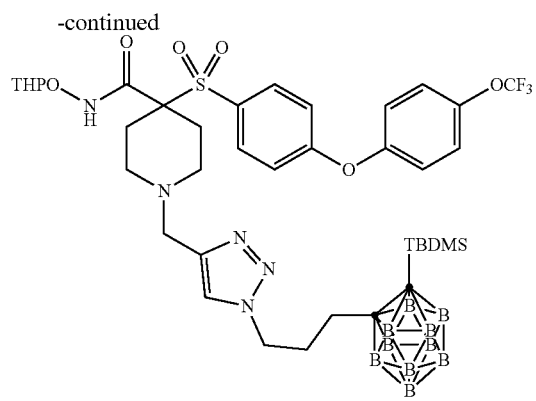

Mixture of 1,4 and 1,5 Click Products
THP MMP-18 Click TBDMS Product
Chemical Formula: $C_{38}H_{60}B_{10}F_3N_5O_7SSi$
Molecular Weight: 924.17

To a 100 mL round bottomed flask was added carboranyl azide (1.00 g), alkyne 9 (1.54 g) and anhydrous toluene (50 mL). The mixture was stirred for 10 minutes at ambient temperature and the mixture was equally portioned into 6 different pressure vials (ChemGlass, 40 mL) where each vial contained 8.3-8.5 mL of mixture. Each mixture was purged with argon, placed on a heating block at 120° C., and allowed to stir at 120° C. for 58 hours. HPLC analysis of each reaction vial indicated that there was ~20% unreacted alkyne, indicating that the reaction was complete to avoid product degradation and impurity introduction. HPLC analysis confirmed that the thermal Huisgen 1,3-Dipolar Cycloaddition reaction gives 1,4-Click and 1,5-Click products with a ratio of 1.6 to 1, respectively, which agrees with Sharpless' study (Sharpless, *Angew. Chem. Int. Ed.,* 2002, 41, 2596-2599) of determining the component ratio of the regioisomers.

All six reactions (at room temperature) were combined and concentrated under reduced pressure to provide a crude oil (2.76 g). The crude oil was dissolved in DCM (30 mL), treated with silica gel (6.9 g, 60-200 micron, Silicylcle), and concentrated to dryness to give dry-loaded material on silica which was placed and packed in a 65 g solid loading cartridge. An 80 g RediSep Rf Gold silica gel column cartridge was equilibrated with ethyl acetate/n-hexane (40/60, 2CV), 100% ethyl acetate (1CV), and ethyl acetate/n-hexane (40/60, 2CV). The purification was accomplished using a ethyl acetate/n-hexane step-gradient from ethyl acetate/n-hexane (40/60) to 100% ethyl acetate. The elution of components were in the following order: starting material, 1,5-Click product, and lastly 1,4-click product. Appropriate fractions were combined and concentrated to isolate recovered starting material (compound 9, 0.36 g, colorless oil, TLC Rf=0.51 using 100% EtOAc), 1,5-click product (colorless glass solid, 0.60 g, 32.1% yield, corrected yield for recovered SM, TLC Rf=0.35 using 100% EtOAc), and 1,4-click product (white solid, 0.90 g, 48.1% yield, corrected yield for recovered SM, TLC Rf=0.15 using 100% EtOAc).

1,4-Click Product. HPLC purity: 96% AUC (retention time: 26.5 min). $^1$H NMR (CDC$_3$, 400 MHz): δ 9.38 (s, 1H), 7.80 (m, 2H), 7.41 (s, 1H), 7.28 (d, 2H), 7.11 (d, 2H), 7.04 (d, 2H), 4.99 (s, 1H), 4.33 (t, 2H, J=6.4 Hz), 3.99 (bt, 1H, J=10.3 Hz), 3.68 (bd, 1H), 3.59 (s, 2H), 2.93 (bs, 2H), 2.40-1.20 (m, 26H), 0.98 (s, 9H), 0.23 (s, 6H). $^{13}$C NMR (CDCl$_3$, 100 MHz): δ 164.1, 162.9, 152.9, 146.1, 145.3, 132.5, 128.5, 123.0, 122.3, 121.8, 117.4, 102.1, 79.8, 77.4, 77.2, 77.0, 76.7, 76.2, 70.5, 62.4, 52.9, 49.8, 49.8, 49.2, 34.9, 30.7, 28.5, 28.3, 27.8, 27.4, 24.9, 20.3, 18.24, -2.60. HRMS (ESI-ToF): m/z calcd for $C_{38}H_{61}B_{10}F_3N_5O_7SSi^+$ [M+H]$^+$: 926.4944, found 926.5007. FTIR: 2941.1, 2863.3, 2575.8, 1686.5, 1587, 1501.4, 1488.6, 1316.7, 1244.2, 1220.2, 1185.8, 1149.4, 1133.2, 1086.5, 1038.0, 944.4, 896.8, 858.2, 838.3, 752.8, 731.2, 677.0 cm$^{-1}$. $^{11}$B NMR (Decoupled, 100 MHz): δ=0.27, -3.86, -7.47, -10.51. $^{11}$B NMR (Coupled, 100 MHz): δ=1.09, -0.59, -3.17, -4.34, -6.64, -8.41, -9.41, -10.81

1,5-Click Product. HPLC purity: 95% AUC (retention time: 27.4 min). $^1$H NMR (CDC$_3$, 400 MHz): δ 9.43 (s, 1H), 7.8 (d, 2H), 7.49 (s, 1H), ? (?, 3H), 7.1 (d, 2H), 7.05 (d, 2H), 5.01 (bs, 1H), 4.39 (t, 2H), 3.99 (bt, 1H), 3.7 (d, 1H), 3.49 (s, 2H), 2.8 (?, 2H), 1.58-2.30 (c, 24H), 1.25 (s, 1H), 1.00 (s, 9H). $^{13}$C NMR (CDC$_3$, 100 MHz): δ 164.16, 162.91, 152.91, 1461, 134.74, 132.63, 132.42, 127.82, 123.03, 121.80, 121.71, 117.50, 101.87, 80.13, 77.35, 77.23, 77.03, 76.71, 76.35, 70.15, 62.30, 50.20, 49.93, 49.74, 47.42, 35.04, 30.11, 28.30, 28.10, 27.77, 27.43, 24.92, 20.32, 18.12, -2.59. HRMS (ESI-ToF): m/z calcd for $C_{38}H_{61}B_{10}F_3N_5O_7SSi^+$ [M+H]$^+$: 926.4944, found 926.4999. FTIR: 2939.8, 2869.6, 2579.3, 1685.9, 1586.8, 15014, 1488.7, 1319.0, 1295.5, 1220.0, 1243.6, 1185.7, 1149.9, 1134.3, 1086.8, 1037.2, 957.7, 944.6, 896.9, 873.3, 858.7, 838.3, 818.4, 732.1, 677.3 cm$^{-1}$. $^{11}$B NMR (Decoupled, 100 MHz): δ=0.37, -3.85, -7.43, -10.47. $^{11}$B NMR (Coupled, 100 MHz): δ=0.94, -0.47, -4.55, -6.70, -8.43, -10.83.

Example 20: Preparation of the THP MMP-18 1,4-Click Product

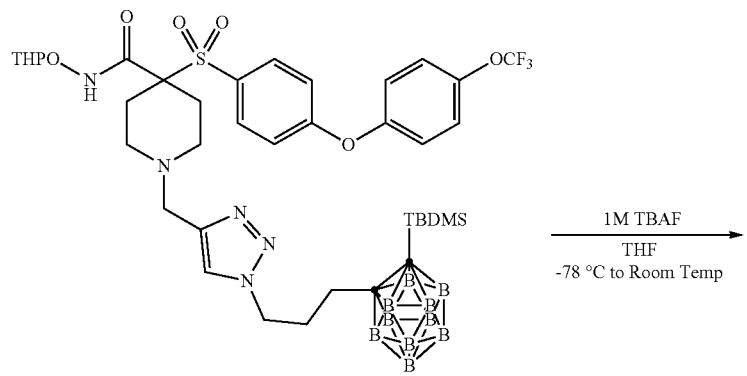

1,4 - 1,5 Click Products
THP MMP-18 Click TBDMS Product
Chemical Formula: $C_{38}H_{60}B_{10}F_3N_5O_7SSi$
Molecular Weight: 924.17

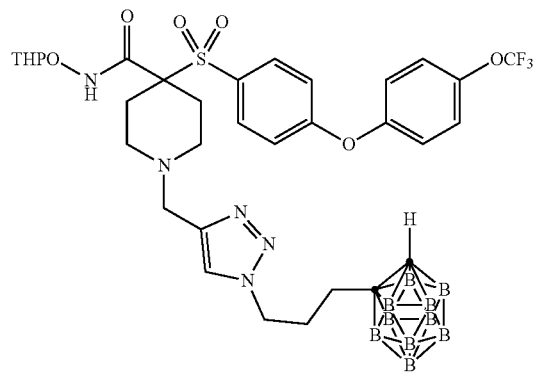

1,4 - Click Product
THP MMP-18 1,4-Click Product
Chemical Formula: $C_{32}H_{46}B_{10}F_3N_5O_7S$
Molecular Weight: 809.91

To 1,4-click TBDMS protected product (128 mg) was added anhydrous THF (1.25 mL) and the resulting mixture was cooled solution to −78° C. To the cryogenic mixture was added a solution of 1M TBAF in THF (0.17 mL) over approximately 30 seconds. After 5 minutes, the cooling bath was removed and then the reaction was permitted to warm to room temperature. After 30 minutes at room temperature, TLC analysis (100% EtOAc) showed complete consumption of starting material. The reaction mixture was concentrated to a crude oil residue which was dissolved in ethyl acetate (2 mL) and washed with water (1 mL, pH 7-7.5). The aqueous phase was extracted ethyl acetate (1 mL). The combined organic layers were washed with water (pH 7-7.5, 1 mL), dried with sodium sulfate, filtered, and concentrated under reduced pressure to give crude product (108 mg). The crude oil (108 mg) was dissolved in ethyl acetate (0.5 mL) and passed through a silica plug (0.27 g) in ethyl acetate. The plug was flushed with ethyl acetate. Appropriate fractions were combined and concentrated to afford desired 1,4-click THP protected product (88 mg, 78.6% yield, colorless oil that solidifies upon standing) which was taken forward without any further purification since it contains residual tert-butyldimethylsilyl fluoride (which will be removed downstream). HPLC purity: 92.3% AUC (retention time: 24.1 min). HRMS (ESI-ToF): m/z calcd for $C_{32}H_{47}B_{10}F_3N_5O_7S^+$ [M+H]$^+$: 812.4079, found 812.4131. FTIR: 2946.6, 2850.4, 2586.7, 1682.0, 1587.0, 1501.5, 1488.4, 1461.3, 1293.7, 1219.9, 1244.5, 1185.9, 1132.6, 1149.0, 1086.1, 1037.5, 1021.5, 956.2, 944.2, 896.0, 873.1, 835.1, 816.0, 754.5, 722.7, 678.9, 645.0 cm$^{-1}$

Example 21: Preparation of 1,4-Click Carboranyl MMP-18 HCl Salt (Compound 16)

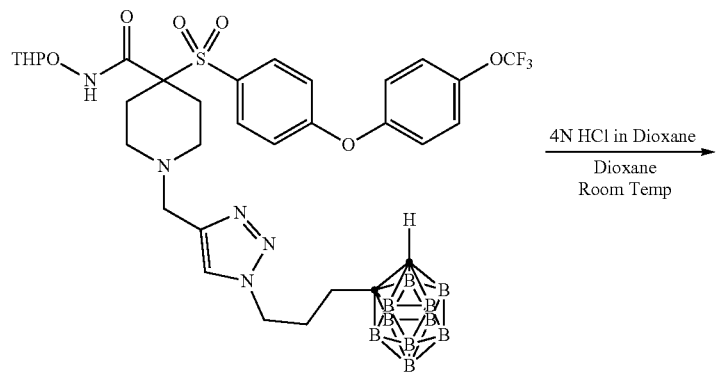

THP MMP-18 Click Product
Chemical Formula: $C_{32}H_{46}B_{10}F_3N_5O_7S$
Molecular Weight: 809.91

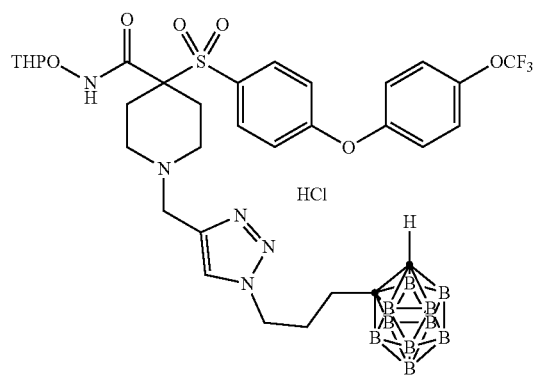

1,4-Click Carboranyl MMP-18 HCl Salt
Chemical Formula: $C_{27}H_{39}B_{10}ClF_3N_5O_6S$
Molecular Weight: 762.25

To a 10 mL vial containing THP protected 1,4-Click product (88 mg) under nitrogen atmosphere was added anhydrous dioxane (0.9 mL). The mixture was allowed to stir until complete dissolution was achieved. To the resulting solution was added 4N HCl in dioxane (0.14 mL) and the reaction was allowed to stir for 2 hours at room temperature where HPLC analysis revealed that the reaction was complete. The reaction mixture was concentrated under reduced pressure at 30±5° C. to give a crude oil. The crude oil was dissolved in dichloromethane (1 mL), and diethyl ether (3 mL) was added to generate a white slurry. The slurry was allowed to stir at ambient temperature for 1.5 hours, filtered, and the filter cake was washed with diethyl ether (2 mL) and n-heptane (5 mL), pulled dry under nitrogen, and further dried in vacuo at room temperature to provide the title 1,4-Click Carboanyl MMP-18 HCl salt (60 mg, white solids, 72.2% yield, Lot PR074-062-5). HPLC purity: 95.1% AUC (retention time: 22.7 min). HRMS (ESI-ToF): m/z calcd for $C_{27}H_{39}B_{10}F_3N_5O_6S^+$ [M+H]$^+$: 728.3504, found 728.3540. $^{11}$B NMR (Decoupled, 100 MHz): δ=18.56, −2.94, −6.09, −9.67, −12.20, −13.17. $^{11}$B NMR (Coupled, 100 MHz): δ=18.56, −2.15, −3.64, −5.21, −6.32, −8.91, −11.08, −12.95, −13.86.

Example 22: Preparation of the THP MMP-18 1,5-Click Product

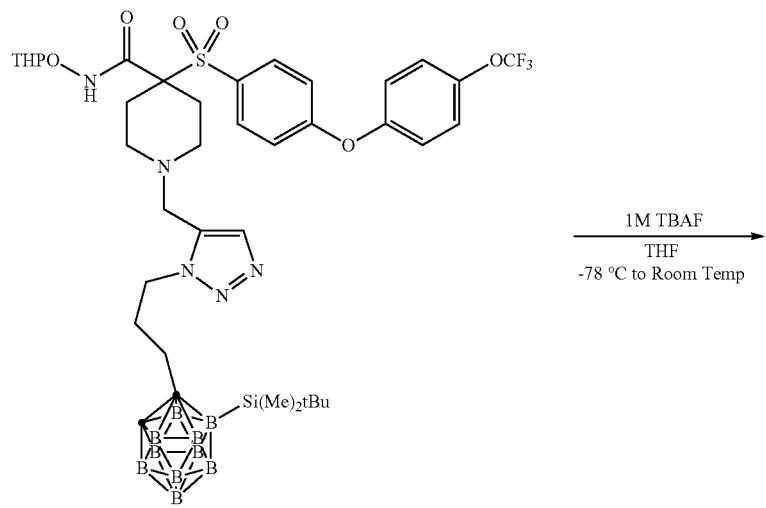

THP MMP-18 1,5-Disubstituted Click TBDMS Product
Chemical Formula: $C_{38}H_{60}B_{10}F_3N_5O_7SSi$
Molecular Weight: 924.17

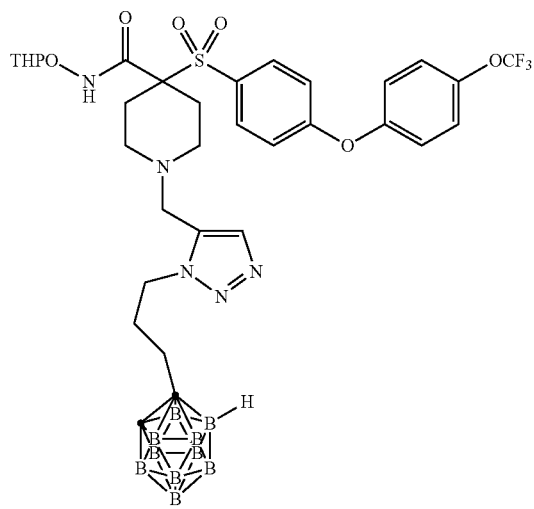

1,5 - Click Product
THP MMP-18 Click Product
Chemical Formula: $C_{32}H_{46}B_{10}F_3N_5O_7S$
Molecular Weight: 809.91

To 1,5-click TBDMS protected product (71 mg) was added anhydrous THF (0.9 mL) and the resulting mixture was cooled solution to −78° C. To the cryogenic mixture was added a solution of 1M TBAF in THF (90 μL). After 5 minutes, the cooling bath was removed and then the reaction was allowed to warm to room temperature. After 75 minutes at room temperature, TLC analysis (100% EtOAc) showed complete consumption of starting material. The reaction mixture was concentrated to a crude oil residue, which was dissolved in ethyl acetate (2 mL) and washed with water (1 mL, pH 7-7.5). The aqueous phase was extracted ethyl acetate (2 mL). The combined organic layers were washed with water (pH 7-7.5, 1 mL), dried with sodium sulfate, filtered, and concentrated under reduced pressure to give crude desired product (82 mg, theoretically 62 mg present), which was taken forward without any further purification since it contains residual tert-butyldimethylsilyl fluoride (which will be removed downstream). HPLC purity: 95.2% AUC (retention time: 26.4 min). HRMS (ESI-ToF): m/z calcd for $C_{32}H_{47}B_{10}F_3N_5O_7S^+$ [M+H]⁺: 812.4079, found 812.4139.

Example 23: Preparation of 1,5-Click Carboranyl MMP-18 HCl Salt (Compound 19)

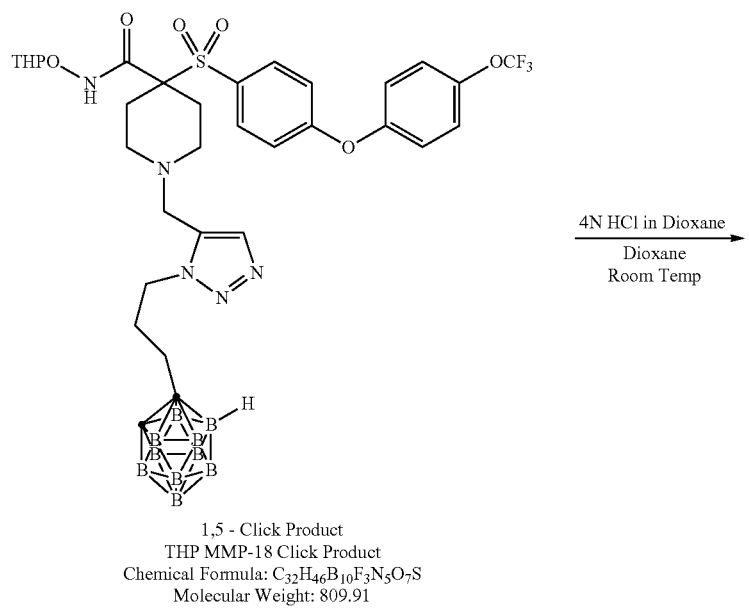

1,5 - Click Product
THP MMP-18 Click Product
Chemical Formula: $C_{32}H_{46}B_{10}F_3N_5O_7S$
Molecular Weight: 809.91

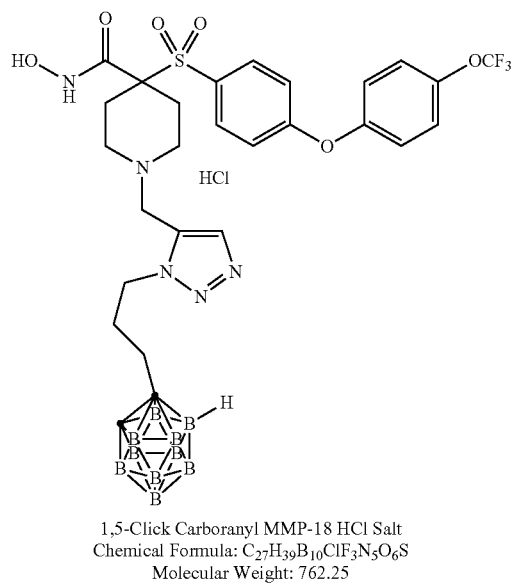

1,5-Click Carboranyl MMP-18 HCl Salt
Chemical Formula: $C_{27}H_{39}B_{10}ClF_3N_5O_6S$
Molecular Weight: 762.25

To a 10 mL vial containing crude THP protected 1,5-Click product (82 mg) under nitrogen atmosphere was added anhydrous dioxane (0.9 mL). The mixture was allowed to stir until complete dissolution was achieved. To the resulting solution was added 4N HCl in dioxane (0.14 mL), and the reaction was allowed to stir for 2.5 hours at room temperature. HPLC analysis revealed that the reaction was complete. The reaction mixture was concentrated under reduced pressure at 30±5° C. to give a crude oil. The crude oil was dissolved in dichloromethane (0.5 mL), and diethyl ether (3 mL) was slowly added to generate a white slurry. The slurry was allowed to stir at ambient temperature for 20 min, filtered, and the filter cake was washed with diethyl ether (2.5 mL) and n-hexane (5 mL), pulled dry under nitrogen, and further dried in vacuo at room temperature to provide the title 1,5-Click Carboanyl MMP-18 HCl salt (58 mg, white solids, 99% yield). HPLC purity: 92.2% AUC (retention time: 23.2 min). HRMS (ESI-ToF): m/z calcd for $C_{27}H_{39}B_{10}F_3N_5O_6S^+$ [M+H]$^+$: 728.3504, found 728.3538. $^{11}$B NMR (Decoupled, 100 MHz): δ=18.55, −2.90, −6.26, −9.74, −12.24, −13.14. $^{11}$B NMR (Coupled, 100 MHz): δ=18.58, −2.13, −3.71, −8.99, −11.11, −12.88.

Example 24: Preparation of MMP-18 Carboranyl Ethyl Ester

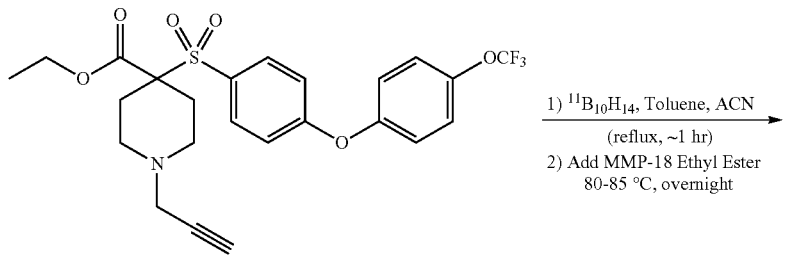

MMP-18 Ethyl Ester
Chemical Formula: $C_{24}H_{24}F_3NO_6S$
Molecular Weight: 511.51

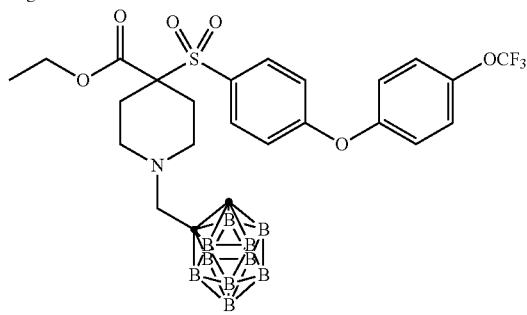

closo-carborane MMP-18 Ethyl Ester
Chemical Formula: $C_{24}H_{34}B_{10}F_3NO_6S$
Molecular Weight: 629.70

A 250 mL round bottomed flask (1-necked) was equipped with a Claisen adapter, reflux condenser with nitrogen inlet, magnetic stirring bar, and a J-Kem thermocouple. To the reactor under nitrogen was added white decaborane (0.90 g), anhydrous toluene (45 mL), and anhydrous ACN (31 mL). The mixture was purged with nitrogen and the reaction flask was covered with foil. The mixture to reflux (temp 82° C.) for 80 minutes, and cooled to room temperature. To the reaction mixture (light yellow solution) at ambient temperature was added a solution of MMP-18 Ethyl Ester (3.13 g) in anhydrous toluene (10 mL), and additional anhydrous toluene (5 mL) was used to quantitatively transfer all ester to the reactor. The reactor was purged with nitrogen and heated to reflux. After 19 hours, the reaction was a dark yellowish-orange solution and the reaction was sampled for HPLC analysis (8 drops of reaction mixture was concentrated and dissolved in 4 mL of ACN). HPLC analysis indicated that the starting material alkynyl ester (18.4 min) was completely consumed. The reaction mixture was cooled to room temperature and was concentrated under reduced pressure at 40-50° C. to give crude product as an orange foam (4.29 g). Crude product was analyzed by HPLC and TLC. TLC Analysis (crude, EtOAc/hept 40/60) was done using a glass backed TLC plate visualizing with UV and 0.4% $PdCl2$ in 3M HCl Crude product (4.29 g) was dissolved in DCM and transferred to a 250 mL round bottomed flask. To the flask was added silica gel (10.0 g, 60-200 micron, Silicycle) and this mixture was concentrated to dryness on rotovap at 25-30° C. to provide dry-loaded crude product. The dry-loaded crude product was loaded into a 65 g solid loading cartridge. An 80 g Redisep Rf Gold silica gel cartridge column was equilibrated with n-hexane (165 mL), ethyl acetate/n-hexane (50/50, 195 mL), and n-hexane (275 mL). Purification on an Isco Rf unit was accomplished using an ethyl acetate/n-hexane gradient (0/100 to 100/0) over 16.5 column volumes. Collected fractions were analyzed analyzed and combined based on HPLC. Like fractions were combined and concentrated under reduced pressure to give desired carboranyl ethyl ester product (1.30 g, 33.8% yield, white foam). HPLC purity: 98.9% AUC (retention time: 32.4 min). $^1$H NMR (CDCl$_3$, 400 MHz): δ 7.73 (m, 2H), 7.27 (m, 2H), 7.13-7.04 (m, 4H), 4.18 (q, 2H, J=8.0 Hz), 3.91 (s, 1H), 3.10-1.50 (complex, 20H), 1.24 (t, 3H, J=8.0 Hz). $^{13}$C NMR (CDCl$_3$, 100 MHz): δ 166.87, 162.67, 153.06, 146.07, 146.06, 132.62, 128.77, 123.05, 121.71, 121.66, 119.15, 117.17, 77.34, 77.02, 76.71, 74.45, 71.41, 62.62, 58.16, 51.96, 13.95. DEPT135: δ 132.62, 123.06, 121.67, 117.18, 62.63, 58.17, 51.95, 13.96. C13APT: δ 166.87, 162.67, 153.06, 146.06, 132.62, 128.78, 123.06, 121.67, 117.18, 77.35, 77.03, 76.71, 74.45, 71.41, 62.62, 58.17, 51.96, 13.96. HRMS (ESI-ToF): m/z calcd for $C_{24}H_{35}B_{10}F_3NO_6S^+$ [M+H]$^+$: 632.3068, found 632.3112. $^{11}$B NMR (Decoupled, 100 MHz): δ=−2.82, −5.21, −8.98, −11.69, −12.89. $^{11}$B NMR (Coupled, 100 MHz): δ=−2.10, −3.73, −5.97, −8.20, −9.83, −12.35.

Fractions 28-32 were pooled and concentrated to give 0.80 g of a yellow foam solid, which was determined to be the nido-form of carboranyl ethyl ester product. HPLC purity: 68.7% AUC (retention time: 26.4 min). HRMS (ESI-ToF): m/z calcd for $C_{24}H_{34}B_9F_3NO_6S^+$ [M+H]$^+$: 620.2896, found 620.3022.

Example 25: Hydrolysis of MMP-18 Carboranyl Ethyl Ester Via Continuous Flow Mode

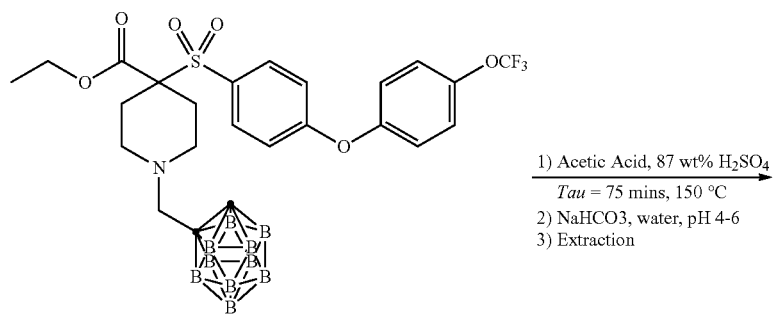

closo-carborane MMP-18 CO₂Et
Chemical Formula: $C_{24}H_{34}B_{10}F_3NO_6S$
Molecular Weight: 629.70

1) Acetic Acid, 87 wt% $H_2SO_4$
$Tau$ = 75 mins, 150 °C
2) NaHCO3, water, pH 4-6
3) Extraction

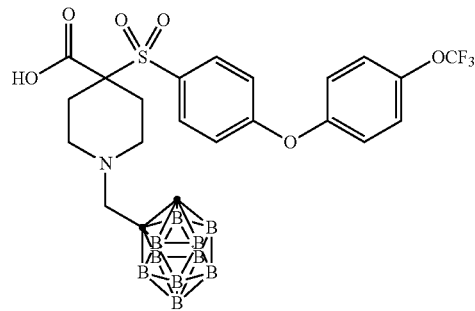

closo-carborane MMP-18 CO₂H
Chemical Formula: $C_{22}H_{30}B_{10}F_3NO_6S$
Molecular Weight: 601.65

MMP-18 Carboranyl Ethyl Ester (0.60 g) was dissolved in acetic acid (150 mL) and allowed to stir at room temperature until complete dissolution was achieved. The ester was passed through a flow apparatus heating to 150° C., followed by neutralization with sodium bicarbonate, extraction with ethyl acetate, and concentration to afford the carboxylic acid.

The acid is then treated with EDCl in the presence of NMM and HOBT in DMF, then treated with $THPONH_2$. The THP-protected Hydroxamate is purified via flash chromatography on silica gel, then deprotected to afford the final closo-carborane hydroxamate final product.

Example 26: Assay for Inhibition of MMP

Serial dilutions of the compound were prepared with 10% DMSO, and 5 µl of each dilution was added to a 50 µl reaction vessel to result in a final DMSO concentration of 1% for each reaction. The enzymes were diluted in 50 mM HEPES buffer pH7.4, 10 mM $CaCl_2$, 0.05% Brij-35, and 1 mM APMA for activation at 37° C. for 2 hours. The enzymatic reactions were conducted in duplicate at room temperature for 30 minutes in a 50 µl mixture containing 50 mM HEPES buffer, pH7.4, 10 mM $CaCl_2$, 0.05% Brij-35, an MMP substrate, an MMP enzyme and a test compound. Fluorescence intensity was measured at an excitation of 328 nm and an emission of 393 nm using a Tecan Infinite M1000 microplate reader.

Phosphatase activity assays were performed in duplicate at each concentration. The fluorescent intensity data were analyzed using the computer software, Graphpad Prism. In the absence of the compound, the fluorescent intensity (Ft) in each data set was defined as 100% activity. In the absence of enzyme, the fluorescent intensity (Fb) in each data set was defined as 0% activity. The percent activity in the presence of each compound was calculated according to the following equation: % activity=(F−Fb)/(Ft−Fb), where F=the fluorescent intensity in the presence of the compound.

The values of % activity versus a series of compound concentrations were then plotted using non-linear regression analysis of Sigmoidal dose-response curve generated with the equation Y=B+(T−B)/1+10((Log EC50−X)×Hill Slope), where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

The structures of the compounds tested and the results are shown below.

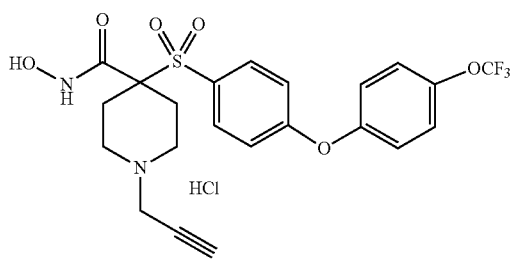

Compound 9 (Control)

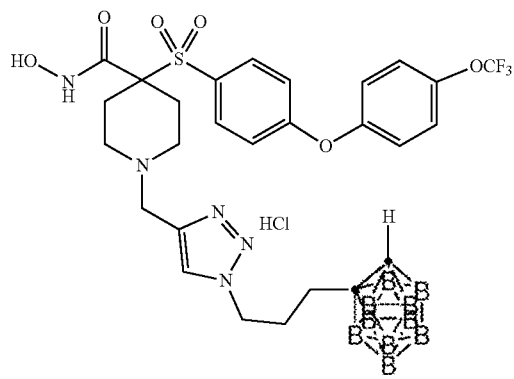

Compound 16
1,4-Click Carboranyl HCl Salt

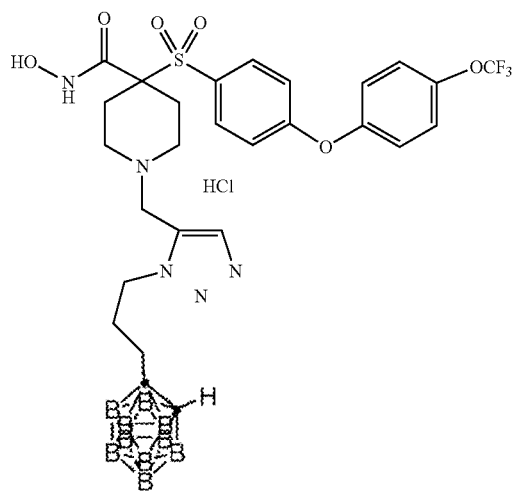

Compound 19
1,5-Click Carboranyl HCl Salt

| Compound | IC$_{50}$ (μM) or % Inhibition | | |
|---|---|---|---|
| | MMP-1 | MMP-2 | MMP-9 |
| 9* | 0.86 | 0.00024 | 0.0003 |
| 16 | >10 μM NI at 10 μM | 0.037, >270x sel* | 0.046, >217x sel*** |
| 19 | >10 μM, 20% at 10 μM | 0.0098, 1020x sel*** | 0.013, 769x sel*** |
| NNGH**** | 0.12 | 0.0027 | 0.005 |

*Literature MMPi for Compound 9: MMP-1 IC$_{50}$ = 2.6 μM, MMP-2 IC$_{50}$ = <0.0001 μM, MMP-9 IC$_{50}$ = 0.0001 μM. See Becker, J. Med. Chem. 2010, 53, 6653-6680.

**no significant inhibition (less than 15%)

***sel = selectivity versus MMP-1

****NNGH (BML-205) is N-Isobutyl-N-(4-methoxyphenylsulfonyl)glycyl hydroxamic acid, a standard MMP inhibitor.

We claim:

1. A compound having a structure of Formula (I), or a pharmaceutically acceptable salt thereof:

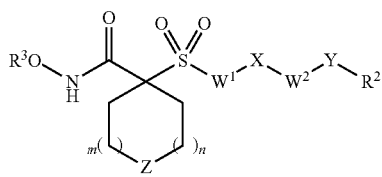

(I)

wherein
m is 1;
n is 1;
$W^1$ and $W^2$ are each absent;
X is aryl;
Y is O or $C_{1-2}$alkylene-O;
Z is $NR^1$;
$R^1$ is $C_{1-6}$alkylene-CB; $C_{1-6}$alkylene-$C_{3-8}$heteroaryl-$C_{1-6}$alkylene-CB, CH($C_{1-3}$alkylene-$C_{3-8}$heteroaryl-CB)$_2$, $C_{1-4}$alkylene-CH($C_{1-3}$alkylene-$C_{3-8}$-heteroaryl-CB)$_2$, CH($C_{1-3}$alkylene-$C_{3-8}$heteroaryl-$C_{1-6}$alkylene-CB)$_2$, $C_{1-4}$alkylene-CH($C_{1-3}$alkylene-$C_{3-8}$ heteroaryl-$C_{1-6}$alkylene-CB)$_2$, C($C_{1-3}$alkylene-$C_{3-8}$-heteroaryl-CB)$_3$, $C_{1-4}$alkylene- C($C_{1-3}$alkylene-$C_{3-8}$-heteroaryl-CB)$_3$, C($C_{1-3}$alkylene-$C_{3-8}$-heteroaryl-$C_{1-6}$alkylene-CB)$_3$, or $C_{1-4}$alkylene-C($C_{1-3}$alkylene-$C_{3-8}$-heteroaryl-$C_{1-6}$alkylene-CB)3;
$R^2$ is aryl-$R^4$ or $C_{1-2}$alkylene-aryl-$R^4$;
$R^3$ is H;
$R^4$ is $OC_{1-6}$alkyl substituted with halo or $C_{1-6}$alkylene-$OC_{1-6}$alkyl substituted with halo; and
CB is carborane,
wherein $C_{3-8}$heteroaryl includes 1, 2, or 3 heteroatoms selected from the group consisting of N, O, and S.

2. The compound or salt of claim 1, wherein X is phenyleneyl.

3. The compound or salt of claim 1, wherein Y is O.

4. The compound or salt of claim 1, wherein $R^1$ is $C_{1-6}$alkylene-CB.

5. The compound or salt of claim 4, wherein $R^1$ is $CH_2$-CB.

6. The compound or salt of claim 1, wherein $R^1$ is $C_{1-6}$alkylene-heteroaryl-$C_{1-6}$alkylene-CB.

7. The compound or salt of claim 6, wherein $R^1$ is $CH_2$-heteroaryl-$CH_2CH_2$-CB or CH2-heteroaryl-$CH_2CH_2CH_2$-CB.

8. The compound or salt of claim 1, wherein $R^1$ is CH($C_{1-3}$alkylene-heteroaryl-CB)$_2$, $C_{1-4}$alkylene-CH($C_{1-3}$alkylene-heteroaryl-CB)$_2$, CH($C_{1-3}$alkylene-heteroaryl-$C_{1-6}$alkylene-CB)$_2$, $C_{1-4}$alkylene-CH($C_{1-3}$alkylene-heteroaryl-$C_{1-6}$alkylene-CB)$_2$, C($C_{1-3}$alkylene-heteroaryl-CB)$_3$, $C_{1-4}$alkylene-C($C_{1-3}$alkylene-heteroaryl-CB)$_3$, C($C_{1-3}$alkylene-heteroaryl-$C_{1-6}$alkylene-CB)$_3$, or $C_{1-4}$alkylene-C($C_{1-3}$alkylene-heteroaryl-$C_{1-6}$alkylene-CB)$_3$.

9. The compound or salt of claim 8, wherein $R^1$ is CH($CH_2$-heteroaryl-CB)$_2$ or C($CH_2$-heteroaryl-CB)$_3$.

10. The compound or salt of claim 8, wherein heteroaryl is triazolenyl.

11. The compound or salt of claim 1, wherein $R^2$ is phenylene-$R^4$ or $C_{1-2}$alkylene-phenylene-$R^4$.

12. The compound or salt of claim 1, wherein $R^4$ is $OC_{1-6}$alkyl substituted with halo.

13. The compound or salt of claim 12, wherein $R^4$ is $OCF_3$ or $OCF_2CF_3$.

14. The compound or salt of claim 13, wherein $R^4$ is $OCF_3$.

15. A pharmaceutical formulation comprising the compound or salt of claim 1 and a pharmaceutically acceptable excipient.

16. A method of inhibiting matrix metalloproteinase ("MMP") in a cell, comprising contacting the cell with the compound or salt of claim 1, in an amount effective to inhibit MMP.

17. A method of treating cancer or rheumatoid arthritis in a subject comprising administering to the subject a therapeutically effective amount of a compound of claim 1.

18. A tert-butyldimethylsilyl ether propyl azido carborane compound having a structure:

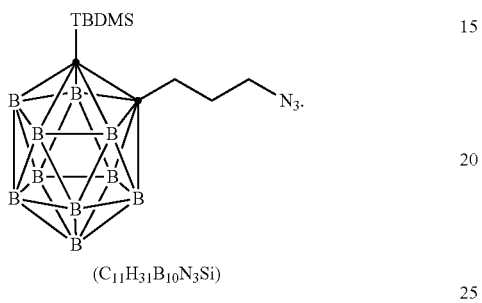

$(C_{11}H_{31}B_{10}N_3Si)$

* * * * *